(12) United States Patent
Papapetropoulos et al.

(10) Patent No.: US 8,257,929 B2
(45) Date of Patent: Sep. 4, 2012

(54) GENE EXPRESSION PROFILING OF PARKINSON'S DISEASE

(75) Inventors: Spiridon Papapetropoulos, Auburndale, MA (US); Jarlath Ffrench-Mullen, Potomac, MD (US); Deborah C. Mash, North Bay Vilage, FL (US)

(73) Assignee: University of Miami, Miami, FL (US)

( * ) Notice: Subject to any disclaimer, the term of this patent is extended or adjusted under 35 U.S.C. 154(b) by 515 days.

(21) Appl. No.: 12/446,339

(22) PCT Filed: Oct. 22, 2007

(86) PCT No.: PCT/US2007/082132
§ 371 (c)(1),
(2), (4) Date: Jun. 4, 2009

(87) PCT Pub. No.: WO2008/070311
PCT Pub. Date: Jun. 12, 2008

(65) Prior Publication Data
US 2010/0298438 A1 Nov. 25, 2010

Related U.S. Application Data

(60) Provisional application No. 60/852,966, filed on Oct. 20, 2006.

(51) Int. Cl.
*C12Q 1/68* (2006.01)
*G01N 33/53* (2006.01)

(52) U.S. Cl. .................................. 435/6.11; 435/7.1
(58) Field of Classification Search .................. None
See application file for complete search history.

(56) References Cited

U.S. PATENT DOCUMENTS
5,953,727 A    9/1999  Maslyn et al.

FOREIGN PATENT DOCUMENTS
WO    WO 99/032660    7/1999

OTHER PUBLICATIONS

Williams, D.R. et al. (2005) Kufor Rakeb Disease: Autosomal Recessive, Levodopa-Responsive Parkinsonism With Pyramidal Degeneration, Supranuclear Gaze Palsy, and Dementia, Mov Disord. 20: 1264-1271.
Wu, J. et al. (2005) Mammalian CHORD-containing protein 1 is a novel heat shock protein 90-interacting protein, FEBS Lett. 579: 421-426.
Zhang, Y. et al. (2005) Transcriptional Analysis of Multiple Brain Regions in Parkinson's Disease Supports the Involvement of Specific Protein Processing, Energy Metabolism, and Signaling Pathways, and Suggests Novel Disease Mechanisms, Am J Med Genet B Neuropsychiatr Genet. 137B: 5-16.
Zimprich, A. et al. (2004) Mutations in LRRK2 Cause Autosomal-Dominant Parkinsonism with Pleomorphic Pathology, Neuron. 44: 601-607.

Papapetropoulos, S. et al. (2006), Multiregional gene expression profiling identifies MRPS6 as a possible candidate gene for Parkinson's Disease. Gene Expression 13:205-215.
Carim et al. (1999), Cloning, expression and mapping of PDCD9, the human homologue of Gallus gallus pro-apoptotic protein p52. Cytogenet Cell Genet 87:85-88.
Umapathy, N.S. et al. (2005) Expression and Function of Glutamine Transporters SN1 (SNAT3) and SN2 (SNAT5) in Retinal Muller Cells, Investigative Ophthalmology & Visual Science. 46 (11): 3980-3987.
Bonifati, V. et al. (2003) Mutations in the DJ-1 Gene Associated with Autosomal Recessive Early-Onset Parkinsonism, Science. 299: 256-259.
Farrer, M.J. (2006) Genetics of Parkinson disease: paradigm shifts and future prospects, Nat Rev Genet. 7: 306-318.
Grunblatt, E. et al. (2004) Gene expression profiling of parkinsonian substantia nigra pars compacta; alterations in ubiquitin-proteasome, heat shock protein, iron and oxidative stress regulated proteins, cell adhesion/cellular matrix and vesicle trafficking genes, J Neural Transm. 111: 1543-1573.
Mandel, S. et al. (2005) Gene Expression Profiling of Sporadic Parkinson's Disease Substantia Nigra Pars Compacta Reveals Impairment of Ubiquitin-Proteasome Subunits, SKP1A, Aldehyde Dehydrogenase, and Chaperone HSC-70, Ann NY Acad Sci. 1053: 356-375.
Moran, L.B. et al. (2006) Whole genome expression profiling of the medial and lateral substantia nigra in Parkinson's disease, Neurogenetics. 7: 1-11.
O'Brien, T.W. et al. (2005) Nuclear MRP genes and mitochondrial disease, Gene. 354: 147-151.
Ogden, C.A. et al. (2004) Candidate genes, pathways and mechanisms for bipolar (manic-depressive) and related disorders: an expanded convergent functional genomics approach, Mol Psychiatry. 9: 1007-1029.
Valente, E.M. et al. (2004) Hereditary Early-Onset Parkinson's Disease Caused by Mutations in PINK1, Science. 304: 1158-1160.
Vernon, A.C. et al. (2005) Neuroprotective effects of metabotropic glutamate receptor ligands in a 6-hydroxydopamine rodent model of Parkinson's disease, Eur J Neurosci. 22: 1799-1806.
Bentley, C.A. et al. (2000) p75 Is Important for Axon Growth and Schwann Cell Migration during Development, The Journal of Neuroscience. 20 (20): 7706-7715.

(Continued)

*Primary Examiner* — James Martinell
(74) *Attorney, Agent, or Firm* — Novak Druce + Quigg, LLP

(57) ABSTRACT

The present invention identifies the changes in gene expression associated with Parkinson's Disease by examining multiregional gene expression from normal brain and brain of Parkinson's Disease. The present also identifies the changes in gene expression associated with Parkinson's Disease by examining the expression of genes from normal blood and from the blood of patients with Parkinson's Disease. In another aspect, the present invention identifies expression profiles which serve as useful diagnostic markers as well as markers that can be used to monitor disease states, disease progression, drug toxicity, drug efficacy and drug metabolism.

27 Claims, 6 Drawing Sheets

OTHER PUBLICATIONS

Blochl, A. et al. (1996) Neurotrophins Stimulate the Release of Dopamine from Rat Mesencephalic Neurons via Trk and p75 Lntr Receptors, The Journal of Biological Chemistry. 271 (35): 21100-21107.

Brann, A.B. et al. (1999) Ceramide Signaling Downstream of the p75 Neurotrophin Receptor Mediates the Effects of Nerve Growth Factor on Outgrowth of Cultured Hippocampal Neurons, The Journal of Neuroscience. 19 (19): 8199-8206.

Ghandi, S. et al. (2005) Molecular pathogenesis of Parkinson's disease, Human Molecular Genetics. 14 (18): 2749-2755.

Hauser, M.A. et al. (2005) Expression Profiling of Substansia Nigra in Parkinson Disease, Progressive Supranuclear Palsy, and Frontotemporal Dementia With Parkinsonism, Arch Neurol. 62: 917-921.

Higuchi, H. et al. (2003) PKA phoshorylates the p75 receptor and regulates its localization to lipid rafts, The EMBO Journal. 22 (8): 1790-1800.

Hughes, A.J. et al. (1992) Accuracy of clinical diagnosis of idiopathic Parkinson's disease: a clinico-pathological study of 100 cases, Journal of Neurology, Neurosurgery, and Psychiatry. 55: 181-184.

Kissil, J.L. et al. (1995) Isolation of DAP3, a Novel Mediator of Interferon-$\gamma$-induced Cell Death, The Journal of Biological Chemistry. 270 (46): 27932-27936.

Kissil, J.L. et al. (1999) Structure-function analysis of an evolutionary conserved protein, DAP3, which mediates TNF-$\alpha$- and Fas-induced cell death, The EMBO Journal. 18 (2): 353-362.

Maraganore, D.M. et al. (2005) High-Resolution Whole-Genome Association Study of Parkinson Disease, Am. J. Hum. Genet. 77: 685-693.

SEQUENCE LISTING

<160> NUMBER OF SEQ ID NOS: 31

<210> SEQ ID NO 1
<211> LENGTH: 940
<212> TYPE: DNA
<213> ORGANISM: Homo sapiens

<400> SEQUENCE: 1

| | | | | | |
|---|---|---|---|---|---|
| gggagccgtc | cggcgcagca | gtttctaggt | ccccactgtc | cccgccgtcc | cgccccttcg | 60 |
| cgtcccggga | accggctggc | ttccgagccg | cactcgccga | tcctccaggc | atgccccgct | 120 |
| acgagctggc | tttaatcctg | aaagccatgc | agcggccaga | gactgctgct | actttgaaac | 180 |
| gtacgataga | ggccctgatg | gacagaggag | caatagtgag | ggacttggaa | acctgggtg  | 240 |
| aacgagcgct | tccttatagg | atctctgccc | acagtcagca | gcacaacaga | ggcgggtatt | 300 |
| tcttggtgga | tttttatgca | cccaccgcag | ctgttgaaag | catggtggag | cacttgtctc | 360 |
| gagatataga | tgtgattaga | gggaatattg | tcaaacaccc | tctgacccag | gaactaaaag | 420 |
| aatgtgaagg | gattgtccca | gtcccactcg | cagaaaaatt | atattccaca | aagaagagga | 480 |
| agaagtgaga | agattcgcca | gattttagcc | ttatatgtaa | ttccttcaca | tttgggcagc | 540 |
| atggacgaga | aggaagaatt | tgcaagtttg | gcctttatat | aagcatgtgt | tgcaggtgct | 600 |
| gtttgatttt | tctaaggtat | ttttagccct | tgatccccct | tgcttgcgag | aggtggggaa | 660 |
| ctgctcactg | acagcttctc | tgtaacctgc | agtaccagtg | gatcgttctt | gatttttgtt | 720 |
| tcattagtgt | catttctttg | tcattgagga | cttttcccct | tacaacagta | acaccatttt | 780 |
| ttgaagagca | aaacttataa | tacctcctgg | gattgtgagc | tagtcattca | gcctgtgtaa | 840 |
| ccatgtggaa | ataaaaattg | acgaccaatg | tattatatgg | acaacttttg | ctttgagtaa | 900 |
| taaacttgat | tgtaggaatg | tgaaaaaaaa | aaaaaaaaa  |            |            | 940 |

<210> SEQ ID NO 2
<211> LENGTH: 948
<212> TYPE: DNA
<213> ORGANISM: Homo sapiens

<400> SEQUENCE: 2

| | | | | | |
|---|---|---|---|---|---|
| ctgggagccg | tccggcgcag | cagtttctag | gtccccactg | tccccgccgt | cccgcccctt | 60 |
| cgcgtcccgg | gaaccggctg | gcttccgagc | cgcactcgcc | gatcctccag | gcatgccccg | 120 |
| ctacgagctg | gctttaatcc | tgaaagccat | gcagcggcca | gagactgctg | ctactttgaa | 180 |
| acgtacgata | gaggccctga | tggacagagg | agcaatagtg | agggacttgg | aaacctggg  | 240 |
| tgaacgagcg | cttccttata | ggatctctgc | ccacagtcag | cagcacaaca | gaggcgggta | 300 |
| tttcttggtg | gattttatg  | cacccaccgc | agctgttgaa | agcatggtgg | agcacttgtc | 360 |
| tcgagatata | gatgtgatta | gagggaatat | tgtcaaacac | cctctgaccc | aggaactaaa | 420 |
| agaatgtgaa | gggattgtcc | cagtcccact | cgcagaaaaa | ttatattcca | caagaagag  | 480 |
| gaagaagtga | gaagattcgc | cagattttag | ccttatatgt | aattccttca | catttgggca | 540 |
| gcatggacga | gaaggaagaa | tttgcaagtt | tggcctttat | ataagcatgt | gttgcaggtg | 600 |
| ctgtttgatt | tttctaaggt | attttttagcc | cttgatcccc | tttgcttgcg | agaggtgggg | 660 |
| aactgctcac | tgacagcttc | tctgtaacct | gcagtaccag | tggatcattc | ttgattttgt | 720 |
| tttcattagt | gtcatttctt | tgtcattgag | gacttttccc | cttacaacag | taacaccatt | 780 |
| ttttgaagag | caaaacttat | aatacctcct | gggattgtga | gctagtcatt | cagcctgtgt | 840 |

```
aaccatgtgg aaataaaaat tgacgaccaa tgtattatat ggacaacttt tgctttgagt    900
aataaacttg attgtaggga aaaaaaaaaa aaaaaaaaa aaaaaaaa                  948
```

<210> SEQ ID NO 3
<211> LENGTH: 942
<212> TYPE: DNA
<213> ORGANISM: Homo sapiens

<400> SEQUENCE: 3

```
ctgggagccg tccggcgcag cagtttctag gtccccactg tccccgccgt cccgccctt     60 cgcgtcccgg gaaccggctg gcttccgagc cgcactcgcc gatcctccag gcatgccccg   120
ctacgagctg gctttaatcc tgaaagccat gcagcggcca gagactgctg ctactttgaa   180
acgtacgata gaggccctga tggacagagg agcaatagtg agggacttgg aaaacctggg   240
tgaacgagcg cttccttata ggatctctgc ccacagtcag cagcacaaca gaggcgggta   300
tttcttggtg gatttttatg cacccaccgc agctgttgaa agcatggtgg agcacttgtc   360
tcgagatata gatgtgatta gagggaatat tgtcaaacac cctctgaccc aggaactaaa   420
agaatgtgaa gggattgtcc cagtcccact cgcagaaaaa ttatattcca caaagaagag   480
gaagaagtga aagattcgc cagatttag ccttatatgt aattccttca catttgggca    540
gcatggacga aaggaagaa tttgcaagtt tggcctttat ataagcatgt gttgcaggtg    600
ctgtttgatt tttctaaggt atttttagcc cttgatcccc tttgcttgcg agaggtgggg   660
aactgctcac tgacagcttc tctgtaacct gcagtaccag tggatcattc ttgattttgt   720
tttcattagt gtcatttctt tgtcattgag acttttccc cttacaacag taacaccatt    780
ttttgaagag caaaacttat aatacctcct gggattgtga gctagtcatt cagcctgtgt   840
aaccatgtgg aaataaaaat tgacgaccaa tgtattatat ggacaacttt tgctttgagt   900
aataaacttg attgtaggaa aaaaaaaaa aaaaaaaaa aa                        942
```

<210> SEQ ID NO 4
<211> LENGTH: 1011
<212> TYPE: DNA
<213> ORGANISM: Homo sapiens

<400> SEQUENCE: 4

```
cggcgtctgc gcagctgcca gcgcctttaa gcccgggctc gcgctctcgg accgtgcttt    60
cgccgcctgg gagccgtccg gcgcagcagt ttctaggtcc ccactgtccc cgccgtcccg   120
ccccttcgcg tccgggaac cggctggctt ccgagccgca ctcgccgatc tccaggcat    180 gccccgctac gagctggctt taatcctgaa agccatgcag cggcagaga ctgctgctac    240 tttgaaacgt acgatagagg ccctgatgga cagaggagca atagtgaggg acttggaaaa   300
cctgggtgaa cgagcgcttc cttataggat ctctgcccac agtcagcagc acaacagagg   360
cgggtatttc ttggtggatt tttatgcacc caccgcagct gttgaaagca tggtggagca   420
cttgtctcga gatatagatg tgattagagg gaatattgtc aaacaccctc tgacccagga   480
actaaaagaa tgtgaaggga ttgtcccagt cccactcgca gaaaaattat attccacaaa   540
gaagaggaag aagtgagaag attcgccaga ttttagcctt atatgtaatt ccttcacatt   600
tgggcagcat ggacgagaag gaagaatttg caagttggc cttatataa gcatgtgttg    660 caggtgctgt ttgatttttc taaggtattt ttagcccttg atccccttg cttgcgagag    720 gtggggaact gctcactgac agcttctctg taacctgcag taccagtgga tcattcttga   780
ttttgttttc attagtgtca tttctttgtc attgaggact tttcccctta caacagtaac   840
```

-continued

| | |
|---|---|
| accattttttt gaagagcaaa acttataata cctcctggga ttgtgagcta gtcattcagc | 900 |
| ctgtgtaacc atgtggaaat aaaaattgac gaccaatgta ttatatggac aactttttgct | 960 |
| ttgagtaata aacttgattg taggaaaaaa aaaaaaaaaa aaaaaaaaaa a | 1011 |

<210> SEQ ID NO 5
<211> LENGTH: 3942
<212> TYPE: DNA
<213> ORGANISM: Homo sapiens

<400> SEQUENCE: 5

| | |
|---|---|
| taattacaga tctacccttta gcacagaagt agccatagac actatgcaga tgtgtgagtt | 60 |
| ggctgtgttc cagttcaact ttatttgcaa atacaggtag caagccagat ttggcccaag | 120 |
| agccctggtt tgccaaccct gctttatggt gaggtaaggt ctatggggcg ttattttgc | 180 |
| tcctccttcc acctttcgtt ttatacttct gggtgttttg aaattaaagt gagatgaatg | 240 |
| tggccattcc agtagtctac agtttgacct tgacatactg aagtcaaaca attttttttt | 300 |
| ttatattttc ctaagttaca ttcttgttag gtagcctttc cccttttga gacagatgta | 360 |
| agaagaaaat gttttttact ttataagctc ttacttcaga agagggtaat gagttttata | 420 |
| ctgtaaacac ttcagttgga acttaaaaga tattgagata tattccttttt taatcaggca | 480 |
| aaactggaat tgaaatttat ttgggtagct aatcagaaaa ctaatcaatc aaatgttttt | 540 |
| ttcctttttt ttttgagtgc aaagctgaga cccgactctt tatttggatg ggctgttcct | 600 |
| ttaccttatc atacgttaat tgatgtaatg ccaggtcaag aaacagcatt ttcagttaaa | 660 |
| tgaaatactg tgctgctgtt aataatgagt cctctgcaga tgtatggcga tgtctttgtg | 720 |
| aactataatg aaatgtgaga agaatgtagt cttcatatga ttagaactgt ctaggaatgt | 780 |
| gtttgataca atcataagga taaattgcct tagacttttt acctactgtt aatgggaaga | 840 |
| gattttggcc tgaattttta ttgtcttcag gaaatttctg ttttatctta aggttggtta | 900 |
| aatatataaa caacgattca gtaggaattt ttaaaatccc taatggactt caatatgaaa | 960 |
| agaaagtaaa gaatgttttt ttctaagcct taagccaata cttagcacat ttcataccat | 1020 |
| tttagcagca cttgtcagaa agaaaatttt aaaaatatag tggattttgt ttggttgcca | 1080 |
| gaatgcacac ttaaacttgt tctgcaattt tctcttcatt tgatccccaa atgaacctct | 1140 |
| ggaaggtagc ctattcttaa gtttcctcct gcactttaaa atcaccctgc ttgcacctct | 1200 |
| tcacgtaggt ctttgaggag atgtgcacct tgtctttgcc aaggtgtgcc tctggcttcc | 1260 |
| tccccgatgg tttccacagc tttccttctc cttgcagcag gcgtttccac ttaatagctg | 1320 |
| ccctgtcagc atctctctag agatcccatc ccaaatctgt aaaccttctt ggctttttttt | 1380 |
| ttttatgaag ataaaatatg taacaataag cactgagacc atatagtagt tatccagtaa | 1440 |
| atcatagctg tcatcgttgt tgctatttta gaaatcctac attttatcgt cttgcatggt | 1500 |
| ccgctccttt ttgactacca acttgcccat gtgttttctc ctaaaacacg ttgctcaagt | 1560 |
| tgcttgtccc tggagccctg gcattttctc ctcctcacca ttgttctcat acctctacca | 1620 |
| tgggaacctt ggcagcctgc tttctggccc cgtcttgcca aatgcccatg tagctaccac | 1680 |
| accgcggctt tttcttgatc tctgtcctct acccccattgt cattctggac aaggcagtct | 1740 |
| cccgattttc cttgtcctat ttgatgatac gtttttatatt tgcttctctg actttgagtc | 1800 |
| ctcttgttag cccctaaatg tttgtactcc ccaaggttct gctggtgatc tccttttcctc | 1860 |
| tccccctcca ccctttctat tgatctcacc tccttctcag gcttcagaga gccgtctgtg | 1920 |
| caggtgacta tgaaatgtgt atttctcatc cacctgcttt gagcttaaga tttacatctg | 1980 |

```
gagaggtcaa cctaggggag ccatggcatc tgagactcag cgtgtcttaa accagattca    2040
tctcttactg tcctcaccag cttctccagc tctccttta gctgtagtga cagttgcact     2100
ctctcagcca ccagattgtg gtgcccttct tcgccacatc ttgccttcat tctccacatt    2160
gcattcgttg cagttttcag gcttatcctt ataaagtatc ttttcttcca aaaattgctt    2220
gtgtatacat atgcatagag agatatctgg aaagaaattc accagaaagt taattcacc    2280 atccagtcta tctctgggta atgggattct atattgttca agctttttt tttttttttt    2340 aaataacagg ccttgattac tcatggactt gtgcccagtg tatcccgtc tatctcctca    2400 gcactccctt gccctgaacc ccatcactgg ggctcagttg ctggttcatt cattctttgt   2460
acctccggtc atcattttcc gggtgccttt caagtaaact ttccttagtg aaacccttct    2520
tccagctgaa tgtttcttcc tttcgtgagc cctctggtct ctatgctatt tcctgtattc    2580
tgccctctgc tctccataca tgtgtatttt tgttctgtc ctttattaga ttgtaagctc     2640
catgagggca gagtttgggt ctgattaccc atcctttccc ccttttggtt acagtctccc    2700 agttttttctt tgggagacaa caccttttcc ccctggctac agttttggtg ggatgggcag   2760
ttcaggtgtc ctgccaacga gatactcttc tcctggaatt tgaattttga gtcatgggat    2820
acaaggactg acagtgattg gcactgattc agcctggccg aggtgctctg aagaagccac    2880
tcattagttc ctgcctccca gatccctgga gctgccctgg tccctgaact ctccgaagcc    2940
tggttcttca gatattcctc gtatctgtga gctatctcat atccttacaa taaattctct    3000
ctctctttta ttttaagtta accaaaaacca gcttctgttg cttttaccca gcgattccta   3060
ccagtagagc tgttatgatt ggaactgagc agacttaatc attctagctc ttatattaat    3120
tctgatgctt tttttttcttt tcttaaaaa cacaaacaaa aacagccaga gactgctgct   3180
actttgaaac gtacgataga ggccctgatg gacagaggag caatagtgag ggacttggaa    3240
aacctgggtg aacgagcgct tccttatagg atctctgccc acagtcagca gcacaacaga    3300
ggcgggtatt tcttggtgga ttttttatgca cccaccgcag ctgttgaaag catggtggag    3360
cacttgtctc gagatataga tgtgattaga gggaatattg tcaaacaccc tctgacccag    3420
gaactaaaag aatgtgaagg gattgtccca gtcccactcg cagaaaaatt atattccaca    3480
aagaagagga agaagtgaga agattcgcca gattttagcc ttatatgtaa ttccttcaca    3540
tttgggcagc atggacgaga aggaagaatt gcaagtttg gcctttatat aagcatgtgt     3600
tgcaggtgct gtttgatttt tctaaggtat ttttagccct tgatcccctt tgcttgcgag    3660
aggtggggaa ctgctcactg acagcttctc tgtaacctgc agtaccagtg gatcgttctt    3720
gattttgttt tcattagtgt catttcttg tcattgagga cttttccct tacaacagta      3780 acaccatttt ttgaagagca aaacttataa tacctcctgg gattgtgagc tagtcattca    3840
gcctgtgtaa ccatgtggaa ataaaaattg acgaccaatg tattatatgg acaacttttg    3900
ctttgagtaa taaacttgat tgtaggaaaa aaaaaaaaaa aa                       3942

<210> SEQ ID NO 6
<211> LENGTH: 438
<212> TYPE: DNA
<213> ORGANISM: Homo sapiens

<400> SEQUENCE: 6
atgcctgaac ctgctaagtc cgctcctgcc ccaaagaagg gctccaagaa ggcggtgact       60
aaggctcaga gaaggacgg gaagaagcgc aagcgcagcc gcaaggagag ctattcagtg       120
tatgtgtaca aggtgctgaa gcaggtccat cccgacaccg gcatctcttc caaggcaatg      180
```

| | |
|---|---:|
| gggatcatga attccttcgt caacgacatc ttcgagcgca tcgcaggcga ggcttcccgc | 240 |
| ctggcgcatt acaacaagcg ctcgaccatc acctccaggg agatccagac ggccgtgcgc | 300 |
| ctgctgcttc cgggggagct ggccaagcac gccgtgtcgg agggcaccaa ggccgtcacc | 360 |
| aagtacacca gttccaagta actttgccaa gtaagcatct ttacacctaa tcccaaaggc | 420 |
| tcttttaaga gccaccca | 438 |

<210> SEQ ID NO 7
<211> LENGTH: 814
<212> TYPE: DNA
<213> ORGANISM: Homo sapiens

<400> SEQUENCE: 7

| | |
|---|---:|
| cagtgttcta actattaacg ctacgatgcc tgaacctacc aagtctgctc ctgccccaaa | 60 |
| gaagggctcc aagaaggcgg tgactaaggc tcagaagaag gacgggaaga agcgcaagcg | 120 |
| cagccgcaag gagagctatt cagtgtatgt gtacaaggtg ctgaagcagg tccatcccga | 180 |
| caccggcatc tcttccaagg caatggggat catgaattcc ttcgtcaacg acatcttcga | 240 |
| gcgcatcgca ggcgaggctt cccgcctggc gcattacaac aagcgctcga ccatcacctc | 300 |
| cagggagatc cagacggccg tgcgcctgct gcttccgggg gagctggcca agcacgccgt | 360 |
| gtcggagggc accaaggccg tcaccaagta caccagttcc aagtaacttt gccaagggag | 420 |
| agacatgaag acagaggaga atgaatgca taaaataact gataatatga atctatacat | 480 |
| agaacttagg aagtctcatc tgcctgaaaa tgactgtgtg gatcccaccc aaatccaact | 540 |
| catcctggtt tgctgcacac tggttcatca aaagaaggtt accgagggga aggaactaaa | 600 |
| ggtgttgca cttcatgtta cttttgagt ttataaacat aaaaacagaa tttacttctg | 660 |
| ttacagacct agttactggg aattcattac ttgccatgga ctacctttgc taagaaaagt | 720 |
| ctgaatgaga agatggcagg acgtctgaaa aaaaagtta taattaataa aatctgcgga | 780 |
| gaattgtaaa aaaaaaaaa aaaaaaaaa aaaa | 814 |

<210> SEQ ID NO 8
<211> LENGTH: 1399
<212> TYPE: DNA
<213> ORGANISM: Homo sapiens

<400> SEQUENCE: 8

| | |
|---|---:|
| gctcctccga gctcgctgtt cgtccgggtt ttttacgttt taatttccag gacttgaact | 60 |
| gccatgtcct ctgaagaagg aaagctcttc gtgggagggc tcaactttaa caccgacgag | 120 |
| caggcactgg aagaccactt cagcagtttc ggacctatct ctgaggtggt cgttgtcaag | 180 |
| gaccgggaga ctcagcggtc caggggtttt ggtttcatca ccttcaccaa cccagagcat | 240 |
| gcttcagttg ccatgagagc catgaacgga gagtctctgg atggtcgtca gatccgtgtg | 300 |
| gatcatgcag gcaagtctgc tcggggaacc agaggaggtg gctttgggc ccatgggcgt | 360 |
| ggtcgcagct actctagagg tggtgggac cagggctatg ggagtggcag gtattatgac | 420 |
| agtcgacctg gagggtatgg atatggatat ggacgttcca gagactataa tgcagaaac | 480 |
| cagggtggtt atgaccgcta ctcaggagga aattacagag acaattatga caactgaaat | 540 |
| gagacatgca cataatatag atacacaagg aataattct gatccaggat cgtccttcca | 600 |
| aatggctgta tttataaagg tttttggagc tgcactgaag catcttattt tatagtatat | 660 |
| caacctttg tttttaaatt gacctgccaa ggtagctgaa gacctttag acagttccat | 720 |
| cttttttttt aaatttttc tgcctattta aagacaaatt atgggacgtt tgtagaacct | 780 |

| | | | | |
|---|---|---|---|---|
| gagtattttt | cttttacca | gttttttagt | ttgagctctt | aggtttattg gagctagcaa | 840 |
| taattggttc | tggcaagttt | ggccagactg | acttcaaaaa | attaatgtgt atccagggac | 900 |
| attttaaaaa | cctgtacaca | gtgtttattg | tggttaggaa | gcaatttccc aatgtaccta | 960 |
| taagaaatgt | gcatcaagcc | agcctgacca | acatggtgaa | accccatctg tactaaacat | 1020 |
| aaaaaaatta | gcctggcatg | gtggtgtacg | cctgtaatcc | cagtgacttg ggaggctgag | 1080 |
| gcaggagaat | cgcttgaacc | cgggaggcgg | aggttgcagt | gagctaagat cgcgccactg | 1140 |
| tactccagcc | tgggcaacag | cgagactcca | tctcaaaaaa | aaggaaatg tgtatcaaga | 1200 |
| acatgattat | ccaggggtat | tttctaattc | agatcatcaa | actgattata tagaagagtt | 1260 |
| ggctttaaaa | tgtttgcaaa | tgtctttttt | tttttaatac | tggaagaaaa aatattctgt | 1320 |
| tgtgtctcat | acagtgctta | ggatgtcttt | cacagagctt | attaaaaaga tgaaacctga | 1380 |
| aaaaaaaaaa | aaaaaaaaa | | | | 1399 |

<210> SEQ ID NO 9
<211> LENGTH: 4861
<212> TYPE: DNA
<213> ORGANISM: Homo sapiens

<400> SEQUENCE: 9

| | | | | |
|---|---|---|---|---|
| cgacgccgcc | gccttagaac | gccttccag | tactgctagc | agcagcccga ccacgcgtta | 60 |
| ccgcacgctc | gcgcctttcc | cttgacacgg | cggacgccgg | aggattgggg cggcaatttg | 120 |
| tcttttcctt | ttttattaaa | attattttc | ctgcctgttg | ttggatttgg ggaaatttt | 180 |
| tgtttgtttt | ttatgatttg | tatttgactg | agagaaaccc | actgaagacg tctgcgtgag | 240 |
| aatagagacc | accgaggccg | actcgcgggc | cgctgcaccc | accgccaagg acaaaaggag | 300 |
| cccagcgcta | ctagctgcac | ccgattcctc | ccagtgctta | gcatgaagaa ggccgaaatg | 360 |
| ggacgattca | gtatttcccc | ggatgaagac | agcagcagct | acagttccaa cagcgacttc | 420 |
| aactactcct | accccaccaa | gcaagctgct | ctgaaaagcc | attatgcaga tgtagatcct | 480 |
| gaaaaccaga | acttttttact | tgaatcgaat | ttggggaaga | gaagtatga acagaatttt | 540 |
| catccaggta | ctacttcctt | tggaatgtca | gtatttaatc | tgagcaatgc gattgtgggc | 600 |
| agtggaatcc | ttgggctttc | ttatgccatg | gctaatactg | gaattgctct ttttataatt | 660 |
| ctcttgacat | ttgtgtcaat | attttccctg | tattctgttc | atctccttt gaagactgcc | 720 |
| aatgaaggag | ggtctttatt | atatgaacaa | ttgggatata | aggcatttgg attagttgga | 780 |
| aagcttgcag | catctggatc | aattacaatg | cagaacattg | gagctatgtc aagctacctc | 840 |
| ttcatagtga | aatatgagtt | gcctttggtg | atccaggcat | taacgaacat tgaagataaa | 900 |
| actgattgt | ggtatctgaa | cgggaactat | ttggttctgt | tggtgtcatt ggtggtcatt | 960 |
| cttcctttgt | cgctgtttag | aaatttagga | tatttgggat | ataccagtgg cctttccttg | 1020 |
| ttgtgtatgt | tgttctttct | gattgtggtc | atttgcaaga | aatttcaggt tccgtgtcct | 1080 |
| gtggaagctg | ctttgataat | taacgaaaca | ataaacacca | ccttaacaca gccaacagct | 1140 |
| cttgtacctg | ctttgtcaca | taacgtgact | gaaaatgact | cttgcagacc tcactatttt | 1200 |
| atttttcaact | cacagactgt | ctatgctgtg | ccaattctga | tcttttcatt tgtctgtcat | 1260 |
| cctgctgttc | ttcccatcta | tgaagaactg | aaagaccgca | gccgtagaag aatgatgaat | 1320 |
| gtgtccaaga | tttcatttt | tgctatgttt | ctcatgtatc | tgcttgccgc cctctttgga | 1380 |
| tacctaacat | tttacgaaca | tgttgagtca | gaattgcttc | atacctactc ttctatcttg | 1440 |
| ggaactgata | ttcttcttct | cattgtccgt | ctggctgtgt | taatggctgt gacccctgaca | 1500 |

-continued

```
gtaccagtag ttattttccc aatccggagt tctgtaactc acttgttgtg tgcatcaaaa      1560
gatttcagtt ggtggcgtca tagtctcatt acagtgtcta tcttggcatt taccaattta      1620
cttgtcatct ttgtcccaac tattagggat atctttggtt ttattggtgc atctgcagct      1680
tctatgttga tttttattct tccttctgcc ttctatatca agttggtgaa gaaagaacct      1740
atgaaatctg tacaaaagat tggggctttg ttcttcctgt taagtggtgt actggtgatg      1800
accggaagca tggccttgat tgttttggat tgggtacaca atgcacctgg aggtggccat      1860
taattggcac cactcaaact caaactcagt ccatctgatg ccagtgttga gtaaactcaa      1920
ctactatgaa atttcaccta atgttttcag tttcacttcc ttttgaagtg cagattcctc      1980
gctggttctt ctgagtgcag aataagtgaa cttttttgtt ttgttttgtt ttttaagaa      2040 acttatctgt atgttagaaa tggatatgaa caacaaaacc acgagtctcg ggttaaggga      2100
agtgacaatt ttattccatt ccagagaatg gacaaactct taacttttat caagccacat      2160
gcttggctgt gtcattgttt aacttggata ttttatgatt ttacttgaat gtgcctaatg      2220
gaaccatttg atgtgagaaa caattctttt taatttacag caaaatattg aataaccatt      2280
gacaaaaaca ctattatttt ttgtaccaaa aatacttaaa gacctcagaa gcactctttt      2340
acttttaaga aattgctttt ttgaacttta ttcagaagca gttatcaata aattccataa      2400
aataatgtca ttggtattta aaaatgaata ttaatataat gaaatggttt gccttttgt       2460 aggcataata agccaaatac tttttaccc aaaataattt ttagagaaaa tgatgtaatg      2520
aaaaattgta ccatgaatta ggagcatagt ttttccatt taaacgtcac cattacttaa      2580
aagatgattg attattgcta taccaaatca gatgaactct gttcatcact tttcttctct      2640
gtccccaaac aatttggttc attcagactg aaatgtttgt gtcttcaact tattagaatg      2700
gaagataatg cagatatttc tgtgggaaat aaaataacta attttgaggt accaaatagt      2760
gcaattgggt aaaacagggt ttattcagtt gcatctgtct ccagtgttgt attgacagct      2820 ctgggtctt ttttgggcca gcccttttt gacattgctt ccagcagtgg aaaatgggca      2880
tttgatggca ataggccaaa attattgtgt ccagagagta cacttttca aaatgctcac      2940 ctactggaag tgtgaattac ttgacaatgt atggcttagt tgtgttcatg ttttgtctac      3000
agtagaggtc taatccacag gttacaccta tgtttgatat gatataagtt ctctttgcgt      3060
aggccactgg gtttctcatg cagtaagctt tataaaaact catttgcact ggactgtcat      3120
ctcattcttg tacaacgtag aattacttgt ttacatccaa caaatggtta gctagggaaa      3180
acagtgcaaa ctgagtgtta gtagtcattt tggtccaact gcatgtcaac ccttccattt      3240
caatcccagt tagaaatgaa aataattact ttgaaacttg gctttaagag cacatttatc      3300
gtacgtcaca gtgtatggtg aatatattat taaataatgt ggtacttcgc tcatcaggca      3360
taatgtctaa aatctaatat acataattcc attaagtggt tgaaggaagc aaataatgga      3420
attgtcaatt ggtcatctgg ctgtaaggtt tgcccttgaa ctaaaaatgt tgtttggggc      3480
aagggccaga atgtggaga catggttttt gttacgcatt cttgtattat atgtgactaa      3540
atttacaaac aagatacatg tgtaattaaa gaccctatg gaactggaag acgtcttgta      3600
gtgctacatt gggtgaaacc gttggtccat ttttgtctgt ttctatgaag ataaaataat      3660
tgggggccat ctagaaatag aaaggcagtg ggaagacaga ttctacggca ctgctttcat      3720
ttaattgggc tttaggcact ccattcgaat gcagaacctc acctctagtt gagaccaaga      3780
attggcaaat ttgcatgagc tcctggaaag agttgctgac tttgtatcta agacctgcca      3840
gggaatacca agagttgttt ctacagactt ttttttttt ttgtatggga gaagatactg      3900
```

| | |
|---|---|
| tggcaaccag gaaggaatgg aaaaaaaatt cttttctcta cagcaaatta atgtgaggaa | 3960 |
| gctcctccaa tcctctggct atttaaggtt caaaatcaag tgcctaggga aaattccaat | 4020 |
| ggatgatttt ctgggagcta tcttgtctac cttgaggttc ctgaacaatg aattcccatt | 4080 |
| aatgagcagt cttcagtatt aaaaccactg tcttgtcacc tcattttgca ttactgtctt | 4140 |
| ccgtggatgt ttcagttaca actgtaatgt tatttataga acaacattaa tccattaaag | 4200 |
| ctaacctatt tttcaatatt tatgataatc tatgtacata tattgtctgt ccatatgtat | 4260 |
| ttgtaaatag gttgtatata atgtcaggtt tgggtcttgg gttcaagtgt atatattcct | 4320 |
| gtaagtttct taactgcatt ttgatgaatt cacattatgt aactataaga attgtcccaa | 4380 |
| aagtacctgt acagaaaatt gaatattgaa aaattgacaa attgtgtaca acactaaaa | 4440 |
| aaaacttgtt taaattgtat ttgcaataaa caacatcaaa tttttcatg aaatcttggt | 4500 |
| acaaattcag atctcttatt taaaatttaa ataaggaata cattttcaaa atgcagtaat | 4560 |
| caaaatgtga tctagtgtaa tgaaataaaa tgtgatctag tgtaatggaa gacctttgag | 4620 |
| aacctgggtg tattaacttt gtgtatatag tgtaaatatc cccactgtac tgttagaggc | 4680 |
| caacaattct agtatggctt gttggcaaag agtgctacac cgtttcaatg aaacaatgta | 4740 |
| tgtttgtttt aactgaacta aaataaatac atgcttaatc ctgaaaaaaa aaaaaaaaaa | 4800 |
| aaaaaaaaaa aaaaaaaaaa aaaaaaaaaa aaaaaaaaaa aaaaaaaaaa aaaaaaaaaa | 4860 |
| a | 4861 |

<210> SEQ ID NO 10
<211> LENGTH: 1381
<212> TYPE: DNA
<213> ORGANISM: Homo sapiens

<400> SEQUENCE: 10

| | |
|---|---|
| catctggctg taaggtttgc ccttgaacta aaaatgttgt ttggggcaag ggccagaaat | 60 |
| gtggagacat ggttttgtt acgcattctt gtattatatg tgactaaatt tacaaacaag | 120 |
| atacatgtgt aattaaagac ccttatggaa ctggaagacg tcttgtagtg ctacattggg | 180 |
| tgaaaccgtt ggtccatttt tgtctgtttc tatgaagata aaataattgg gggccatcta | 240 |
| gaaatagaaa ggcagtggga agacagattc tacggcactg ctttcattta attgggcttt | 300 |
| aggcactcca ttcgaatgca gaacctcacc tctagttgag accaagaatt ggcaaatttg | 360 |
| catgagctcc tggaaagagt tgctgacttt gtatctaaga cctgccaggg aataccaaga | 420 |
| gttgttccta cagactttt tttttttttt tgtatgggag aagatactgt ggcaaccagg | 480 |
| aaggaatgga aaaaaaattc ttttctctac agcaaattaa tgtgaggaag ctcctccaat | 540 |
| cctctggcta tttaaggttc aaaatcaagt gcctaggaa aattccaatg gatgattttc | 600 |
| tgggagctat cttgtctacc ttgaggttcc tgaacaatga attcccatta atgagcagtc | 660 |
| ttcagtatta aaaccactgt cttgtcacct cattttgcat tactgtcttc cgtggatgtt | 720 |
| tcagttacaa ctgtaatgtt atttatagaa caacattaat ccattaaagc taacctattt | 780 |
| ttcaatattt atgataatct atgtacatat attgtctgtc catatgtatt tgtaaatagg | 840 |
| ttgtatataa tgtcaggttt gggtcttggg ttcaagtgta tatattcctg taagtttctt | 900 |
| aactgcattt tgatgaattc acattatgta actataagaa ttgtcccaaa agtacctgta | 960 |
| cagaaaattg aatattgaaa aattgacaaa ttgtgtacaa acactaaaaa aaacttgttt | 1020 |
| aaattgtatt tgcaataaac aacatcaaat ttttcatga aatcttggta caaattcaga | 1080 |
| tctcttattt aaaatttaaa taaggaatac attttcaaaa tgcagtaatc aaaatgtgat | 1140 |

| | |
|---|---|
| ctagtgtaat gaaataaaat gtgatctagt gtaatggaag acctttgaga acctgggtgt | 1200 |
| attaactttg tgtatatagt gtaaatatcc ccactgtact gttagaggcc aacaattcta | 1260 |
| gtatggcttg ttggcaaaga gtgctacacc gtttcaatga aacaatgtat gtttgtttta | 1320 |
| actgaactaa aataaataca tgcttaatcc cgaaaaaaaa aaaacaaaa aaaaaaaaaa | 1380 |
| a | 1381 |

<210> SEQ ID NO 11
<211> LENGTH: 1423
<212> TYPE: DNA
<213> ORGANISM: Homo sapiens

<400> SEQUENCE: 11

| | |
|---|---|
| gggatgaaat actggagctg ttgtagaaga aaaacttctg attttaatac attcttagcc | 60 |
| caagagggct gtacaaaagg gaaacacatg tggactaaaa aagatgctgg gaaaaaagtt | 120 |
| gttccatgta gacatgactg gcatcagact ggaggtgaag ttaccatttc agtatatgct | 180 |
| aaaaactcac ttccagaact tagccgagta gaagcaaata gcacattgtt aaatgtgcat | 240 |
| attgtatttg aaggagagaa ggaatttgat caaaatgtga attatggggg tgtgattgat | 300 |
| gtaaagcgaa gttatgtaac tatgactgca acaaagattg aaatcactat gagaaaagct | 360 |
| gaaccgatgc agtgggcaag ccttgaactg cctgcagcta aaaagcagga aaaacaaaaa | 420 |
| gatgccacaa cagattgagt gggagatgga aggaaggcta ttacattatt tccgaattt | 480 |
| taatactgtg tgaagtggtg gcttgctgct gtaatctttt gttttgttgt tgtgttactg | 540 |
| aatgtggcat ttcagggtta acattaggtt cttaaaagcc aaagtcagtt tgtctttttg | 600 |
| tgcctctcat ctttcttttg tgttatgtaa gattgattat tcatttctcc ctactggtag | 660 |
| gaaccatagt tgtgtcctat acttgaagag gctggaaagt agcccataac cataattgca | 720 |
| gtatttcttt gtatttctct gttaagcaaa gaaatattaa ggaacatttt ttttatgttt | 780 |
| ttgtattatt ccataattag taaagcaaga tgaaatgtca aatttttaatc agttttttca | 840 |
| tggatttgtg ttcttacagt acttgaaaat atttaaggaa gagatgaagc tctgcagttt | 900 |
| tttctatgtg ggatgattac ttttttaagg aggattaatt ctgaggtagt atagtaacta | 960 |
| aaggggaata tatgaattgt ttaacaaatt agaatttgtt tacaactact tgaattttta | 1020 |
| aattatgtca aaacttacat tacttgccaa gcagtatgat gttataggaa acataaataa | 1080 |
| gattacagag gtatcaattt ggttaaaatt caccatttta taagactaag caataatctt | 1140 |
| aacaacctct ttcctgaata tttaaatgtg tttgtatggt gttatgacta attgttactg | 1200 |
| atttagagac taagccctct taaaacctt agttaaatat aaaagaaat tatatatatc | 1260 |
| ttgcctccct gatggaaaac tatataaat tgtagactta aaaggtttgt ggaaatacat | 1320 |
| taggatatca gaaaactaaa tatatggagt tgctttatga ctattacatg ttaaataaaa | 1380 |
| atagcttaat tgtaaaaaaa aaaaaaaaaa aaaaaaaaa aaa | 1423 |

<210> SEQ ID NO 12
<211> LENGTH: 1325
<212> TYPE: DNA
<213> ORGANISM: Homo sapiens

<400> SEQUENCE: 12

| | |
|---|---|
| ggtcgttgtg gtgcgctgtc ttcccgcttg cgtcagggac ctgcccgact cagtggccgc | 60 |
| catggcatca gatgaaggca aacttttgt tggagggctg agttttgaca ccaatgagca | 120 |
| gtcgctggag caggtcttct caaagtacgg acagatctct gaagtggtgg ttgtgaaaga | 180 |

-continued

| | |
|---|---|
| cagggagacc cagagatctc ggggatttgg gtttgtcacc tttgagaaca ttgacgacgc | 240 |
| taaggatgcc atgatggcca tgaatgggaa gtctgtagat ggacggcaga tccgagtaga | 300 |
| ccagcaggc aagtcgtcag acaaccgatc ccgtgggtac cgtggtggct ctgccggggg | 360 |
| ccggggcttc ttccgtgggg gccgaggacg gggccgtggg ttctctagag gaggagggga | 420 |
| ccgaggctat ggggggaacc ggttcgagtc caggagtggg ggctacggag gctccagaga | 480 |
| ctactatagc agccggagtc agagtggtgg ctacagtgac cggagctcgg gcgggtccta | 540 |
| cagagacagt tatgacagtt acgctacaca acgagtaa aaacccttcc tgctcaagat | 600 |
| cgtccttcca atggctgtgt gtttaaagat tgtgggagct cgctgaacg ttaatgtgta | 660 |
| gtaaatgcac ctccttgtat tcccactttc gtagtcattt cggttctgat cttgtcaaac | 720 |
| ccagcctgac cgcttctgac gccgggatgg cctcgttact agacttttct ttttaaggaa | 780 |
| gtgctgtttt tttttgaggg ttttcaaaac attttgaaaa gcatttactt ttttgaccac | 840 |
| gagccatgag ttttcaaaaa aatcggggt tgtgtgggtt tttggttttt gttttagttt | 900 |
| ttggttgcgt tgcctttttt tttttagtgg ggttggcccc atgaagtggg tgccccactc | 960 |
| acttctctga gatcgaacgg actgtgaatc cgctctttgt cggaagctga gcaagctgtg | 1020 |
| gctttttcc aactccgtgt gacgtttctg agtgtagtgt ggtaggaccc cggcgggtgt | 1080 |
| ggcagcaact gccctggagc cccagccccct gcgtccatct gtgctgtgcg ccccacagta | 1140 |
| gacgtgcaga cgtccctgag aggttcttga agatgtttat ttatattgtc ctttttact | 1200 |
| ggaagacgta cgcatactcc atcgatgttg tatttgcagt ggctgaggaa ttcttgtacg | 1260 |
| cagttttctt tggctttacg aagccgatta aagaccgtg tgaaatgaaa aaaaaaaaa | 1320 |
| aaaaa | 1325 |

<210> SEQ ID NO 13
<211> LENGTH: 1330
<212> TYPE: DNA
<213> ORGANISM: Homo sapiens

<400> SEQUENCE: 13

| | |
|---|---|
| gctcgggtcg ttgtggtgcg ctgtcttccc gcttgcgtca gggacctgcc cgactcagtg | 60 |
| gccgccatgg catcagatga aggcaaactt tttgttggag ggctgagttt tgacaccaat | 120 |
| gagcagtcgc tggagcaggt cttctcaaag tacggacaga tctctgaagt ggtggttgtg | 180 |
| aaagacaggg agacccagag atctcgggga tttgggtttg tcacctttga gaacattgac | 240 |
| gacgctaagg atgccatgat ggccatgaat gggaagtctg tagatggacg gcagatccga | 300 |
| gtagaccagg caggcaagtc gtcagacaac cgatcccgtg gtaccgtgg tggctctgcc | 360 |
| ggggccgggg cttcttccg tggggccga ggacggggcc gtgggttctc tagaggagga | 420 |
| ggggaccgag gctatggggg gaaccggttc gagtccagga gtggggggcta cggaggctcc | 480 |
| agagactact atagcagccg gagtcagagt ggtggctaca gtgaccggag ctcgggcggg | 540 |
| tcctacagag acagttacga cagttacgct acacacaacg agtaaaaacc cttcctgctc | 600 |
| aagatcgtcc ttccaatggc tgtgtgttta aagattgtgg gagcttcgct gaacgttaat | 660 |
| gtgtagtaaa tgcacctcct tgtattccca ctttcgtagt catttcggtt ctgatcttgt | 720 |
| caaacccagc ctgaccgctt ctgacgccgg gatggcctcg ttactagact tttcttttta | 780 |
| aggaagtgct gtttttttt gagggtttc aaaacatttt gaaaagcatt tactttttg | 840 |
| accacgagcc atgagtttc aaaaaaatcg ggggttgtgt gggttttgg ttttgtttt | 900 |
| agttttggt tgcgttgcct tttttttt agtggggttg gccccatgaa gtgggtgccc | 960 |

| | |
|---|---:|
| cactcacttc tctgagatcg aacggactgt gaatccgctc tttgtcggaa gctgagcaag | 1020 |
| ctgtggcttt tttccaactc cgtgtgacgt ttctgagtgt agtgtggtag acccccggcg | 1080 |
| ggtgtggcag caactgccct ggagcccag ccctgcgtc catctgtgct gtgcgcccca | 1140 |
| cagtagacgt gcagacgtcc ctgagaggtt cttgaagatg tttatttata ttgtcctttt | 1200 |
| ttactggaag acgtacgcat actccatcga tgttgtattt gcagtggctg aggaattctt | 1260 |
| gtacgcagtt ttctttggct ttacgaagcc gattaaaaga ccgtgtgaaa tgaaaaaaaa | 1320 |
| aaaaaaaaaa | 1330 |

<210> SEQ ID NO 14
<211> LENGTH: 1322
<212> TYPE: DNA
<213> ORGANISM: Homo sapiens

<400> SEQUENCE: 14

| | |
|---|---:|
| tagcttggca cgaggctcgg gtcgttgtgg tgcgctgtct tcccgcttgc gtcagggacc | 60 |
| tgcccgactc agtggccgcc atggcatcag atgaaggcaa acttttttgtt ggagggctga | 120 |
| gttttgacac caatgagcag tcgctggagc aggtcttctc aaagtacgga cagatctctg | 180 |
| aagtggtggt tgtgaaagac agggagaccc agagatctcg gggatttggg tttgtcacct | 240 |
| ttgagaacat tgacgacgct aaggatgcca tgatggccat gaatgggaag tctgtagatg | 300 |
| gacggcagat ccgagtagac caggcaggca agtcgtcaga caaccgatcc cgtgggtacc | 360 |
| gtggtggctc tgccggggc cgggcttct ccgtgggg ccgaggacgg ggccgtgggt | 420 |
| tctctagagg aggagggac cgaggctatg gggggaaccg gttcgagtcc aggagtgggg | 480 |
| gctacgagg ctccagagac tactatagca gccggagtca gagtggtggc tacagtgacc | 540 |
| ggagctcggg cgggtcctac agagacagtt acgacagtta cgctacacac aacgagtaaa | 600 |
| aacccttcct gctcaagatc gtccttccaa tggctgtgtg tttaaagatt gtgggagctt | 660 |
| cgctgaacgt taatgtgtag taaatgcacc tccttgtatt cccactttcg tagtcatttc | 720 |
| ggttctgatc ttgtcaaacc cagcctgacc gcttctgacg ccgggatggc ctcgttacta | 780 |
| gacttttctt tttaaggaag tgctgttttt ttttgagggt tttcaaaaca ttttgaaaag | 840 |
| catttacttt tttgaccacg agccatgagt tttcaaaaaa atcggggtt gtgtgggttt | 900 |
| ttggtttttg ttttagtttt tggttgcgtt gccttttttt tttagtgggg ttggccccat | 960 |
| gaagtgggtg ccccactcac ttctctgaga tcgaacggac tgtgaatccg ctctttgtcg | 1020 |
| gaagctgagc aagctgtggc ttttttccaa ctccgtgtga cgtttctgag tgtagtgtgg | 1080 |
| taggacccgg cgggtgtgca gcaactgccc tggagcccca gccctgcgt ccatctgtgc | 1140 |
| tgtgcgcccc acagtagacg tgcagacgtc cctgagaggt tcttgaagat gtttatttat | 1200 |
| attgtccttt tttactggaa gacgtacgca tactccatcg atgttgtatt tgcagtggct | 1260 |
| gaggaattct tgtacgcagt ttctttggc tttacgagcc gattaaaaga ccgtgtgaaa | 1320 |
| tg | 1322 |

<210> SEQ ID NO 15
<211> LENGTH: 3905
<212> TYPE: DNA
<213> ORGANISM: Homo sapiens

<400> SEQUENCE: 15

| | |
|---|---:|
| atccgaggct ggcgggtttc ggcagtagct gtggctgcgg ctgccgggcc tggggacgcg | 60 |
| ggcggccgag gccgccgtcg cagcctcctc gtctcgccgg ctatggctgc gctcggccgg | 120 |

```
cccttcagcg gcctccctct gagcggcggc tcggacttcc tgcagccgcc gcagccggcc    180
ttccccggcc gggccttccc gccgggggct gacggcgccg agttggcccc gcggccggga    240
cctcgcgcag tccctagcag tcccgctggg agtgcggcgc gcggacgtgt ttctgttcac    300 tgtaaaaga aacacaagcg agaggaggag gaggatgatg attgtccagt aagaaagaaa     360
aggataactg aagcagagct ctgtgctggt cctaatgact ggattccttg tgcacatcag    420
gatgtagagg ggcatggagt aaatcccagt gttagtggcc tttccatacc tgggatatta    480
gatgttattt gtgaagaaat ggatcagaca actggagaac cacagtgtga agttgcccga    540
aggaagcttc aggagattga ggacaggata attgatgaag atgaagaagt tgaagctgac    600
agaaatgtta accatctccc cagtcttgtc ctttctgata ccatgaaaac aggtttgaag    660
agggaatttg atgaagtttt tacaaagaaa atgattgagt ctatgagccg tccttccatg    720
gagcttgttc tctggaaacc cctccctgaa ctcctttctg ataagccaaa gccatcctct    780
aatactaaga actatacagg agagagccaa gctaagcatg tagctgctgg cactgccttc    840
cctcagagaa ctgaactgtt ttcggaacct cggccaacag ggatgtctct ttataatagt    900
ttggagacag ctactagcac agaagaagag atggaactct agaaaccaat ttctacacta    960
aagttgtcaa atgttagaag aatcctgtgt tcagttatga gactctttgc atagtatagg   1020
gacttgaagg ttttatgaga cgggtgtaat aatatctcca cctgtgattt gggggtggga   1080
ctcttatttt gggtagccat ttattgactt cacctttttg ccaaggaagt ttgtctcaag   1140
ggaaaagcag ttttctgtgg ggcttattaa aggaatgttg gtttacattg tcttcaaaga   1200
caagtataga agctgtatgt gtaagggtga cttaaatcat atgtcacatt gtctaaacta   1260
ttcagacact tggagaatat tctccttgaa ttaaaaaaga tgattaagaa ggatgctcct   1320
acaactgtat cctgacagtt aagtcacagc ttaatgtgta gatatgagct gtttacagtg   1380
gtgactatat ataattgggg agaagaaggg aagagagcag cagtagctta agcctgttgc   1440
taagaaattt aatttcttag caacttgtaa tttagttatc aattcaatat agctctgttg   1500
attaaatagc cgatagtatt gtggctctcc tctttgacta tgaaaatata gagaaagttt   1560 tttcttttaag gcttttttgc cttgtgccac tgttgctcct tggtttccct tgcgtaattg   1620
ataagcccag ttattcagta atgtttacaa attaattgac tttgatagtt aaaagattat   1680
gaggtaaccc atctgcaatt tgcctgtggg agaagcatcc tttagttcat cttaaggaag   1740
tgctttatca gctaaaccca gcattgataa cttttggtaat tttttttaaaa agttatactt   1800 gtattagcaa gttttttttt ttttccccca ccgcaacctc catctcccgg gttcaagcaa    1860
ttctcctgcc tcaccctccc aagtagctgg gattacaggt gcccacctcc acgcccagct   1920 aattttttgta tttttaatag accggtttt tgccatgttg gccaggctgg tctcgaactc    1980
ctgacctcag gtgatctgcc cacccccagcc tcccaaaatg ctgggattac aggcgtgagc   2040
cacggcacgc agccagcaag ttgttttttaa atgttaatat agaaaacagt gaaggattag    2100
ctgaaaatat atgagcaggt gacattgagg tttactgaaa tagccaattt gactggtgct   2160
tagactattg tgcagtaaac ctaaaaggta gtggagaatt gcttcctgct agcaggaagc   2220
cttcatcttc ttgagtaccc aaaccaggct tcaggtgtcc tttgaggata gccaggtttg   2280
aaatttttag tttctcagga agagctcttc tatgtggcag gggctgatag gcaaaataa    2340 aatgacaatt tctttattgc tacagagtat cctctataag ttattaaacg agtgtaatgg   2400
tataatgccc ttccatcaca caacaggaca ccaccccagt tttgttttct gggtttcttc   2460 ccccttttgta ggaatcagat accttttgta gaaaaaaatg gcttatgcca cgtaaaggtg   2520
```

```
aatttttaga aaccaccttc taggcgtttt tggaacccctt actgaaatcc ctccccttgt    2580
tacagatggc gtagaagtca caagtctgtt aattggactg ttgcttcttt gcctgttcct    2640
gctttctctt tctgtctgga tagtcaggaa aagatttaat gtttaatatt taaacaaaat    2700
atttaatgtc tatacagtaa aattattcaa acttcaaacc agtattgaaa gcagttggaa    2760
accagctaat agtttcttaa tctcagattt cgagatgaat gtaaactgta ttcttttgaa    2820
atgtgcaagt gtttgattca tgccatttga taaacttctg ccttgtagtc attgtttgat    2880
gggaccaact tgtaaagtat gagccttaaa taaatctcca tgctgaaaaa tgtgttctaa    2940
tgcaacacaa aaacatgaag tgactgccca gaggtagagt tagtgtttag gtggaaaggg    3000
agatgacagc tttccaaaga aggacctaaa acacaccaag attgtcttct acaggaattg    3060
ctgggcaggt ctccgactaa aggtcttatg atgaaaagga agaaacaagc ccccaacaca    3120
aggctctgat actactggta aatgtaggag agaattaaga atctgttaat taaaatccaa    3180
acagagctta tttcagtagt caagttacct gacatgataa ttatttctgc aggataattg    3240
atgttttatg ttctttttttg gactttatct tcttgcaaaa atttctacaa aaattgtttt    3300
cttcatcctt gtggtgctta ttcatctgag ccgtctccac agtcccaatg cctctgcttt    3360
ttgttttact tttgtagcat aaggttttttg cttttgcttt gccttaagag ttccctaggg    3420
agttaccagg gcttttcgtt ttgtgtagct tttgcagcat ggatcaaaca ttggcttact    3480
gtgctaatgt gtgaagagaa aaaattctct aaagcaggtg agctttaatg aacaaatgtg    3540
tattttatct gagtttgagt agggtgcgtt gtggattttg tttttgggt ttttttttt     3600 ttttgtaatt atatgaagaa agtccagttc tcataaatat tgatcactta aaaaacttac    3660
tctttcttga aaaggtacac atgtaaaatt taggaaaata actaaagtag gggctggaac    3720
cataagaatg tttatccgca cgttcattta ttattttgga tttggaactt ggctttgttt    3780
ttcaatagtg acaagaatgg ttcagttcta ggaatgttct ggaagatgct gttaatttta    3840 cttttaaaatg agaatctggt gttactgtat tttatcgttt tcaataaaac ttcttaagtg    3900
ttttg                                                                3905
```

<210> SEQ ID NO 16
<211> LENGTH: 1633
<212> TYPE: DNA
<213> ORGANISM: Homo sapiens

<400> SEQUENCE: 16

```
gccgcctgag ccgcggacgg tttgctgagc ccgttagtgc gcccggccga gacacgccgc      60
cgccatgtcc cgctacctgc gtccccccaa cacgtctctg ttcgtcagga acgtggccga    120
cgacaccagg tctgaagact gcggcgtga atttggtcgt tatggtccta tagttgatgt    180
gtatgttcca cttgatttct acactcgccg tccaagagga tttgcttatg ttcaatttga    240
ggatgttcgt gatgctgaag acgctttaca taatttggac agaaagtgga tttgtggacg    300
gcagattgaa atacagtttg cccagggggaa tcgaaagaca ccaaatcaga tgaaagccaa    360
ggaagggagg aatgtgtaca gttcttcacg ctatgatgat tatgacagat acagacgttc    420
tagaagccga agttatgaaa ggaggagatc aagaagtcgg tcttttgatt acaactatag    480
aagatcgtat agtcctagaa acagtagacc gactggaaga ccacggcgta gcagaagcca    540
ttccgacaat gatagattca aacaccgaaa tcgatctttt tcaagatcta aatccaattc    600
aagatcacgg tccaagtccc agcccaagaa agaaatgaag gctaaatcac gttctaggtc    660
tgcatctcac accaaaacta gaggcacctc taaaacagat tccaaaacac attataagtc    720
```

```
tggctcaaga tatgaaaagg aatcaaggaa aaagaaccca cctagatcca aatctcagtc    780
aagatcacag tctaggtcta ggtcaaaatc tagatcaagg tcttggacta gtcctaagtc    840
cagtggccac tgatagtata aaccatggtc attttaggc atgtatcatt catttactca    900
tagtttggtt tacttaaatt atcaggaata caatgttgca atgatgctta aaaaacactt    960
gttagttttc cctgtaccag gcaatggtta taattaaaat gatatgctgt tgagaagcca   1020
ctcttaagag tccagtttgt ttaatgttat gggcagctac caatttgtgg tgtctctgta   1080 tattttgta  aagattctca tttttatgc  ttgaagtatt tggtgaaaag atgttggttg   1140
accataattt gcaacattgt ctcattaaaa ataaactttc atattcatat ttggtagaac   1200
tgttaaccta gaaatgtagc ttgctaataa gatagaatga tacaaaagtg aagcagtagc   1260
cacagtacaa cactgactgc tcagacacat ttaggttcag ggtggacctt tatgtcttgt   1320
caagatgtct aggcccggct gggcgtggtg gctcacacct gtaatcccag cactttggga   1380
ggccgaggcg ggcggatcac gaggtcagga gttcgagacc agcctgacca acacggtgaa   1440
accccgtctc tactaaaaat acaaaaatta tccgggcatg gtggcacatg cctgtaatct   1500
cagctactca ggaggctgag gcaagagaat cgcttgaacc tgggaggtag aagttgcagt   1560
gagccaaaat cacgccactg cactccagcc tgggcaacag agtgagactc cgtctcaaaa   1620
aaaaaaaaaa aaa                                                      1633

<210> SEQ ID NO 17
<211> LENGTH: 874
<212> TYPE: DNA
<213> ORGANISM: Homo sapiens

<400> SEQUENCE: 17
gtagcagagc cctctagctg tgtgtgtctg aggctcggcc gcctgagccg cggacggttt     60
gctgagcccg ttagtgcgcc cggccgagac acgccgccgc catgtcccgc tacctgcgtc    120
cccccaacac gtctctgttc gtcaggaacg tggccgacga caccaggtct gaagacttgc    180
ggcgtgaatt tggtcgttat ggtcctatag ttgatgtgta tgttccactt gatttctaca    240
ctcgccgtcc aagaggattt gcttatgttc aatttgagga tgttcgtgat gctgaagacg    300
ctttacataa tttggacaga aagtggattt gtggacggca gattgaaata cagtttgccc    360
agggggatcg aaagacacca aatcagatga agccaaggca agggaggaat gtgtacagtt    420
cttcacgcta tgatgattat gacagataca gacgttctag aagccgaagt tatgaaagga    480
ggagatcaag aagtcggtct tttgattaca actatagaag atcgtatagt cctagaaaca    540
gtagaccgac tggaagacca cggcgtagca gaagccattc cgacaatgat agaccaaact    600
gcagctggaa tacccagtac agttctgctt actacacttc aagaaagatc tgaaagcgga    660
aaaagaacca agaagggca gttcaagcga ccaaagggtg ggtggaaggt gctgcagtat    720
gaatactgta cgaatatttt gactctggtc tgaaaagata aagaatgtt atcgaaaact    780 acatggaata attgaagtcc cttcaagttt gaaagtaagc attttaggac aaataaaagg    840
aaattcaact ttgtaaaaaa aaaaaaaaa aaaa                                874

<210> SEQ ID NO 18
<211> LENGTH: 4897
<212> TYPE: DNA
<213> ORGANISM: Homo sapiens

<400> SEQUENCE: 18
gaggctcggc cgcctgagcc gcggacggtt tgctgagccc gttagtgcgc ccggccgaga     60
```

```
cacgccgccg ccatgtcccg ctacctgcgt cccccaaca cgtctctgtt cgtcaggaac    120
gtggccgacg acaccaggtc tgaagacttg cggcgtgaat ttggtcgtta tggtcctata    180
gttgatgtgt atgttccact tgatttctac actcgccgtc aagaggatt tgcttatgtt    240 caatatcctt tcttcagatg gctgattagt gaggggtgtt gaagtttgaa attcaagttt    300
atagaatgta aagctgtaca gttatggcga ccccaaagag aaagcatgaa agaacctta    360 gagtagagtt caacacttaa ggcaagtaga caagccaaag acctcttaag gatcaggctt    420
gaagagaagg gagagtttgg gaaaagaaaa aataaagaaa agctggaaga aggacaagcc    480
taatgggaga caaagcctcg ctttatctac aaaagggga aaaggttgtt tttcaaagtt    540
aaagataaag ccatctgtca tatttggcca agcatctcat gacaagtcct tctgacaagc    600
acttaaagag ttaaaggtca agatgaagtt gaatgatggc caagattaaa ggagtcatac    660
ctgatgtatc ctacagaata actattttttc ttttttttt ttttttaat gttttgtaag    720 cagttaattt tcaaaattat tctggtttgg tctagtgaca aaacctgtaa cttgatttat    780
gtgggccttt gatgttgtga ttgtggtctt gtgtaaatgc actctctctt atgaagttaa    840
agtgtaacag gatgtatatt cttaagatta aattcagcat attttggttt tggaccaggt    900
ggtcagatgc cacggagtag caggcagtgc tctttggagt agcgtggggt tctggggtta    960
agccacagag ccctgcttaa aggagagaca ggtgcatgca ctgggactta cttagaaaca    1020
gctctggtgg tcttgtaggg tcagaaccac tagaaatttt gtttatatat agatttaaa    1080 gtggttgctg gggacacata taaacccta acttctttaa cttagccctg tgaagactgc    1140
tggccctgcg ctgctttagc acaatgatca gttggccctg aatgagttgc agaaggcctt    1200
ctccctggta taggtaccta actgggacct atgggagact ggtccctgac ccagagttc    1260 aggtgacctt acttccgttc cttcagtga gatcatctcc ctgcaacaag ggtttgggtt    1320
gtggacctca gactaggaaa agttcttcct gcttaaattc agtgagcctc aaactttaa    1380 gttagtggag tcctagtgag acttagggaa aagccaaaaa ctactcctgc agggccagtg    1440
atcaaggaca gttgtgagaa ttggttgcaa agctccatta cagagaaaat aatagctata    1500
tctggcttag taaataaagg tagcagtgcg ttctggctta caacatagac ctcattttac    1560
ctagtgttgg gtggccgagg aatcaaggtc agtagtagtt tgattcaaga gtgtgtgata    1620
tttgaggcaa aaaaggctag taattcaaag caatctaaag gagaatgata attttaaaat    1680
acatattcag taagtctatg gttttaaaat agttgaaaag aaataagtaa caggcttatg    1740
aatttcattt ttgaaaagac cataaagtac aaatttctcc atgactgaca tcagagtgat    1800
actcggctgc ctctgctgct gctgtctctt ctgtctgact ccattcgcaa tagccttttc    1860
ttcctatccc tggcttaccg agtaaagtag aaacttgcca tcagcccagg attctgtttt    1920
cgagggtagc cccagagagg atgctctgtt ctcattaata attttttacag ctctcaatat    1980 aaatccttt tatacttatt atattctgtc tcttgggta acaaagtagt gtacccatta    2040
agtgaacgta ttccttctaa ttagtttaga gcccagctgc attaaccttg agggatgttc    2100
agttacagta ttcaaggttc tgaactcccc atcagccttt ccctttcat gttgaaagcc    2160 cagttattta gaatttgtcc ttccatttaa tctgttcata atggcctcgg gaagacagag    2220
ctggaaacct gcagtcctta attcctttca gaacaaaaag tgggaagtct agtaaggcag    2280 acctttagt ctctataata aaagaatacc agtatcggtc tcaaaaaagg agtgtgtcac    2340
ttcagggata ttttaaatca cctctaaatc tgcagtcttg tgttgtctct caaatttagg    2400
aaaaagaaat gtgcaaacta gaatggggat ttttgggata gaatgaaaac ctataccgt    2460
```

| | |
|---|---|
| acctaaccta gctctctttc caaaccattt atatcaaaca ctgtcttgaa tgtgtacttg | 2520 |
| gcctctgtta aaatgatggt tttaggaaag gagctaggtt tggacagaat agctatataa | 2580 |
| agccagcagt tctcgtagta ttattgctga catgaccagg gaggacaagc agcttagctt | 2640 |
| ctcagatcaa aaacaagtac cagtagttcc tgcttaaggc tggtaaataa tatcttgaaa | 2700 |
| ttctcaagtt ggaaaccagt ctcaaaccca tttctttgca agaagttgta tatttagggt | 2760 |
| catggttagg gctttccagt ctaggagtcc ttccagtggg ctgtttcttg atagcatgct | 2820 |
| tttacagtct gcatggatgt aataacgctt ttggtatagt gattgtcttg agtactgctt | 2880 |
| gactctggtc ttgatgccca caaatggcta gcgtgcttgt cttcccatgc agtggaagga | 2940 |
| agacagttaa atgaaatagt agtattagat atatatgaaa aagaaaacag caaaataaat | 3000 |
| ttgaagttaa tgctttcgtc tcttgtaagg taaggcatat actgcttgct tacacaagaa | 3060 |
| ctattggcat tttctttttt tcgtttgaaa caaatatgaa aaatagtatt ttggttttaa | 3120 |
| gaaattttta ttttagcata caacatataa ctgacatttg ttttttcttt tttgtcttgt | 3180 |
| aaacttaatt cttaaaactt aggaaaattt ttggatagga caacttggtg attcagctat | 3240 |
| aacagatctt atttcaataa taactttact gcaatatgta ttcatacatt ttcaaatgtg | 3300 |
| tgccttagga aatcacaagt gcttttatag tgtgaagtgt taatggctga atccaactga | 3360 |
| atcaccaact agtaagtggg gttctggttg atgttctgga ataatattgg gagattgtga | 3420 |
| attgttccag ataccaac tgaactttca ttcattatca aagtttgcaa aacttcccaa | 3480 |
| gccccttaac atttagcaca tttgaggatg ttcgtgatgc tgaagacgct ttacataatt | 3540 |
| tggacagaaa gtggatttgt ggacggcaga ttgaaataca gtttgcccag ggggatcgaa | 3600 |
| agacaccaaa tcagatgaaa gccaaggaag ggaggaatgt gtacagttct tcacgctatg | 3660 |
| atgattatga cagatacaga cgttctagaa gccgaagtta tgaaaggagg agatcaagaa | 3720 |
| gtcggtcttt tgattacaac tatagaagat cgtatagtcc tagaaacagt agaccgactg | 3780 |
| gaagaccacg gcgtagcaga agccattccg acaatgatag attcaaacac cgaaatcgat | 3840 |
| cttttttcaag atctaaatcc aattcaagat cacggtccaa gtcccagccc aagaaagaaa | 3900 |
| tgaaggctaa atcacgttct aggtctgcat ctcacaccaa aactagaggc acctctaaaa | 3960 |
| cagattccaa aacacattat aagtctggct caagatatga aaaggaatca aggaaaaaag | 4020 |
| aaccacctag atccaaatct cagtcaagat cacagtctag gtctaggtca aaatctagat | 4080 |
| caaggtcttg gactagtcct aagtccagtg gccactgata gtataaacca tggtcatttt | 4140 |
| taggcatgta tcattcattt actccatagtt tggtttactt aaattatcag gaatacaatg | 4200 |
| ttgcaatgat gcttaaaaaa cacttgttag ttttccctgt accaggcaat ggttataatt | 4260 |
| aaaatgatat gctgttgaga agccactctt aagagtccag tttgtttaat gttatgggca | 4320 |
| gctaccaatt tgtggtgtct ctgtatattt ttgtaaagat tctcattttt tatgcttgaa | 4380 |
| gtatttggtg aaaagatgtt ggttgaccat aatttgcaac attgtctcat taaaaataaa | 4440 |
| cttcatatt catatttggt agaactgtta acctagaaat gtagcttgct aataagatag | 4500 |
| aatgatacaa aagtgaagta gtagccacag tacaacactg actgctcaga cacatttagg | 4560 |
| ttcagggtgg acctttatgt cttgtcaaga tgtctaggcc cggctgggcg tggtggctca | 4620 |
| cacctgtaat cccagcactt tgggaggctg aggcgggcgg atcacgaggt caggagttcg | 4680 |
| agaccagcct gaccaacacg gtgaaacccc gtctctacta aaaatacaaa aattatccgg | 4740 |
| gcatggtggc acatgcctgt aatctcagct actcaggagg ctgaggcaag agaatcgctt | 4800 |
| gaacctggga ggtagaagtt gcagtgagcc aaaatcacgc cactgcactc cagcctgggc | 4860 |

-continued

| aacagagtga gactccgtcc caaaaaaaaa aaaaaaa | 4897 |

<210> SEQ ID NO 19
<211> LENGTH: 1058
<212> TYPE: DNA
<213> ORGANISM: Homo sapiens

<400> SEQUENCE: 19

| cgcggacggt tgctgagcc cgttagtgcg cccggccgag acacgccgcc gccatgtccc | 60 |
| gctacctgcg tccccccaac acgtctctgt tcgtcaggaa cgtggccgac gacaccaggt | 120 |
| ctgaagactt gcggcgtgaa tttggtcgtt atggtcctat agttgatgtg tatgttccac | 180 |
| ttgatttcta cactcgccgt ccaagaggat ttgcttatgt tcaatttgag gatgttcgtg | 240 |
| atgctgaaga cgctttacat aatttggaca gaaagtggat ttgtggacgg cagattgaaa | 300 |
| tacagtttgc ccagggggat cgaaagacac caaatcagat gaaagccaag gaagggagga | 360 |
| atgtgtacag ttcttcacgc tatgatgatt atgacagata cagacgttct agaagccgaa | 420 |
| gttatgaaag gaggagatca agaagtcggt cttttgatta caactataga agatcgtata | 480 |
| gtcctagaaa cagtagaccg actggaagac acggcgtag cagaagccat tccgacaatg | 540 |
| atagccaagt aagcaagaag aaaaatgaga gataatgctt cagtgagaga ggaaaggtgc | 600 |
| tacatagagt atgagctgtt aagttacaac ccaggggaaa gacctgggaa ctattgtatt | 660 |
| attctcttga aaatttggcc cagtaagctg ctacatccag ttcaactaac aaaatcctgt | 720 |
| ataccacaga gaagaataaa gaaaccaaa ctgacaaaca tccttctttt atttaagacc | 780 |
| aaactgcagc tggaataccc agtacagttc tgcttactac acttcaagaa agatctgaaa | 840 |
| gcggaaaaag aaccaaagaa gggcagttca agcgaccaaa gggtgggtgg aaggtgctgc | 900 |
| agtatgaata ctgtacgaat attttgactc tggtctgaaa agataaaaga atgttatcga | 960 |
| aaactacatg gaataattga agtcccttca agtttgaaag taagcatttt aggacaaata | 1020 |
| aaaggaaatt caactttgta aaaaaaaaa aaaaaaa | 1058 |

<210> SEQ ID NO 20
<211> LENGTH: 4535
<212> TYPE: DNA
<213> ORGANISM: Homo sapiens

<400> SEQUENCE: 20

| agcgggtctg cccgccgccg ccactgctgc tgccaccgcc gtcgccgccg ccgccgccgc | 60 |
| cgccactgct gctgccggtg ctaaggagtt cgctggagcc cttccctcag acccggcccg | 120 |
| gtcttcgcgc ccggactcct ggcgccagcg ctaggcgcac tcaccgctct gacgggtgca | 180 |
| gacgcgggag ttgtcccaga ctgtggagtg gcgggcacgg ccccagctcc ccttccgttc | 240 |
| cctgaccct tcttgccatc gccccagaca tggggaacgc ggcgaccgcc aagaaaggca | 300 |
| gcgaggtgga gagcgtgaaa gagtttctag ccaaagccaa agaagacttt ttgaaaaaat | 360 |
| gggagaatcc aactcagaat aatgccggac ttgaagattt tgaaaggaaa aaaaccttg | 420 |
| gaacaggttc atttggaaga gtcatgttgg taaaacacaa agccactgaa cagtattatg | 480 |
| ccatgaagat cttagataag cagaaggttg ttaaactgaa gcaaatagag catacttga | 540 |
| atgagaaaag aatattacag gcagtgaatt ttccttccct tgttcgactg gagtatgctt | 600 |
| ttaaggataa ttctaattta tacatggtta tggaatatgt ccctgggggt gaaatgtttt | 660 |
| cacatctaag aagaattgga aggttcagtg agcccatgc acggttctat gcagctcaga | 720 |
| tagtgctaac attcgagtac ctcaattcac tagacatcat ctacagagat ctaaaacctg | 780 |

```
aaaatctctt aattgaccat caaggctata tccaggtcac agactttggg tttgccaaaa    840
gagttaaagg cagaacttgg acattatgtg gaactccaga gtatttggct ccagaaataa    900
ttctcagcaa gggctacaat aaggcagtgg attggtgggc attaggagtg ctaatctatg    960
aaatggcagc tggctatccc ccattctttg cagaccaacc aattcagatt tatgaaagaa   1020
ttgtttctgg aaaggtccga ttcccatcca acttcagttc agatctcaag gaccttctac   1080
ggaacctgct gcaggtggat ttgaccaaga gatttggaaa tctaaagaat ggtgtcagtg   1140
atataaaaac tcacaagtgg tttgccacga cagattggat tgctatttac cagaggaagg   1200
ttgaagctcc attcatacca aagtttagag gctctggaga taccagcaac tttgatgact   1260
atgaagaaga agatatccgt gtctctataa cagaaaaatg tgcaaaagaa tttggtgaat   1320
tttaaagagc aacaagatga catctgagct cacactcagt gtttgcactc tgttgagaga   1380
taaggtagag ctgagaccgt ccttgttgaa gcagttacct agttccttca ttccaacgac   1440
tgagtgaggt ctttattgcc atcatcccgt gtgcgcactc tgcatccacc tatgtaacaa   1500
ggcaccgcta agcaagcatt gtctgtgcca taacacagta ctagaccact ttcttacttc   1560
tctttgggtt gtctttctcc tctcctatat ccatttcttc cttttccaat tcattggtt    1620
ttctctaaac agtgctccat tttattttgt tggtgtttca gatgggcagt gttatggcta   1680
cgtgatattt gaagggaagg ataagtgttg cttcagtag ttattgccaa tattgttgtt    1740
ggtcaatggc ttgaagataa actttctaat aattattatt tctttgagta gctcagactt   1800
ggttttgcca aaactcttgg taattttga agatagactg tcttatcacc aaggaaattt    1860
atacaaatta gactaacttt tcttggaatt cactattctg gcaataaatt ttggtagact   1920
aatacagtac agctagaccc agaaatttgg aaggctgtag atcagaggtt ctagttccct   1980
ttccctcctt ttatatcctc ctctccttga gtaatgaagt gaccagcctg tgtagtgtga   2040
caaacgtgtc tcattcagca ggaaaaacta atgatatgga tcatcaccca gattctctca   2100
cttggtacca gcatttctgt aggtattaga gaagagttct aagttttcta aaccttaact   2160
gttccttaag gattttagcc agtattttaa tagaacatga ttaatgaaag tgacaaattt   2220
taaattttct ctaatagtcc tcatcataaa cttttttaaag gaaaataagc aaactaaaaa   2280
gaacattggt ttagataaat acttatactt tgcaaagtca aaaatggctt gattttttgga  2340
aacaatatag aggtattcat atttaaatga gggtttacat ttgttttgtt ttgtaaccgt   2400
taaaaagaag ttgtttccag ctaattattg tggtgtacta tatttgtgag cctagggtag   2460
gggcactgct gcaacttctg ctttcatccc atgcctcatc aatgaggaaa gggaacaaag   2520
tgtataaaac tgccacaatt gtattttaat tttgaggtat gatattttca gatatttcat   2580
aatttctaac ctctgttctc tcagtaaaca gaatgtctga tcgatcatgc agatacaatg   2640
ttggtatttg agaggttagt ttttttccta cacttttttt tgccaactga cttaacaaca   2700
ttgctgtcag gtggaaattt caagcacttt tgcacattta gttcagtgtt tgttgagaat   2760
ccatggctta acccacttgt tttgctattt ttttctttgc ttttaatttt ccccatctga   2820
ttttatctct gcgtttcagt gacctacctt aaaacaacac acgagaagag ttaaactggg   2880
ttcatttaa tgatcaattt acctgcatat aaaatttatt tttaatcaag ctgatcttaa    2940
tgtatataat cattctattt gctttattat cggtgcaggg aggtcattaa caccacttct   3000
tttcatctgt accacaccct ggtgaaacct ttgaagacat aaaaaaaacc tgtctgagat   3060
gttcttttcta ccaatctata tgtctttcgg ttatcaagtg tttctgcatg gtaatgtcat  3120
gtaaatgctg atattgattt cactggtcca tctatattta aaacgtgcaa gaaaaaaata   3180
```

-continued

| | | | | |
|---|---|---|---|---|
| aaatactctg | ctctagcaag | ttttgtgtaa | caaaggcata | tcgtcatgtt | aataaattta | 3240 |
| aaacatcatt | cgtataaaat | attttaattt | tcttgtattt | catttagacc | caagaacatg | 3300 |
| ctgaccaatg | tgttctatat | gtaaactaca | aattctatgg | tagctttgtt | gtatattatt | 3360 |
| gtaaaattat | tttaataagt | catggggatg | acaatttgat | tattacaatt | tagttttcag | 3420 |
| taatcaaaaa | gatttctatg | aattctaaaa | aatatttttt | tctatgaaat | tactagtgcc | 3480 |
| cagctgtaga | atctacctta | ggtagatgat | ccctagacat | acgttggttt | tgagggctat | 3540 |
| tcagccattc | cattttactc | tctatttaaa | ggccgtgagc | aagcttgtca | tgagcaaata | 3600 |
| tgtcaaggga | gtcaatctct | gaccaatcaa | gtacactaaa | ttagaatatt | tttaaagtat | 3660 |
| gtaacattcc | cagtttcagc | cacaatttag | ccaagaataa | gataaaaact | tgaataagaa | 3720 |
| gtaagtagca | taaatcagta | tttaacctaa | aattacatat | ttgaaacaga | agatattatg | 3780 |
| ttatgctcag | taaataatta | agagatggca | ttgtgtaaga | aggagcccta | gactgaaagt | 3840 |
| caagacatct | gaatttcagg | ctggaaaact | atcagtatga | tctcagcctc | agttctcttg | 3900 |
| tctgtaagat | ggaagaactg | gattaggcag | tttgtaagat | tcctcctaac | tttcacagtc | 3960 |
| gatgacaaga | ttgtctttt | atctgatatt | ttgaagggta | tattgctttg | aagtaagtct | 4020 |
| caataaggca | atatatttta | gggcatcttt | cttcttatct | ctgacagtgt | tcttaaaatt | 4080 |
| atttgaatat | cataagagcc | ttggtgtctg | tcctaattcc | tttctcactc | accgatgctg | 4140 |
| aatacccagt | tgaatcaaac | tgtcaaccta | ccaaaaacga | tattgtggct | tatgggtatt | 4200 |
| gctgtctcat | tcttggtata | ttcttgtgtt | aactgcccat | tggcctgaaa | atactcattg | 4260 |
| taagcctgaa | aaaaaaaatc | tttcccactg | ttttttctgc | ttgttgtaag | aatcaaatga | 4320 |
| aataatgtat | gtgaaagcac | cttgtaaact | gtaacctatc | aatgtaaaat | gttaaggtgt | 4380 |
| gttgttatt | cattaattac | ttctttgttt | agaatggaat | ttcctatgca | ctactgtagc | 4440 |
| taggaaatgc | tgaaaacaac | tgtgtttttt | aattaatcaa | taactgcaaa | attaaagtac | 4500 |
| cttcaatgga | taagacaaca | aaaaaaaaaa | aaaaa | | | 4535 |

<210> SEQ ID NO 21
<211> LENGTH: 1951
<212> TYPE: DNA
<213> ORGANISM: Homo sapiens

<400> SEQUENCE: 21

| | | | | | |
|---|---|---|---|---|---|
| gttcgctgga | gccctttcct | cagacccggc | ccggtcttcg | cgcccggact | cctggcgcca | 60 |
| gcgctaggcg | cactcaccgc | tctgacgggt | gcagacgcgg | gagttgtccc | agactgtgga | 120 |
| gtggcgggca | cggccccagc | cccccttccc | ttccctgacc | ccttcttgcc | atcgccccag | 180 |
| acatgggaa | cgcggcgacc | gccaagaaag | gcagcgaggt | ggagagcgtg | aaagagtttc | 240 |
| tagccaaagc | caaagaagac | ttttgaaaa | aatgggagaa | tccaactcag | aataatgccg | 300 |
| gacttgaaga | ttttgaaagg | aaaaaaaccc | ttggaacagg | ttcatttgga | agagtcatgt | 360 |
| tggtaaaaca | caaagccact | gaacagtatt | atgccatgaa | gatcttagat | aagcagaagg | 420 |
| ttgttaaact | gaagcaaata | gagcatactt | tgaatgagaa | aagaatatta | caggcagtga | 480 |
| attttccttt | ccttgttcga | ctggagtatg | cttttaagga | taattctaat | ttatacatgg | 540 |
| ttatggaata | tgtccctggg | ggtgaaatgt | tttcacatct | aagaagaatt | ggaaggttca | 600 |
| gtgagcccca | tgcacggttc | tatgcagctc | agatagtgct | aacattcgag | tacctccatt | 660 |
| cactagacct | catctacaga | gatctaaaac | ctgaaaatct | cttaattgac | catcaaggct | 720 |
| atatccaggt | cacagacttt | gggttgtgcca | aaagagttaa | aggcagaact | tggacattat | 780 |

```
gtggaactcc agagtatttg gctccagaaa taattctcag caagggctac aataaggcag    840
tggattggtg ggcattagga gtgctaatct atgaaatggc agctggctat cccccattct    900
ttgcagacca accaattcag atttatgaaa agattgtttc tggaaagaac ttttgatatg    960
aacaaaacaa aactttgaga aaaattaaca gacaaggcag tgatttattt ttgaagaatt   1020
tgagaagtgt agactctcaa gaggactaaa ggtcatatga agaatgatga gagaaccaaa   1080
atacattaaa atcacaaatg gaagaagaat attttactaa tacaaaaact aagaatgtaa   1140
atgttataat aattgtttca aatcatttaa ttgacagtaa ttataaagtt cttgaatctt   1200
tactatatta cttttatttta tacttcatat aagaaatcca gttttctaac aaggatactg   1260
tcataactaa atttacattt attaagaaaa actgctttag ttaaaattaa tgtgtcttca   1320
tttttatgca ttggcctcga tttgccaatc attctctatt ggttaaaatt tatattcagc   1380
tgtttatgaa tatatattca ttttatatca aactttaaaa ttttgtatct aataatcagc   1440
atatattcta aaatcataac agtctaaatc ctgggcacct tagaagaatg acaccagaaa   1500
accttattat atcacaatat tctgtttttcc ccttcattta tttagaaata tgacaggata   1560
tttggtgtac ttttgttttt taactaaaag taccagattc tctctcccca tgtgggatat   1620
aaaattatcc ccatctctta ctcccttta ctcatctaaag tagaagtcat gaaagtggaa   1680
tttttgccat taaaaggctc tgtattatgt gaagttagat tgtattaacc atttcccaat   1740
aaatcatctg tttcaaaact caaattcaaa ctagaatgtg tctctattca cattgcaaaa   1800
atattattgt ctctctggtt agtggctaaa agccaaattg gaaactaact agttttttaa   1860
attttttaaa ttgtgcaaat tattaaaaat ccaatttggt cttataaaaa aaaaaaaaaa   1920
aaaaaaaaaa aaaaaaaaaa aaaaaaaaaa a                                  1951

<210> SEQ ID NO 22
<211> LENGTH: 2219
<212> TYPE: DNA
<213> ORGANISM: Homo sapiens

<400> SEQUENCE: 22
ctagaagaac tcgaccagtg agcaggcgag gaaggggcgg gagccggggt cccggtagct    60
tctagtaggt tccagaaggc ggcgcgtgcg gttgggaacg cggagcggac ggattcgatt   120
caacggggtt ccggaccgcg ctgcgctatg gagcaggtca atgagctgaa ggagaaaggc   180
aacaaggccc tgagcgtggg taacatcgat gatgccttac agtgctactc cgaagctatt   240
aagctggatc cccacaacca cgtgctgtac agcaaccgtt ctgctgccta tgccaagaaa   300
ggagactacc agaaggctta tgaggatggc tgcaagactg tcgacctaaa gcctgactgg   360
ggcaagggct attcacgaaa agcagcagct ctagagttct taaaccgctt tgaagaagcc   420
aagcgaacct atgaggaggg cttaaaacac gaggcaaata accctcaact gaaagagggt   480
ttacagaata tggaggccag gttggcagag agaaaattca tgaacccttt caacatgcct   540
aatctgtatc agaagttgga gagtgatccc aggacaagga cactactcag tgatcctacc   600
taccgggagc tgatagagca gctacgaaac aagccttctg acctgggcac gaaactacaa   660
gatccccgga tcatgaccac tctcagcgtc ctccttgggg tcgatctggg cagtatggat   720
gaggaggaag agattgcaac acctccacca ccaccccctc ccaaaaagga gaccaagcca   780
gagccaatgg aagaagatct tccagagaat aagaagcagg cactgaaaga aaagagctg   840 gggaacgatg cctacaagaa gaagactttt gacacagcct tgaagcatta cgacaaagcc   900
aaggagctgg accccactaa catgacttac attaccaatc aagcagcggt atactttgaa    960
```

-continued

| | | | | |
|---|---|---|---|---|
| aagggcgact | acaataagtg | ccgggagctt | tgtgagaagg ccattgaagt ggggagagaa | 1020 |
| aaccgagaag | actatcgaca | gattgccaaa | gcatatgctc gaattggcaa ctcctacttc | 1080 |
| aaagaagaaa | agtacaagga | tgccatccat | ttctataaca agtctctggc agagcaccga | 1140 |
| accccagatg | tgctcaagaa | atgccagcag | gcagagaaaa tcctgaagga gcaagagcgg | 1200 |
| ctggcctaca | taaaccccga | cctggctttg | gaggagaaga acaaaggcaa cgagtgtttt | 1260 |
| cagaaagggg | actatcccca | ggccatgaag | cattatacag aagccatcaa aggaacccg | 1320 |
| aaagatgcca | aattatacag | caatcgagct | gcctgctaca ccaaactcct ggagttccag | 1380 |
| ctggcactca | aggactgtga | ggaatgtatc | cagctggagc cgaccttcat caagggttat | 1440 |
| acacggaaag | ccgctgcgct | ggaagcgatg | aaggactaca ccaaagccat ggatgtgtac | 1500 |
| cagaaggcgc | tagacctgga | ctccagctgt | aaggaggcgg cagacggcta ccagcgctgt | 1560 |
| atgatggcgc | agtacaaccg | gcacgacagc | cccgaagatg tgaagcgacg agccatggcc | 1620 |
| gaccctgagg | tgcagcagat | catgagtgac | ccagccatgc gccttatcct ggaacagatg | 1680 |
| cagaaggacc | cccaggcact | cagcgaacac | ttaaagaatc tgtaatagc acagaagatc | 1740 |
| cagaagctga | tggatgtggg | tctgattgca | attcggtgat gacttgttca tcccccttc | 1800 |
| ccttcgccct | catgtggaaa | gaggagctgg | accgcggcg agcagcacgg agcggaaggg | 1860 |
| agagcagggg | agagaaggcc | tcatctctct | atatttatac ataaccccgg ggaagacaca | 1920 |
| gagactcgta | cctgcgctgt | ttgtgccgcc | gctgcctctg ggccctccca gcacacgcat | 1980 |
| ggtctcttca | ccgctgccct | cgagttccat | gtctctttcc cctgcccta gttgctgtct | 2040 |
| cggctgctct | cccatagttg | gttttttttt | tatttggggc agtgggcatg ttatggggag | 2100 |
| gggaggggg | tcttccagcc | tcaggtccca | gctgtctcac gttgtttatt ctgcgtcccc | 2160 |
| ttctccaata | aaacaagcca | gttgggcgtg | gttatatgtt gaaaaaaaaa aaaaaaaaa | 2219 |

<210> SEQ ID NO 23
<211> LENGTH: 2762
<212> TYPE: DNA
<213> ORGANISM: Homo sapiens

<400> SEQUENCE: 23

| | | | | |
|---|---|---|---|---|
| tgggtatgaa | gtggttggga | gaatccaaga | acatggtggt gaatggcagg agaaatggag | 60 |
| gcaagttgtc | taatgaccat | cagcagaatc | aatcaaaatt acagcacacg gggaaggaca | 120 |
| ccctgaaggc | tggcaaaaat | gcagtcgaga | ggaggtcgaa cagatgtaat ggtaactcgg | 180 |
| gatttgaagg | acagagtcgc | tatgtaccat | cctctggaat gtccgccaag gaactctgtg | 240 |
| aaaatgatga | cctagcaacc | agtttggttc | ttgatcccta tttaggtttt caaacacaca | 300 |
| aaatgaatac | tagcgccttt | ccttcgagga | gctcaaggca tttttcaaaa tctgacagtt | 360 |
| tttctcacaa | caaccctgtg | agatttaggc | ctattaaagg aaggcaggaa gaactaaagg | 420 |
| aagtaattga | acgttttaag | aaagatgaac | acttggagaa agccttcaaa tgtttgactt | 480 |
| caggcgaatg | ggcacggcac | tatttctca | acaagaataa aatgcaggag aaattattca | 540 |
| aagaacatgt | atttatttat | ttgcgaatgt | ttgcaactga cagtggattt gaaatattgc | 600 |
| catgtaatag | atactcatca | gaacaaaatg | gagccaaaat agttgcaaca aaagagtgga | 660 |
| aacgaaatga | caaaatagaa | ttactggtgg | gttgtattgc cgaactttca gaaattgagg | 720 |
| agaacatgct | acttagacat | ggagaaaacg | acttcagtgt catgtactcc acaaggaaaa | 780 |
| actgtgctca | actctggctg | ggtcctgctg | cgtttataaa ccatgattgc agacctaatt | 840 |
| gtaagtttgt | gtcaactggt | cgagatacag | catgtgtgaa ggctctaaga gacattgaac | 900 |

```
ctggagaaga aatttcttgt tattatggag atgggttctt tggagaaaat aatgagttct    960
gcgagtgtta cacttgcgaa agacggggca ctggtgcttt taaatccaga gtgggactgc   1020
ctgcgcctgc tcctgttatc aatagcaaat atggactcag agaaacagat aaacgtttaa   1080
ataggcttaa aaagttaggt gacagcagca aaaattcaga cagtcaatct gtcagctcta   1140
acactgatgc agataccact caggaaaaaa acaatgcaac ttctaaccga atcttcagtt   1200
ggcgtaaaaa agaatagcaa gagcagaacg ttaacgaggc aatctatgtc aagaattcca   1260
gcttcttcca actctacctc atctaagcta actcatataa ataattccag ggtaccaaag   1320
aaactgaaga agcctgcaaa gccttttactt tcaaagataa aattgagaaa tcattgcaag   1380
cggctggagc aaaagaatgc ctcaagaaaa ctcgaaatgg gaaacttagt actgaaagag   1440
cctaaagtag ttctgtataa aaatttgccc attaaaaaag ataaggagcc agagggacca   1500
gcccaagccg cagttgccag cgggtgcttg actagacacg cggcgagaga acacagacag   1560
aatcctgtga gaggtgctca ttcgcagggg gagagctcgc cctgcaccta cataactcgg   1620
cggtcagtga ggacaagaac aaatctgaag gaggcctctg acatcaagct tgaaccaaat   1680
acgttgaatg ctataaaag cagtgtgacg gaaccttgcc ccgacagtgg tgaacagctg   1740
cagccagctc ctgtgctgca ggaggaagaa ctggctcatg agactgcaca aaaaggggag   1800
gcaaagtgtc ataagagtga cacaggcatg tccaaaaaga agtcacgaca aggaaaactt   1860
gtgaaacagt ttgcaaaaat agaggaatct actccagtgc acgattctcc tggaaaagac   1920
gacgcggtac cagatttgat gggtccccat tctgaccagg gtgagcacag tggcactgtg   1980
ggcgtgcctg tgagctacac agactgtgct ccttcacccg tcggttgttc agttgtgaca   2040
tcagatagct tcaaaacaaa agacagcttt agaactgcaa aaagtaaaaa gaagaggcga   2100
atcacaaggt atgatgcaca gttaatccta gaaaataact ctgggattcc caaattgact   2160
cttcgtaggc gtcatgatag cagcagcaaa acaaatgacc aagagaatga tggaatgaac   2220
tcttccaaaa taagcatcaa gttaagcaaa gaccatgaca acgataacaa tctctatgta   2280
gcaaagctta ataatggatt taactcagga tcaggcagta gttctacaaa attaaaaatc   2340
cagctaaaac gagatgagga aaataggggg tcttatacag aggggcttca tgaaaatggg   2400
gtgtgctgca gtgatcctct ttctctcttg gagtctcgaa tggaggtgga tgactatagt   2460
cagtatgagg aagaaagtac agatgattcc tcctcttctg agggcgatga agaggaggat   2520
gactatgatg atgactttga agacgatttt attcctcttc ctccagctaa gcgcttgagg   2580
ttaatagttg gaaaagactc tatagatatt gacatttctt caaggagaag agaagatcag   2640
tcttttaaggc ttaatgccta agctcttggt cttaacttga cctgggataa ctactttaaa   2700
gaaataaaaa attccagtca attattcctc aactgaaagt ttagtggcag cacttctatt   2760
gt                                                                 2762
```

<210> SEQ ID NO 24
<211> LENGTH: 2660
<212> TYPE: DNA
<213> ORGANISM: Homo sapiens

<400> SEQUENCE: 24

```
ctggaattat ttttggtgat taattttctg ggggggactg ggacgcgggg cccggcggcg     60
cggccccgca tcgcagcggc cgggcagcgg ggcctgggac gcgccccgag gaggagcggg    120
gcggcgcagg cggagagaac attgaaagta ttctctaagc tatttgaaga gagtgactaa    180
atgcacctgg gtcaggctgt ctgtgggtat gaagtggttg ggagaatcca agaacatggt    240
```

```
ggtgaatggc aggagaaatg gaggcaagtt gtctaatgac catcagcaga atcaatcaaa    300
attacagcac acggggaagg acaccctgaa ggctggcaaa aatgcagtcg agaggaggtc    360
gaacagatgt aatggtaact cgggatttga aggacagagt cgctatgtac catcctctgg    420
aatgtccgcc aaggaactct gtgaaaatga tgacctagca accagtttgg ttcttgatcc    480
ctatttaggt tttcaaacac acaaaatgaa tactagcgcc tttccttcga ggagctcaag    540
gcattttca aaatctgaca gttttctca caacacccct gtgagattta ggcctattaa     600
aggaaggcag gaagaactaa aggaagtaat tgaacgtttt aagaaagatg aacacttgga    660
gaaagccttc aaatgtttga cttcaggcga atgggcacgg cactattttc tcaacaagaa    720
taaaatgcag gagaaattat tcaaagaaca tgtatttatt tatttgcgaa tgtttgcaac    780
tgacagtgga tttgaaatat tgccatgtaa tagatactca tcagaacaaa atggagccaa    840
aatagttgca acaaaagagt ggaaacgaaa tgacaaaata gaattactgg tgggttgtat    900
tgccgaactt tcagaaattg aggagaacat gctacttaga catggagaaa acgacttcag    960
tgtcatgtac tccacaagga aaaactgtgc tcaactctgg ctgggtcctg ctgcgtttat   1020
aaaccatgat tgcagaccta attgtaagtt tgtgtcaact ggtcgagata cagcatgtgt   1080
gaaggctcta agagacattg aacctggaga agaaatttct tgttattatg gagatgggtt   1140
ctttggagaa aataatgagt tctgcgagtg ttacacttgc gaaagacggg gcactggtgc   1200
ttttaaatcc agagtgggac tgcctgcgcc tgctcctgtt atcaatagca aatatggact   1260
cagagaaaca gataaacgtt taaataggct taaaaagtta ggtgacagca gcaaaaattc   1320
agacagtcaa tctgtcagct ctaacactga tgcagatacc actcaggaaa aaacaatgc    1380
aagtaagtaa gggagatttg ataagcatat ctttttaaaag tattttcaca caatttgctt   1440
tataaagtgt gcttcagtag ttttaaactt ttaaatactc agagagactg ggacttgtga   1500
gctttggctg cacttcaagg ctctagacgt gatttgagta gaggcacagt ctgtatccca   1560
tctctaactt cagtaccgtc ctctagacta ttttcttga ataccttggt aactggatat    1620
gagttcttca tcatatcttc caaggtcatc atatgtttta aacattttca aggtgttaga   1680
gactgtgatg atgtcgctaa gtcctgcaag aagacaaaag gactgagtag aattaaatta   1740
gactctatac attccagtgc ctagccagtt tgttagaaaa gatgatggac ttggggaatt   1800
catagcttct ggccttaagg cttccacctt tcattgctt gctgacccttt ttcaaaacga    1860
actgactcag ttcagcagac caccagtacc agactcagaa ttgtgataga ggagcatttt   1920
gaacagtgcc gtattgtgac atgctgtatt ggctactcca gaaagtagga gtaaagatgg   1980
aaaggagaaa gaagcaacct ctgagattcc agtggtgtgt gggggcaaga tctgatggaa   2040
actgaaaaag agaacgaaga ctaaacaaag agaaggaaa gagaagaaac cctaaatggg    2100
caaaggaaag cacatcctgt tgcggagct ttgaaatatt ggaaccattt ctaattgctc    2160
ctgtttttct gggtaacacc agttttctgt agttgccact aaagcagtag actcttgagt   2220
ctcacttgtc tctgagagag acagaagtta gaaagttttg acttggcgat tccgaaagta   2280
tgcctttgtt ggcacttaaa tgtccagtga gacttcttgg caccttagag ccctctgaga   2340
tactgattat tttaggttct ctccctact ttcagatgtt ttcagcccaa cactgggtgc    2400
tctcttccac tacagagaat cctgaagaaa agggaaggtg tttcccatga tggtgaatgt   2460
cactgccatg aattcctgaa tctacctgct gctgggagtc agagtccaag cataacccgt   2520
gtagcataaa agcagcgctg tagccctatt ccagtctttt tcgttaatgt ccagagtgaa   2580
caacaagagt tagtcaatca ttaactgttg actgttgatt ctcataataa atgcagcata   2640
```

```
acgacaaaaa aaaaaaaaaa                                                2660

<210> SEQ ID NO 25
<211> LENGTH: 2771
<212> TYPE: DNA
<213> ORGANISM: Homo sapiens

<400> SEQUENCE: 25
tgggtatgaa gtggttggga gaatccaaga acatggtggt gaatggcagg agaaatggag     60
gcaagttgtc taatgaccat cagcagaatc aatcaaaatt acagcacacg gggaaggaca    120
ccctgaaggc tggcaaaaat gcagtcgaga ggaggtcgaa cagatgtaat ggtaactcgg    180
gatttgaagg acagagtcgc tatgtaccat cctctggaat gtccgccaag gaactctgtg    240
aaaatgatga cctagcaacc agtttggttc ttgatcccta tttaggtttt caaacacaca    300
aaatgaatac tagcgccttt ccttcgagga gctcaaggca ttttttcaaaa tctgacagtt    360 tttctcacaa caaccctgtg agatttaggc ctattaaagg aaggcaggaa gaactaaagg    420
aagtaattga acgttttaag aaagatgaac acttggagaa agccttcaaa tgtttgactt    480
caggcgaatg ggcacggcac tattttctca acaagaataa aatgcaggag aaattattca    540
aagaacatgt atttatttat ttgcgaatgt ttgcaactga cagtggattt gaaatattgc    600
catgtaatag atactcatca gaacaaaatg gagccaaaat agttgcaaca aaagagtgga    660
aacgaaatga caaaatagaa ttactggtgg gttgtattgc cgaactttca gaaattgagg    720
agaacatgct acttagacat ggagaaaacg acttcagtgt catgtactcc acaaggaaaa    780
actgtgctca actctggctg gtcctgctg cgtttataaa ccatgattgc agacctaatt    840
gtaagtttgt gtcaactggt cgagatacag catgtgtgaa ggctctaaga gacattgaac    900
ctggagaaga aatttcttgt tattatggag atgggttctt tggagaaaat aatgagttct    960
gcgagtgtta cacttgcgaa agacgggca ctggtgcttt taaatccaga gtgggactgc   1020
ctgcgcctgc tcctgttatc aatagcaaat atggactcag agaaacagat aaacgtttaa   1080
ataggcttaa aaagtaggt gacagcagca aaaattcaga cagtcaatct gtcagctcta   1140
acactgatgc agataccact caggaaaaaa acaatgcaac ttctaaccga aaatcttcag   1200
ttggcgtaaa aaagaatagc aagagcagaa cgttaacgag gcaatctatg tcaagaattc   1260
cagcttcttc caactctacc tcatctaagc taactcatat aaataattcc agggtaccaa   1320
agaaactgaa gaagcctgca aagcctttac tttcaaagat aaaattgaga aatcattgca   1380
agcggctgga gcaaaagaat gcttcaagaa aactcgaaat gggaaactta gtactgaaag   1440
agcctaaagt agttctgtat aaaaatttgc ccattaaaaa agataaggag ccagagggac   1500
cagcccaagc cgcagttgcc agcgggtgct tgactagaca cgcggcgaga gaacacagac   1560
agaatcctgt gagaggtgct cattcgcagg gggagagctc gccctgcacc tacataactc   1620
ggcggtcagt gaggacaaga acaaatctga aggaggcctc tgacatcaag cttgaaccaa   1680
atacgttgaa tggctataaa agcagtgtga cggaaccttg ccccgacagt ggtgaacagc   1740
tgcagccagc tcctgtgctg caggaggaag aactggctca tgagactgca caaaaagggg   1800
aggcaaagtg tcataagagt gacacaggca tgtccaaaaa gaagtcacga caaggaaaac   1860
ttgtgaaaca gtttgcaaaa atagaggaat ctactccagt gcacgattct cctgaaaaag   1920
acgacgcggt accagatttg atgggtcccc attctgacca gggtgagcac agtggcactg   1980
tgggcgtgcc tgtgagctac acagactgtg ctccttcacc cgtcggttgt tcagttgtga   2040
catcagatag cttcaaaaca aaagacagct ttagaactgc aaaaagtaaa aagaagaggc   2100
```

```
gaatcacaag gtatgatgca cagttaatcc tagaaaataa ctctgggatt cccaaattga    2160
ctcttcgtag gcgtcatgat agcagcagca aaacaaatga ccaagagaat gatggaatga    2220
actcttccaa aataagcatc aagttaagca aagaccatga caacgataac aatctctatg    2280
tagcaaagct taataatgga tttaactcag gatcaggcag tagttctaca aaattaaaaa    2340
tccagctaaa acgagatgag gaaaataggg ggtcttatac agaggggctt catgaaaatg    2400
gggtgtgctg cagtgatcct ctttctctct tggagtctcg aatggaggtg gatgactata    2460
gtcagtatga ggaagaaagt acagatgatt cctcctcttc tgagggcgat gaagaggagg    2520
atgactatga tgatgacttt gaagacgatt ttattcctct tcctccagct aagcgcttga    2580
ggttaatagt tggaaaagac tctatagata ttgacatttc ttcaaggaga agagaagatc    2640
agtctttaag gcttaatgcc taagctcttg gtcttaactt gacctgggat aactacttta    2700
aagaaataaa aaattccagt caattattcc tcaactgaaa gtttagtggc agcacttcta    2760
ttgtcccttc a                                                        2771

<210> SEQ ID NO 26
<211> LENGTH: 2102
<212> TYPE: DNA
<213> ORGANISM: Homo sapiens

<400> SEQUENCE: 26
ttactctcca tttttctctg gaattatttt tggtgattaa ttttctgggg gggactggga      60
cgcggggccc ggcggcgcgg ccccgcatcg cagcggccgg gcagcggggc ctggacgcg     120 ccccgaggag gagcggggcg gcgcaggcgg agagaacatt gaaagtattc tctaagctat    180
ttgaagagag tgactaaatg cacctgggtc aggctgtctg tgggtatgaa gtggttggga    240
gaatccaaga acatggtggt gaatggcagg agaaatggag gcaagttgtc taatgaccat    300
cagcagaatc aatcaaaatt acagcacacg gggaaggaca ccctgaaggc tgcaaaaat    360 gcagttgaga ggaggtcgaa cagatgtaat ggtaactcgg gatttgaagg acagagtcgc    420
tatgtaccat cctctggaat gtccgccaag gaactctgtg aaaatgatga cctagcaacc    480
agtttggttc ttgatcccta tttaggtttt caaacacaca aatgaatac tagcgccttt    540 ccttcgagga gctcaaggca ttttcaaaa tctgacagtt tttctcacaa caaccctgtg    600
agatttaggc ctattaaagg aaggcaggaa gaactaaagg aagtaattga acgttttaag    660
aaagatgaac acttggagaa agccttcaaa tgtttgactt caggcgaatg ggcacggcac    720 tatttttctca acaagaataa aatgcaggag aaattattca agaacatgt atttatttat    780 ttgcgaatgt ttgcaactga cagtggattt gaaatattgc catgtaatag atactcatca    840
gaacaaaatg gagccaaaat agttgcaaca aaagagtgga aacgaaatga caaaatagaa    900
ttactggtgg gttgtattgc cgaactttca gaaattgagg agaacatgct acttagacat    960
ggagaaaacg acttcagtgt catgtactcc acaaggaaaa actgtgctca actctggctg   1020
ggtcctgctg cgtttataaa ccatgattgc agacctaatt gtaagtttgt gtcaactggt   1080
cgagatacag catgtgtgaa ggctctaaga gacattgaac ctggagaaga aatttcttgt   1140
tattatggag atgggttctt tggagaaaat aatgagttct gcgagtgtta cacttgcgaa   1200
agacggggca ctggtgcttt taatccaga gtgggactgc ctgcgcctgc tcctgttatc   1260
aatagcaaat atggactcag agaaacagat aaacgtttaa ataggcttaa aaagttaggt   1320
gacagcagca aaaattcaga cagtcaatct gtcagctcta acactgatgc agataccact   1380
caggaaaaaa acaatgcaag taagtaaggg agatttgata agcatatctt ttaaaagtat   1440
```

```
tttcacacaa tttgctttat aaagtgtgct tcagtagttt taaactttta aatactcaga       1500
gagactggga cttgtgagct ttggctgcac ttcaaggctc tagacgtgat ttgagtagag       1560
gcacagtctg tatcccatct ctaacttcag taccgtcctc tagactattt ttcttgaata       1620
ccttggtaac tggatatgag ttcttcatca tatgttccaa ggtcatcata tgttttaaac       1680
attttcaagg tgttagagac tgtgatgatg tcgctaagtc ctgcaagaag acaaaaggac       1740
tgagtagaat taaattagac tctatacatt ccagtgccta gccagtttgt tagaaaagat       1800
gatggacttg gggaattcat agcttctggc cttaaggctt ccaccttttc attgcttgct       1860
gaccttttcc aaaacgaact gactcagttc agcagaccac cagtaccaga ctcagaattg       1920
tgatagagga gcattttgaa cagtgccgta ttgtgacatg ctgtattggc tactccagaa       1980
agtaggagta aagatggaaa ggagaaagaa gcaacctctg agattccagt ggtgtgtggg       2040
ggcaagatct gatggaaact gaaaagaga acgaagacta aacaaagaaa aaaaaaaaa       2100 aa                                                                      2102
```

<210> SEQ ID NO 27
<211> LENGTH: 2658
<212> TYPE: DNA
<213> ORGANISM: Homo sapiens

<400> SEQUENCE: 27

```
attattttg gtgattaatt ttctgggggg gactgggacg cggggcccgg cggcgcggcc         60
ccgcatcgca gcggccgggc agcggggcct gggacgcgcc ccgaggagga gcggggcggc        120
gcaggcggag agaacattga agtattctc taagctattt gaagagagtg actaaatgca        180
cctgggtcag gctgtctgtg ggtatgaagt ggttgggaga atccaagaac atggtggtga        240
atggcaggag aaatggaggc aagttgtcta atgaccatca gcagaatcaa tcaaaattac        300
agcacacggg gaaggacacc ctgaaggctg gcaaaaatgc agtcgagagg aggtcgaaca        360
gatgtaatgg taactcggga tttgaaggac agagtcgcta tgtaccatcc tctggaatgt        420
ccgccaagga actctgtgaa aatgatgacc tagcaaccag tttggttctt gatccctatt        480
taggttttca aacacacaaa atgaatacta gcgccttttcc ttcgaggagc tcaaggcatt        540
tttcaaaatc tgacagtttt tctcacaaca accctgtgag atttaggcct attaaaggaa        600
ggcaggaaga actaaaggaa gtaattgaac gttttaagaa agatgaacac ttggagaaag        660
ccttcaaatg tttgacttca ggcgaatggg cacggcacta ttttctcaac aagaataaaa        720
tgcaggagaa attattcaaa gaacatgtat ttatttattt gcgaatgttt gcaactgaca        780
gtggatttga atattgcca tgtaatagat actcatcaga acaaaatgga gccaaaatag        840
ttgcaacaaa agagtggaaa cgaaatgaca aaatagaatt actggtgggt tgtattgccg        900
aactttcaga aattgaggag aacatgctac ttagacatgg agaaaacgac ttcagtgtca        960
tgtactccac aaggaaaaac tgtgctcaac tctggctggg tcctgctgcg tttataaacc       1020
atgattgcag acctaattgt aagtttgtgt caactggtcg agatacagca tgtgtgaagg       1080
ctctaagaga cattgaacct ggagaagaaa tttcttgtta ttatggagat gggttctttg       1140
gagaaaataa tgagttctgc gagtgttaca cttgcgaaag acgggcact ggtgcttttta       1200 aatccagagt gggactgcct gcgcctgctc ctgttatcaa tagcaaatat ggactcagag       1260
aaacagataa acgtttaaat aggcttaaaa agttaggtga cagcagcaaa aattcagaca       1320
gtcaatctgt cagctctaac actgatgcag ataccactca ggaaaaaaac aatgcaagta       1380
agtaagggag attttgataag catatctttt aaaagtattt tcacacaatt tgctttataa       1440
```

| | |
|---|---:|
| agtgtgcttc agtagtttta aacttttaaa tactcagaga gactgggact tgtgagcttt | 1500 |
| ggctgcactt caaggctcta gacgtgattt gagtagaggc acagtctgta tcccatctct | 1560 |
| aacttcagta ccgtcctcta gactattttt cttgaatacc ttggtaactg gatatgagtt | 1620 |
| cttcatcata tgttccaagg tcatcatatg ttttaaacat tttcaaggtg ttagagactg | 1680 |
| tgatgatgtc gctaagtcct gcaagaagac aaaaggactg agtagaatta aattagactc | 1740 |
| tatacattcc agtgcctagc cagtttgtta gaaaagatga tggacttggg gaattcatag | 1800 |
| cttctggcct taaggcttcc acctttttcat tgcttgctga cctttttcaa aacgaactga | 1860 |
| ctcagttcag cagaccacca gtaccagact cagaattgtg atagaggagc attttgaaca | 1920 |
| gtgccgtatt gtgacatgct gtattggcta ctccagaaag taggagtaaa gatggaaagg | 1980 |
| agaaagaagc aacctctgag attccagtgg tgtgtggggg caagatctga tggaaactga | 2040 |
| aaaagagaac gaagactaaa caagagaaa ggaaagagaa gaaaccctaa atgggcaaag | 2100 |
| gaaagcacat cctgtttgcg gagctttgaa atattggaac catttctaat tgctcctgtt | 2160 |
| tttctgggta acaccagttt tctgtagttg ccactaaagc agtagactct tgagtctcac | 2220 |
| ttgtctctga gagagacaga agttagaaag ttttgacttg gcgattccga aagtatgcct | 2280 |
| ttgttggcac ttaaatgtcc agtgagactt cttggcacct tagagccctc tgagatactg | 2340 |
| attattttag gttcttctcc ctactttcag atgttttcag cccaacactg ggtgctctct | 2400 |
| tccactacag agaatcctga agaaaaggga aggtgtttcc catgatggtg aatgtcactg | 2460 |
| ccatgaattc ctgaatctac ctgctgctgg gagtcagagt ccaagcataa cccgtgtagc | 2520 |
| ataaaagcag cgctgtagcc ctattccagt ctttttcgtt aatgtccaga gtgaacaaca | 2580 |
| agagttagtc aatcattaac tgttgactgt tgattctcat aataaatgca gcataacgac | 2640 |
| aaaaaaaaaa aaaaaaaa | 2658 |

<210> SEQ ID NO 28
<211> LENGTH: 2292
<212> TYPE: DNA
<213> ORGANISM: Homo sapiens

<400> SEQUENCE: 28

| | |
|---|---:|
| gttacacttg cgaaagacgg ggcactggtg cttttaaatc cagagtggga ctgcctgcgc | 60 |
| ctgctcctgt tatcaatagc aaatatggac tcagagaaac agataaacgt ttaaataggc | 120 |
| ttaaaaagtt aggtgacagc agcaaaaatt cagacagtca atctgtcagc tctaacactg | 180 |
| atgcagatac cactcaggaa aaaacaatg caacttctaa ccgaaaatct tcagttggcg | 240 |
| taaaaaagaa tagcaagagc agaacgttaa cgaggcaatc tatgtcaaga attccagctt | 300 |
| cttccaactc tacctcatct aagctaactc atataaataa ttccagggta ccaaagaaac | 360 |
| tgaagaagcc tgcaaagcct ttactttcaa agataaaatt gagaaatcat tgcaagcggc | 420 |
| tggagcaaaa gaatgcttca agaaaactcg aaatgggaaa cttagtactg aaagagccta | 480 |
| aagtagttct gtataaaaat ttgcccatta aaaagataa ggagccagag ggaccagccc | 540 |
| aagccgcagt tgccagcggg tgcttgacta gacacgcggc gagagaacac agacagaatc | 600 |
| ctgtgagagg tgctcattcg caggggggaga gctcgccctg cacctacata actcggcggt | 660 |

```
cagtgaggac aagaacaaat ctgaaggagg cctctgacat caagcttgaa ccaaatacgt      720
tgaatggcta taaaagcagt gtgacggaac cttgccccga cagtggtgaa cagctgcagc      780
cagctcctgt gctgcaggag gaagaactgg ctcatgagac tgcacaaaaa ggggaggcaa      840
agtgtcataa gagtgacaca ggcatgtcca aaaagaagtc acgacaagga aaacttgtga      900
aacagtttgc aaaaatagag gaatctactc cagtgcacga ttctcctgga aaagacgacg      960
cggtaccaga tttgatgggt ccccattctg accagggtga gcacagtggc actgtgggcg     1020
tgcctgtgag ctacacagac tgtgctcctt cacccgtcgg ttgttcagtt gtgacatcag     1080
atagcttcaa acaaaagac agctttagaa ctgcaaaaag taaaaagaag aggcgaatca     1140
caaggtatga tgcacagtta atcctagaaa ataactctgg gattcccaaa ttgactcttc     1200
gtaggcgtca tgatagcagc agcaaaacaa atgaccaaga gaatgatgga atgaactctt     1260
ccaaaataag catcaagtta agcaaagacc atgacaacga taacaatctc tatgtagcaa     1320
agcttaataa tggatttaac tcaggatcag gcagtagttc tacaaaatta aaaatccagc     1380
taaaacgaga tgaggaaaat aggggtctt atacagaggg gcttcatgaa aatgggtgt     1440 gctgcagtga tcctctttct ctcttggagt ctcgaatgga ggtggatgac tatagtcagt     1500
atgaggaaga aagtacagat gattcctcct cttctgaggg cgatgaagag gaggatgact     1560
atgatgatga ctttgaagac gatttttattc ctcttcctcc agctaagcgc ttgaggttaa     1620
tagttggaaa agactctata gatattgaca tttcttcaag gagaagagaa gatcagtctt     1680
taaggcttaa tgcctaagct cttggtctta acttgacctg ggataactac tttaaagaaa     1740
taaaaaattc cagtcaatta ttcctcaact gaaagtttag tggcagcact tctattgtcc     1800
cttcacttat cagcatacta ttgtagaaag tgtacagcat actgactcaa ttcttaagtc     1860
tgatttgtgc aaatttttat cgtacttttt aaatagcctt cttacgtgca attctgagtt     1920
agaggtaaag ccctgttgta aaataaaggc tcaagcaaaa ttgtacagtg atagcaactt     1980
tccacacagg acgttgaaaa cagtaatgtg gctacacagt ttttttaact gtaagagcat     2040
cagctggctc tttaatatat gactaaacaa taatttaaaa caaatcatag tagcagcata     2100
ttaagggttt ctagtatgct aatatcacca gcaatgatct ttggctttt gatttatttg     2160 ctagatgttt cccccttgga gttttgtcag tttcacactg tttgctggcc caggtgtact     2220
gtttgtggcc tttgttaata tcgcaaacca ttggttggga gtcagattgg tttcttaaaa     2280
aaaaaaaaaa aa                                                          2292
```

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
atgggatctc tgccccagtc a                                                  21

<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30

```
caagtgctca ccatgcttt                                                        19

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 31
tttttatgca cccaccgcag c                                                     21
```

GENE EXPRESSION PROFILING OF PARKINSON'S DISEASE

CROSS-REFERENCE TO RELATED APPLICATIONS

This application is the national stage entry of International Application No. PCT/US2007/082132, filed Oct. 22, 2007, which is entitled to priority to U.S. Provisional Patent Application No. 60/852,966, which was filed on Oct. 20, 2006, both of which are incorporated by reference in their entirety.

SEQUENCE LISTING

The instant application contains a Sequence Listing which has been submitted in ASCII format via EFS-Web and is hereby incorporated by reference in its entirety. Said ASCII copy, created on Mar. 15, 2012, is named 7230-59.txt and is 78,145 bytes in size.

BACKGROUND OF THE INVENTION

Parkinson's Disease (PD) is one of the major progressive neurological disorders for which no preventative or long-term effective treatment strategies are available. Idiopathic PD is a multisystem disorder with a multifactorial etiology and diverse clinical phenotype. The risk of developing PD increases with age, and afflicted individuals are usually adults over 40. PD occurs in all parts of the world, and affects more than one million individuals in the United States alone.

PD is characterized by degeneration of dopaminergic neurons of the substantia nigra. The substantia nigra is a portion of the lower brain, or brain stem, that helps control voluntary movements. The shortage of dopamine in the brain caused by the loss of these neurons is believed to cause the observable disease symptoms.

The symptoms of PD may vary from patient to patient. The most common symptom is a paucity of movement: That is, rigidity characterized by an increased stiffness of voluntary skeletal muscles. Additional symptoms include resting tremor, bradykinesia (slowness of movement), poor balance, and problems walking. Common secondary symptoms include depression, sleep disturbance, dizziness, stooped posture, dementia, and problems with speech, breathing, and swallowing. The symptoms become progressively worse and ultimately result in death.

The primary cause of Parkinson's Disease is not known. Polymorphism in certain genes appears to be a risk factor, but there is no direct evidence for the causal relationship between polymorphism and increased risk of PD. Only a small percentage (<5%) of patients develop PD that may be linked to the currently known gene mutations (1). In familial PD, mutation in the synuclein gene is associated with the disease, but a direct role of this gene in degeneration of dopaminergic neurons remains to be established. Although mutations in the Parkin gene have been associated with autosomal recessive juvenile Parkinson's Disease, the role of this gene mutation in causing degeneration of dopaminergic neurons has not been defined. In idiopathic PD, epigenetic (mitochondria, membranes, protein modifications) rather than genetic events may be primary targets which, when impaired, initiate degeneration of dopaminergic neurons, eventually leading to cell death.

Although the nature of neurotoxins that cause degeneration in dopaminergic neurons in PD is not well understood, oxidative stress is one of the intermediary risk factors that could initiate and/or promote such degeneration. Therefore, supplementation with antioxidants may prevent or reduce the rate of PD progression. Supplementation with multiple antioxidants at appropriate doses is desirable because: various types of free radicals are produced in vivo, antioxidants vary in their ability to quench different free radicals, and cellular environments vary with respect to their lipid and aqueous phases. L-dihydroxyphenylalanine (L-dopa) is one of the agents used in the treatment of PD.

In addition to genome-wide association studies, which have identified polymorphisms that potentially confer susceptibility to PD (2), gene array surveys of the substantia nigra (SN) and other regions of the brain have provided some insights into the biological, cellular and molecular pathways implicated in PD (3-7).

There is a continuing need to identify genes and gene products that are associated with Parkinson's Disease or the progression of Parkinson's Disease, to provide means for screening, diagnosing, and evaluating Parkinson's Disease patients and patients suspected of having Parkinson's Disease. By identifying such genes and gene products, Parkinson's Disease treatments can be identified, evaluated, and may be selected for individualized care of PD patients.

SUMMARY OF THE INVENTION

The present disclosure identifies changes in gene expression that are associated with Parkinson's Disease. These changes in gene expression were identified by examining gene expression in multiple regions of normal brain samples and brain samples from patients having Parkinson's Disease. The gene expression analysis disclosed herein includes an analysis of multiple brain regions of PD patients, as well as an analysis of gene expression in the blood of PD patients, as compared to controls. As discussed more fully herein, genes or gene products that display differential gene expression in multiple regions of a PD brain, as compared to corresponding samples from control populations, are desirable as diagnostic and prognostic markers of PD.

In one aspect, the invention provides a method of diagnosing Parkinson's Disease in a patient. In this aspect, the method comprises detecting the level of expression of one or more genes from Tables 4-6 in a biological sample from the patient. The differential expression of these genes as compared to corresponding control levels is indicative of Parkinson's Disease.

In certain embodiments of the invention, the biological sample is a biological fluid, such as blood, urine, cerebrospinal fluid, or lymph, from the patient. Further, the biological sample may be derived from the biological fluid, such as a sample derived from blood.

In certain embodiments of the invention, the patient being tested is exhibiting symptoms of Parkinson's Disease or is being treated for Parkinson's Disease, making an evaluation of the patient for the presence of PD necessary. In these and other embodiments, the Parkinson's Disease is idiopathic Parkinson's Disease. In certain embodiments, the patient is known to be susceptible to PD, for example, on the basis of genotyping. Such genotyping may be conducted in addition to the gene expression analyses disclosed herein for further evaluation of the patient's disease state.

In another aspect, the invention provides a method for evaluating Parkinson's Disease in a patient. In this aspect, the method comprises determining a first level of expression of one or more genes from Tables 4-6 in a biological sample from the Parkinson's Disease patient. A treatment for Parkinson's Disease, or a candidate treatment, may then be administered to the patient if necessary. At least a second level of expression of the genes is subsequently determined in a biological sample that is obtained from the patient during the course of the treatment. Where the genes in the first sample are differentially expressed as compared to the second sample (or third, fourth, and so on), the treatment or candidate treatment is identified as being effective for treatment of the Parkinson's Disease. For example, L-dopa is known to produce free radicals during its normal metabolism. L-dopa may lead to the gene expression changes disclosed in the present invention, which may therefore be used to monitor drug efficacy. Thus, in this embodiment, the patient is undergoing therapy with L-dopa, and gene expression values monitored during treatment.

Any method of gene expression analysis may be used in accordance with the present invention, and such methods are well known in the art. For example, in certain embodiments, the level of expression of one or more genes listed in Tables 4-6 are determined by a nucleic acid polymerization or hybridization technology. For example, suitable assays include RT-PCR, northern blotting, and functionally similar techniques.

The genes identified herein as useful diagnostic and prognostic markers for PD are differentially expressed in one or more brain regions of Parkinson's Disease patients, as well as in other tissues. For example, such brain regions include substantia nigra, ventral tegmental area, cingulate cortex (BA35), insular cortex, amygdala, nucleus basalis, caudate, putamen, nucleus accumbens, globus pallidus, mediodorsal thalamus, pulvinar, subthalamic nucleus, nucleus ambiguous, cerebellar hemisphere, anterior cerebellar vermis, dorsal raphe, locus ceruleus, hypothalamus, hippocampus and reticular formation.

As disclosed herein, the genes identified in Tables 4-6 are differentially expressed in PD, including the following genes: Mitochondrial Ribosome Protein S6 (MRPS6), Solute Carrier Family 5, member 3 (SLC5A3), Histone 1, H2bd (H1ST1H2BD), RNA Binding Motif Protein 3 (RBM3), Solute Carrier Family 38, member 2 (SLC38A2), Cysteine/Histidine-rich Domain-Containing Zinc Binding Protein 1 (CHORDC1), Cold Inducible RNA Binding Protein (CIRBP), cAMP dependent protein kinase, beta catalytic subunit PRKACB, Stress-induced Phosphoprotein (STIP1), Hypothetical Protein FLJ33814, FUS Interacting Protein (serine/arginine-rich) 1 (FUSIP1), and Suppressor of Variegation 4-20 homolog 1 (SUV420H1). Table 4 lists these genes along with the number of brain regions for which they are differentially expressed, and the fold change in gene expression. The methods of the invention may determine the levels or changes in gene expression of one, two, five, ten, all, or nearly all, of these genes, or the level of their corresponding gene products (e.g., translation products) as discussed below.

In certain embodiments of the invention, the methods involve determining the levels of expression or changes in expression of at least two of MRP6, SLC5A3, and PRKACB. For example, MRP6 and SLC5A3 are expressed at higher levels in PD patients, while PRKACB is expressed at lower levels in PD patients.

As discussed herein, these aspects of the invention may be embodied in the form of a kit for diagnosing Parkinson's Disease. The kit may be designed for use in any gene expression assay. Generally, the kit includes a plurality of probes or a plurality of primers for detecting the expression level of one, or two or more, genes listed in Tables 4-6, including those listed above. The kit further includes the necessary reagents for detecting gene expression levels in a sample. The kit may also contain one or more solid supports having attached thereto the one or more probe oligonucleotides. For example, the solid support may be an oligonucleotide array. The kits may further comprise one or more reagents for use with the arrays, one or more signal detection and/or array-processing instruments, one or more gene expression databases, and one or more analysis and database management software packages.

In another aspect, the invention involves diagnosing Parkinson's Disease in a patient by detecting the level of one or more translation products in a biological sample from the patient. Such biological samples include biological fluids such as blood and blood products. The translation products detected in accordance with this aspect are the translation products of genes listed in Tables 4-6, including those listed above. Where there is a difference in the levels of the translation products in the sample as compared to control levels (as described herein), the patient is identified as having Parkinson's Disease.

In another aspect, the invention provides a method for evaluating Parkinson's Disease in a patient. The method comprises initially determining a first level of one or more translation products in a biological sample from a Parkinson's Disease patient. These translation products are the translation products of the genes listed in Tables 4-6, including those listed above. The first level of the gene products may be determined prior to treatment for PD. The patient may then be administered a treatment for Parkinson's Disease if necessary (e.g., L-dopa), and subsequently, at least a second level of the gene products is determined in a second biological sample obtained from the patient during the course of the treatment. Where a difference in the levels of the gene products in the first sample as compared to the second sample is detected, the treatment is determined to be effective for the treatment of Parkinson's Disease. In certain, embodiments, the first and second levels are also compared to the levels in healthy controls to further evaluate the efficacy of the treatment.

In accordance with this aspect, the translation products may be detected by any known method, including an immunological assay such as ELISA.

In accordance with these aspects, the invention may be embodied in the form of a kit for diagnosing Parkinson's Disease. The kit may be designed to detect gene products in accordance with any known immunological assay format, including ELISA and absorbent strip assays. Generally, the kit includes a plurality of antibodies for detecting the level of two or more gene products, the gene products being translation products of the genes listed in Tables 4-6, including those listed above. For example, the kit may comprise antibodies that recognize one, two, or all of MRP6, SLC5A3, and PRKACB, along with necessary reagents for detecting antigen/antibody reactions.

The invention further includes methods of screening for an agent capable of modulating the onset or progression of Parkinson's Disease, comprising the steps of exposing a cell to the agent; and detecting the expression level of one or more genes from Tables 4-6. Where the agent modulates the expression of the genes listed in Tables 4-6, as disclosed herein, the agent is a candidate agent for treating or mimicking Parkinson's Disease.

DETAILED DESCRIPTION OF EMBODIMENTS

Figure 1:
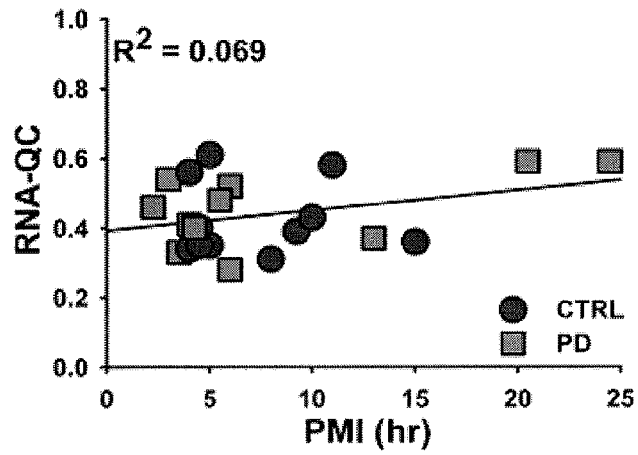
FIG. 1 is a graph depicting quality control (QC) parameters for RNA. The relationships between RNA QC (determined by the average of the 5/3 signal ratios of β-actin and GapDH across Plus 2.0 chips) and the postmortem interval (PMI) in SN show no effect of the PMI on the QC measurements.

Many biological functions are accomplished by altering the expression of various genes through transcriptional (e.g., through control of initiation, provision of RNA precursors, RNA processing, etc.) and/or translational control. For example, fundamental biological processes such as cell cycle, cell differentiation and cell death, are often characterized by the variations in the expression levels of groups of genes.

Changes in gene expression also are associated with pathogenesis. For example, the lack of sufficient expression of functional tumor suppressor genes and/or the over expression of oncogene/protooncogenes could lead to tumorgenesis or hyperplastic growth of cells (Marshall, (1991) Cell, 64, 313-326; Weinberg, (1991) Science, 254, 1138-1146). Thus, changes in the expression levels of particular genes serve as signposts for the presence and progression of various diseases.

The present inventors have examined tissue samples from multiple regions of normal brain and from known Parkinson's Disease samples, to identify the changes in gene expression associated with Parkinson's Disease. These changes in gene expression, also referred to as expression profiles, provide diagnostic markers as well as markers to monitor disease states, disease progression, and drug efficacy.

As shown herein, nucleic acid samples of isolated tissues from multiple brain regions of individuals with Parkinson's Disease, and from individuals without the disease, were applied to a DNA microarray. Multiregional gene expression analysis was then performed to identify genes with increased or decreased expression in subsets of Parkinson's Disease patients. Exemplary genes that are differentially expressed in PD brain samples are listed in Tables 4-6.

Gene microarrays were performed utilizing Affymetrix gene chips. Brain specimens from different cortical and subcortical regions were taken from PD and normal aged brain donors. Only samples satisfying strict RNA and microarray quality criteria were utilized in the multiregional comparisons between PD patients and controls. Gene expression was considered significantly different if the fold change was >±1.3, and p-values were ≦0.05.

The present inventors have also examined blood samples from Parkinson's Disease patients to identify or confirm the changes in gene expression associated with Parkinson's Disease.

Nucleic Acid-Based Assay Formats

The present invention includes methods that quantify expression levels in clinical samples as well as methods that determine whether a gene of interest is expressed at all or expressed above a threshold (e.g., a control threshold) in clinical samples. Thus, an assay which provides a "yes or no" result without necessarily providing quantification of gene expression is within the scope of the present invention. Thus, the invention may involve quantitative or qualitative assessment of gene expression.

The genes identified as being differentially expressed in Parkinson's Disease may be used in a variety of nucleic acid detection assays to detect or quantify the expression level of a gene or multiple genes in a given sample. For example, traditional Northern blotting, nuclease protection, RT-PCR and differential display methods may be used for detecting gene expression levels, including Taqman and flap endonuclease assays. Additional assays include array or chip hybridization-based methods, which are convenient when determining the expression levels of a larger number of genes.

In some embodiments, the invention may employ reverse transcription polymerase chain reaction (RT-PCR), which is a sensitive method for the detection of mRNA, including low abundant mRNAs present in clinical tissue samples. The application of fluorescence techniques to RT-PCR combined with suitable instrumentation has led to quantitative RT-PCR methods that combine amplification, detection and quantification in a closed system. Two commonly used quantitative RT-PCR techniques are the Taqman RT-PCR assay (ABI, Foster City, USA) and the Lightcycler assay (Roche, USA).

Thus, in one embodiment of the present invention, the method comprises conducting real-time quantitative PCR (TaqMan) with sample-derived RNA and control RNA. Holland, et al., PNAS 88:7276-7280 (1991) describe an assay known as a Taqman assay. The 5' to 3' exonuclease activity of Taq polymerase is employed in a polymerase chain reaction product detection system to generate a specific detectable signal concomitantly with amplification. An oligonucleotide probe, nonextendable at the 3' end, labeled at the 5' end, and designed to hybridize within the target sequence, is introduced into the polymerase chain reaction assay. Annealing of the probe to one of the polymerase chain reaction product strands during the course of amplification generates a substrate suitable for exonuclease activity. During amplification, the 5' to 3' exonuclease activity of Taq polymerase degrades the probe into smaller fragments that can be differentiated from undegraded probe. A version of this assay is also described in Gelfand et al., in U.S. Pat. No. 5,210,015, which is hereby incorporated by reference.

Further, U.S. Pat. No. 5,491,063 to Fisher, et al., provides a Taqman-type assay. The method of Fisher et al. provides a reaction that results in the cleavage of single-stranded oligonucleotide probes labeled with a light-emitting label wherein the reaction is carried out in the presence of a DNA binding compound that interacts with the label to modify the light emission of the label. The method utilizes the change in light emission of the labeled probe that results from degradation of the probe. The methods are applicable in general to assays that utilize a reaction that results in cleavage of oligonucleotide probes, and in particular, to homogeneous amplification/detection assays where hybridized probe is cleaved concomitant with primer extension.

The TaqMan detection assays offer several advantages over the classical PCR assays. First, the TaqMan assays combine the sensitivity of PCR along with hybridization of the internal oligonucleotide sequence that is present in a target sequence. Following PCR, samples do not have to be separated on agarose gels, and the subsequent Southern blots and hybridization steps that are necessary to verify the identity of the PCR products is eliminated. Using the TaqMan system, the assays are completed within 2.5 h. Further, the methodology involved in the assay process makes possible the handling of large numbers of samples efficiently and without cross-contamination and is therefore adaptable for robotic sampling. As a result, large numbers of test samples can be processed in a very short period of time using the TaqMan assay. Another advantage of the TaqMan system is the potential for multiplexing. Since different fluorescent reporter dyes can be used to construct probes, the expression of several different genes associated with PD could be assayed in the same PCR reaction, thereby reducing the labor costs that would be incurred if each of the tests were performed individually.

In other embodiments, the invention employs detection and quantification of RNA levels in real-time using nucleic acid sequence based amplification (NASBA) combined with molecular beacon detection molecules. NASBA is a singe-step isothermal RNA-specific amplification method that amplifies mRNA in a double stranded DNA environment, and this method has recently proven useful in the detection of various mRNAs, and in the detection of both viral and bacterial RNA in clinical samples.

In yet other embodiments, the invention uses an assay employing a flap endonuclease, such as the Invader™ assay (Third Wave Technologies). In the case of using the invader method, an invader probe containing a sequence specific to the region 3' to a target site, and a primary probe containing a sequence specific to the region 5' to the target site of a template and an unrelated flap sequence, are prepared. Cleavase is then allowed to act in the presence of these probes, the target molecule, as well as a FRET probe containing a sequence complementary to the flap sequence and an auto-complementary sequence that is labeled with both a fluorescent dye and a quencher. When the primary probe hybridizes with the template, the 3' end of the invader probe penetrates the target site, and this structure is cleaved by the Cleavase resulting in dissociation of the flap. The flap binds to the FRET probe and the fluorescent dye portion is cleaved by the Cleavase resulting in emission of fluorescence.

The invention may also employ hybridization-based assays. Nucleic acid hybridization simply involves contacting a probe and target nucleic acid under conditions where the probe and its complementary target can form stable hybrid duplexes through complementary base pairing (see Lockhart et al., (1999) WO 99/32660). The nucleic acids that do not form hybrid duplexes are then washed away leaving the hybridized nucleic acids to be detected, typically through detection of an attached detectable label. It is generally recognized that nucleic acids are denatured by increasing the temperature or decreasing the salt concentration of the buffer containing the nucleic acids.

Under low stringency conditions (e.g., low temperature and/or high salt) hybrid duplexes (e.g., DNA-DNA, RNA-RNA or RNA-DNA) will form even where the annealed sequences are not perfectly complementary. Thus specificity of hybridization is reduced at lower stringency. Conversely, at higher stringency (e.g., higher temperature or lower salt) successful hybridization requires fewer mismatches. One of skill in the art will appreciate that hybridization conditions may be selected to provide any degree of stringency. In a preferred embodiment, hybridization is performed at low stringency, in this case in 6×SSPE-T at 37° C. (0.005% Triton x-100) to ensure hybridization and then subsequent washes are performed at higher stringency (e.g., 1×SSPE-T at 37° C.) to eliminate mismatched hybrid duplexes. Successive washes may be performed at increasingly higher stringency (e.g., down to as low as 0.25×SSPET at 37° C. to 50° C.) until a desired level of hybridization specificity is obtained. Stringency can also be increased by addition of agents such as formamide. Hybridization specificity may be evaluated by comparison of hybridization to the test probes with hybridization to the various controls that can be present (e.g., expression level control, normalization control, mismatch controls, etc.).

In general, there is a tradeoff between hybridization specificity (stringency) and signal intensity. Thus, in a preferred embodiment, the wash is performed at the highest stringency that produces consistent results and that provides a signal intensity greater than approximately 10% of the background intensity. Thus, in a preferred embodiment, the hybridized array may be washed at successively higher stringency solutions and read between each wash. Analysis of the data sets thus produced will reveal a wash stringency above which the hybridization pattern is not appreciably altered and which provides adequate signal for the particular oligonucleotide probes of interest.

The hybridized nucleic acids are typically detected by detecting one or more labels attached to the sample nucleic acids. The labels may be incorporated by any of a number of means well known to those of skill in the art (see Lockhart et al., (1999) WO 99/32660).

When employing hybridization formats, solution-based and solid support-based assay formats may be employed. Solid supports containing oligonucleotide probes for differentially expressed genes of the invention can be filters, polyvinyl chloride dishes, silicon or glass based chips, etc. Such wafers and hybridization methods are widely available, for example, those disclosed by Beattie (WO 95/11755). Any solid surface to which oligonucleotides can be bound, either directly or indirectly, either covalently or non-covalently, can be used. An exemplary solid support is a high density array or DNA chip. These contain a particular oligonucleotide probe in a predetermined location on the array. Each predetermined location may contain more than one molecule of the probe, but each molecule within the predetermined location has an identical sequence. Such predetermined locations are termed features. There may be, for example, about 2, 10, 100, 1000 to 10,000; 100,000 or 400,000 of such features on a single solid support. The solid support, or the area within which the probes are attached may be on the order of a square centimeter.

Oligonucleotide probe arrays for expression monitoring can be made and used according to any techniques known in the art (see for example, Lockhart et al., (1996) Nat. Biotechnol. 14, 1675-1680; McGall et al., (1996) Proc. Nat. Acad. Sci. USA 93, 13555-13460). Such probe arrays may contain at least two or more oligonucleotides that are complementary to or hybridize to two or more of the genes described herein. Such arrays may also contain oligonucleotides that are complementary or hybridize to at least about 2, 3, 4, 5, 6, 7, 8, 9, 10, 20, 30, 50, or all of the genes described herein as being differentially expressed in PD.

The mRNA or reversed transcribed mRNA may optionally be cloned or amplified. The cloning itself does not appear to bias the representation of mRNA within a population. However, it may be preferable to use polyA+RNA as a source, as it can be used with less processing steps.

The sequences of the expression marker genes are in the public databases. Table 4 provides the Affymetrix fragment ID for several genes that are differentially expressed in PD, as well as the SEQ ID NOS. The column labeled "Gene Symbol" refers to the abbreviated names of the genes correlating the Affymetrix gene fragment ID. Table 6 further lists the GeneBank accession IDs for the differentially expressed genes, which are hereby incorporated by reference.

Probes based on the sequences of the genes described herein may be prepared by any commonly available method. Oligonucleotide probes for assaying the tissue or cell sample are preferably of sufficient length to specifically hybridize only to appropriate, complementary genes or transcripts. Typically the oligonucleotide probes will be at least 10, 12, 14, 16, 18, 20 or 25 nucleotides in length. In some cases longer probes of at least 30, 40, or 50 nucleotides will be desirable.

As used herein, oligonucleotide sequences that are complementary to one or more of the genes described herein, refers to oligonucleotides that are capable of hybridizing under stringent conditions to at least part of the nucleotide sequence of said genes. Such hybridizable oligonucleotides will typically exhibit at least about 75% sequence identity at the nucleotide level to said genes, preferably about 80% or 85% sequence identity or more preferably about 90% or 95% or more sequence identity to said genes. In some embodiments, the oligonucleotide probes are identical to a portion of the genes disclosed herein, and usually identical in a range of 10-30 nucleotides, such as 15-20 nucleotides.

The terms "background" or "background signal intensity" refer to hybridization signals resulting from non-specific binding, or other interactions, for example between a labeled target nucleic acid and components of the oligonucleotide array (e.g., the oligonucleotide probes, control probes, the array substrate, etc.). Background signals may also be produced by intrinsic fluorescence of the array components themselves. A single background signal can be calculated for the entire array, or a different background signal may be calculated for each target nucleic acid. In a preferred embodiment, background is calculated as the average hybridization signal intensity for the lowest 5% to 10% of the probes in the array, or, where a different background signal is calculated for each target gene, for the lowest 5% to 10% of the probes for each gene. Of course, one of skill in the art will appreciate that where the probes to a particular gene hybridize well and thus appear to be specifically binding to a target sequence, they should not be used in a background signal calculation. Alternatively, background may be calculated as the average hybridization signal intensity produced by hybridization to probes that are not complementary to any sequence found in the sample (e.g., probes directed to nucleic acids of the opposite sense or to genes not found in the sample such as bacterial genes). Background can also be calculated as the average signal intensity produced by regions of the array that lack any probes at all.

The phrase "hybridizing specifically to" refers to the binding, duplexing or hybridizing of a molecule substantially to or only to a particular nucleotide sequence or sequences under stringent conditions when that sequence is present in a complex mixture (e.g., total cellular) DNA or RNA.

The term "mismatch control" or "mismatch probe" refer to a probe whose sequence is deliberately selected not to be perfectly complementary to a particular target sequence. For each mismatch (MM) control in a high-density array there typically exists a corresponding perfect match (PM) probe that is perfectly complementary to the same particular target sequence. The mismatch may comprise one or more bases.

While the mismatch(es) may be located anywhere in the mismatch probe, terminal mismatches are less desirable as a terminal mismatch is less likely to prevent hybridization of the target sequence. In a particularly preferred embodiment, the mismatch is located at or near the center of the probe such that the mismatch is most likely to destabilize the duplex with the target sequence under the test hybridization conditions. The term "perfect match probe" refers to a probe that has a sequence that is perfectly complementary to a particular target sequence. The test probe is typically perfectly complementary to a portion (subsequence) of the target sequence. The perfect match (PM) probe can be a "test probe", a "normalization control" probe, an expression level control probe and the like. A perfect match control or perfect match probe is, however, distinguished from a "mismatch control" or "mismatch probe."

As used herein a "probe" is defined as a nucleic acid, capable of binding to a target nucleic acid of complementary sequence through one or more types of chemical bonds, usually through complementary base pairing, usually through hydrogen bond formation. As used herein, a probe may include natural (i.e., A, G, U, C or T) or modified bases (7-deazaguanosine, inosine, etc.). In addition, the bases in probes may be joined by a linkage other than a phosphodiester bond, so long as it does not interfere with hybridization. Thus, probes may be peptide nucleic acids in which the constituent bases are joined by peptide bonds rather than phosphodiester linkages.

The term "stringent conditions" refers to conditions under which a probe will hybridize to its target subsequence, but with only insubstantial hybridization to other sequences or to other sequences such that the difference may be identified. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH.

Typically, stringent conditions will be those in which the salt concentration is at least about 0.01 to 1.0 M sodium ion concentration (or other salts) at pH 7.0 to 8.3 and the temperature is at least about 30° C. for short probes (e.g., 10 to 50 nucleotide). Stringent conditions may also be achieved with the addition of destabilizing agents such as formamide.

The "percentage of sequence identity" or "sequence identity" is determined by comparing two optimally aligned sequences or subsequences over a comparison window or span, wherein the portion of the polynucleotide sequence in the comparison window may optionally comprise additions or deletions (i.e., gaps) as compared to the reference sequence (which does not comprise additions or deletions) for optimal alignment of the two sequences. The percentage is calculated by determining the number of positions at which the identical monomer unit (e.g., nucleic acid base or amino acid residue) occurs in both sequences to yield the number of matched positions, dividing the number of matched positions by the total number of positions in the window of comparison and multiplying the result by 100 to yield the percentage of sequence identity. Percentage sequence identity when calculated using the programs GAP or BESTFIT (see below) is calculated using default gap weights.

Homology or identity may be determined by BLAST (Basic Local Alignment Search Tool) analysis using the algorithm employed by the programs blastp, blastn, blastx, tblastn and tblastx (Karlin et al., (1990) Proc. Natl. Acad. Sci. USA 87, 2264-2268 and Altschul, (1993) J. Mol. Evol. 36, 290-300, fully incorporated by reference) which are tailored for sequence similarity searching. The approach used by the BLAST program is to first consider similar segments between a query sequence and a database sequence, then to evaluate the statistical significance of all matches that are identified and finally to summarize only those matches which satisfy a preselected threshold of significance. For a discussion of basic issues in similarity searching of sequence databases, see Altschul et al., (1994) Nature Genet. 6, 119-129) which is filly incorporated by reference. The search parameters for histogram, descriptions, alignments, expect (i.e., the statistical significance threshold for reporting matches against database sequences), cutoff, matrix and filter are at the default settings. The default scoring matrix used by blastp, blastx, tblastn, and tblastx is the BLOSUM62 matrix (Henikoff et al., (1992) Proc. Natl. Acad. Sci. USA 89, 10915-10919, fully incorporated by reference). Four blastn parameters were adjusted as follows: Q=10 (gap creation penalty); R=10 (gap extension penalty); wink=1 (generates word hits at every Wink™ position along the query); and gapw=16 (sets the window width within which gapped alignments are generated). The equivalent Blastp parameter settings were Q=9; R=2; wink=1; and gapw=32. A Bestfit comparison between sequences, available in the GCG package version 10.0, uses DNA parameters GAP=50 (gap creation penalty) and LEN=3 (gap extension penalty) and the equivalent settings in protein comparisons are GAP=8 and LEN=2.

The design of appropriate probes for hybridizing to a particular target nucleic acid, and as configured for any appropriate nucleic acid detection assay, is well known, and discussed supra.

Further, with respect to arrays, one of skill in the art will appreciate that an enormous number of array designs are suitable for the practice of this invention, where array embodiments are desirable. The array will typically include a number of probes that specifically hybridize to the sequences of interest. See WO 99/32660 for methods of producing probes for a given gene or genes. In addition, in a preferred embodiment, the array will include one or more control probes.

High density array chips of the invention include "test probes." Test probes may be oligonucleotides that range from about 5 to about 500 or about 5 to about 50 nucleotides, more preferably from about 10 to about 40 nucleotides and most preferably from about 15 to about 40 nucleotides in length. In other particularly preferred embodiments the probes are about 20 to 25 nucleotides in length. In another preferred embodiment, test probes are double or single strand DNA sequences. DNA sequences are isolated or cloned from natural sources or amplified from natural sources using natural nucleic acid as templates. These probes have sequences complementary to particular subsequences of the genes whose expression they are designed to detect. Thus, the test probes are capable of specifically hybridizing to the target nucleic acid they are to detect.

In addition to test probes that bind the target nucleic acid(s) of interest, the high density array can contain a number of control probes. The control probes fall into three categories referred to herein as (1) normalization controls; (2) expression level controls; and (3) mismatch controls.

Normalization controls are oligonucleotide or other nucleic acid probes that are complementary to labeled reference oligonucleotides or other nucleic acid sequences that are added to the nucleic acid sample. The signals obtained from the normalization controls after hybridization provide a control for variations in hybridization conditions, label intensity, "reading" efficiency and other factors that may cause the signal of a perfect hybridization to vary between arrays. In a preferred embodiment, signals (e.g., fluorescence intensity) read from all other probes in the array are divided by the signal (e.g., fluorescence intensity) from the control probes thereby normalizing the measurements.

Virtually any probe may serve as a normalization control. However, it is recognized that hybridization efficiency varies with base composition and probe length. Preferred normalization probes are selected to reflect the average length of the other probes present in the array, however, they can be selected to cover a range of lengths. The normalization control(s) can also be selected to reflect the (average) base composition of the other probes in the array, however in a preferred embodiment, only one or a few probes are used and they are selected such that they hybridize well (i.e., no secondary structure) and do not match any target-specific probes.

Expression level controls are probes that hybridize specifically with constitutively expressed genes in the biological sample. Virtually any constitutively expressed gene provides a suitable target for expression level controls. Typical expression level control probes have sequences complementary to subsequences of constitutively expressed "housekeeping genes" including, but not limited to the β-actin gene, the transferrin receptor gene, the GAPDH gene, the HPRT1 gene, and the like. As disclosed herein, the HPRT1 gene is particularly suitable as a control for expression, since HPRT1 is not differentially expressed in PD patients.

Mismatch controls may also be provided for the probes to the target genes, for expression level controls or for normalization controls. Mismatch controls are oligonucleotide probes or other nucleic acid probes identical to their corresponding test or control probes except for the presence of one or more mismatched bases. A mismatched base is a base selected so that it is not complementary to the corresponding base in the target sequence to which the probe would otherwise specifically hybridize. One or more mismatches are selected such that under appropriate hybridization conditions (e.g., stringent conditions) the test or control probe would be expected to hybridize with its target sequence, but the mismatch probe would not hybridize (or would hybridize to a significantly lesser extent). Preferred mismatch probes contain a central mismatch. Thus, for example, where a probe is a twenty-mer, a corresponding mismatch probe will have the identical sequence except for a single base mismatch (e.g., substituting a G, a C or a T for an A) at any of positions 6 through 14 (the central mismatch).

Mismatch probes thus provide a control for non-specific binding or cross hybridization to a nucleic acid in the sample other than the target to which the probe is directed. Mismatch probes also indicate whether a hybridization is specific or not. For example, if the target is present the perfect match probes should be consistently brighter than the mismatch probes. In addition, if all central mismatches are present, the mismatch probes can be used to detect a mutation. The difference in intensity between the perfect match and the mismatch probe (IBM)-I(MM)) provides a good measure of the concentration of the hybridized material.

Nucleic Acid Samples

As is apparent to one of ordinary skill in the art, nucleic acid samples used in the methods and assays of the invention may be prepared by any available method or process. Methods of isolating total mRNA are also well known to those of skill in the art. For example, methods of isolation and purification of nucleic acids are described in detail in Chapter 3 of Laboratory Techniques in Biochemistry and Molecular Biology: Hybridization With Nucleic Acid Probes, Part I Theory and Nucleic Acid Preparation, Tijssen, (1993) (editor) Elsevier Press. Such samples include RNA samples, but also include cDNA synthesized from a mRNA sample isolated from a cell or tissue of interest. Such samples also include DNA amplified from the cDNA, and an RNA transcribed from the amplified DNA. One of skill in the art would appreciate that it is desirable to inhibit or destroy RNase present in homogenates before homogenates can be used.

Biological samples may be of any biological tissue or fluid or cells. Typical clinical samples include, but are not limited to, sputum, blood, blood-cells (e.g., white cells), tissue or fine needle biopsy samples, urine, lymph, cerebrospinal fluid, peritoneal fluid, and pleural fluid, or cells therefrom.

Biological samples may also include sections of tissues, such as frozen sections or formalin fixed sections taken for histological purposes. In one embodiment, the tissues for the gene expression analysis are brain tissues, which includes brain tissue derived from several regions of the brain. Typical brain tissue samples include, but are not limited to, substantia nigra, ventral tegmental area, cingulate cortex (BA35), insular cortex, amygdala, nucleus basalis, caudate, putamen, nucleus accumbens, globus pallidus, mediodorsal thalamus, pulvinar, subthalamic nucleus, nucleus ambiguous, cerebellar hemisphere, anterior cerebellar vermis, dorsal raphe, locus ceruleus, hypothalamus, hippocampus and reticular formation. The tissues may be obtained from postmortem brain specimens or live patients.

Databases

The present invention includes relational databases containing sequence information, for instance for the genes of Tables 4-6, as well as gene expression information in various tissue samples, including brain and blood samples. Databases may also contain information associated with a given sequence or tissue sample such as descriptive information about the gene associated with the sequence information, or descriptive information concerning the clinical status of the tissue sample, or the patient from which the sample was derived. The database may be designed to include different parts, for instance a sequences database and a gene expression database. Methods for the configuration and construction of such databases are widely available, for instance, see Akerblom et al., (1999) U.S. Pat. No. 5,953,727, which is herein incorporated by reference in its entirety.

A database of the invention may include gene expression information for about 2, 3, 4, 5, 6, 7, 8, 9, 10, 15, 20, 25, 30, 50, 75, 100, 200, 500, 1000 or more genes, wherein the gene expression information is from diseased brain tissues or controls as described herein.

The databases of the invention may be linked to an outside or external database. In a preferred embodiment, as described in Tables 4-6, the external database is GenBank and the associated databases maintained by the National Center for Biotechnology Information (NCBI).

Any appropriate computer platform may be used to perform the necessary comparisons between sequence information, gene expression information and any other information in the database or provided as an input. For example, a large number of computer workstations are available from a variety of manufacturers, such has those available from Silicon Graphics. Client-server environments, database servers and networks are also widely available and appropriate platforms for the databases of the invention.

The databases of the invention may be used to produce, among other things, electronic Northerns to allow the user to determine the cell type or tissue in which a given gene is expressed and to allow determination of the abundance or expression level of a given gene in a particular tissue or cell.

The databases of the invention may also be used to present information identifying the expression level in a tissue or cell of a set of genes comprising at least one gene in Tables 4-6 comprising the step of comparing the expression level of at least one gene in Tables 4-6 in the tissue to the level of expression of the gene in the database. Such methods may be used to predict the physiological state of a given tissue by comparing the level of expression of a gene or genes in Tables 4-6 from a sample to the expression levels found in tissue from normal brain and brain of Parkinson's Disease patients. Such methods may also be used in the drug or agent screening assays as described below.

Detection Reports

As described above, the methods, databases and computer systems of the invention can be used to produce, deliver and/or send a detection or diagnosis report. The detection report of the invention typically comprises information or data related to the results of the practice of a method of the invention. For instance, the practice of a method of identifying genes associated with Parkinson's Disease as herein described may result in the preparation or production of a report describing the results of the method. The report may comprise information related to the candidate genes predicted by the comparison of at least one diseased sample to at least one normal sample. The report may also present information concerning the nucleic acid hybridization data, such as the integrity of the data as well as information inputted by the user of the database and methods of the invention, such as information used to annotate the nucleic acid hybridization data. As described elsewhere in this specification, the report may be generated by a server or computer system to which is loaded nucleic acid hybridization data by a user. The report related to that nucleic acid data may be generated and delivered to the user via remote means such as a password secured environment available over the internet or via available computer communication means such as email.

Antibody-Based Detection Methods

The present invention also employs methods for detecting the translation products of the genes listed in Tables 4-6 in clinical samples such as those described herein. For example, the present invention provides blood-based assays for diagnosing Parkinson's Disease by detecting the level of one or more proteins (encoded by genes in Tables 4-6) present in the blood. Numerous antibody-based detection formats are well known in the art, and include ELISA, radioimmunoassays, immunoblots, Western blots, flow cytometry, immunofluorescence, immunoprecipitation, and other related techniques. The antibodies may be provided in a diagnostic kit that incorporates at least one of these procedures to detect the translation products of the genes described herein as being differentially expressed in PD. The kit may contain other components, packaging, instructions, or other material to aid the detection of the protein and use of the kit.

In this aspect of the invention, the method may include a step of comparing the level of the PD biomarker expression in a clinical sample to a baseline level (also known as a control level) of biomarker expression. According to the present invention, a "baseline level" is a control level, and in some embodiments a normal or non-PD level. Therefore, it can be determined, based on the control or baseline level of biomarker expression, whether a sample to be evaluated for PD has a measurable increase, decrease, or substantially no change in biomarker expression, as compared to the baseline level. In certain embodiments, the baseline can be indicative of a particular stage of PD which will allow a patient's sample to be "staged." In yet another embodiment, the baseline level can be established from a previous sample from the patient being tested, so that the disease state of a patient can be monitored over time and/or so that the efficacy of a given therapeutic protocol can be evaluated over time.

The method for establishing a baseline level of biomarker expression or activity is selected based on the sample type, the tissue or organ from which the sample is obtained, the status of the patient to be evaluated, and, as discussed above, the focus or goal of the assay (e.g., diagnosis, staging, monitoring). Preferably, the method is the same method that will be used to evaluate the sample in the patient. In one embodiment, when the goal of the assay is diagnosis of PD, it is desirable to take the control sample from a population of cells, a tissue or a bodily fluid which is believed to represent a "normal" cell, tissue, or bodily fluid.

Various immunoassays known in the art can be used in conjunction with the present invention, including but not limited to, competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

Drug Screening

As described above, the genes and gene expression information provided in Tables 4-6 may be used as diagnostic markers for the prediction or identification of PD. For instance, a clinical sample from a patient may be assayed by any of the methods described above, and the expression levels from a gene or genes from Tables 4-6, may be compared to the expression levels found in non-diseased samples, and/or expression levels found in samples from Parkinson's Disease patients. Comparison of the expression data, as well as available sequence or other information may be done by researcher or diagnostician or may be done with the aid of a computer and databases as described above.

As described above, the genes and gene expression information provided in Tables 4-6 may also be used as markers for the monitoring PD progression, for instance, the development of Parkinson's Disease. For instance, a brain tissue sample or other sample from a patient may be assayed by any of the methods described above, and the expression levels in the sample from a gene or genes from Table 4 may be compared to the expression levels found in normal and tissue of Parkinson's Disease. Comparison of the expression data, as well as available sequence or other information may be done by researcher or diagnostician or may be done with the aid of a computer and databases as described above.

According to the present invention, the genes identified in Tables 4-6 may also be used as markers to evaluate the effects of a candidate drug or agent on a cell, particularly a Parkinson's Disease cell or tissue sample. A candidate drug or agent can be screened for the ability to simulate the transcription or expression of a given marker or markers (drug targets) or to down-regulate or counteract the transcription or expression of a marker or markers. According to the present invention, one can also compare the specificity of drugs' effects by looking at the number of markers which the drugs have and comparing them. More specific drugs will have fewer transcriptional targets. Similar sets of markers identified for two drugs indicates a similarity of effects.

Assays to monitor the expression of a marker or markers as defined in Tables 4-6 may utilize any available means of monitoring for changes in the expression level of the nucleic acids of the invention. As used herein, an agent is said to modulate the expression of a nucleic acid of the invention if it is capable of up- or down-regulating expression of the nucleic acid in a cell.

In one assay format, gene chips containing probes to at least two genes from Tables 4-6 may be used to directly monitor or detect changes in gene expression in the treated or exposed cell as described in more detail above. In another format, cell lines that contain reporter gene fusions between the open reading frame and/or the 3' or 5' regulatory regions of a gene in Tables 4-6 and any assayable fusion partner may be prepared. Numerous assayable fusion partners are known and readily available including the firefly luciferase gene and the gene encoding chloramphenicol acetyltransferase (Alam et al., (1990) Anal. Biochem. 188, 245-254). Cell lines containing the reporter gene fusions are then exposed to the agent to be tested under appropriate conditions and time. Differential expression of the reporter gene between samples exposed to the agent and control samples identifies agents which modulate the expression of the nucleic acid.

Additional assay formats may be used to monitor the ability of the agent to modulate the expression of a gene identified in Tables 4-6. For instance, as described above, mRNA expression may be monitored directly by hybridization of probes to the nucleic acids of the invention. Cell lines are exposed to the agent to be tested under appropriate conditions and time and total RNA or mRNA is isolated by standard procedures such those disclosed in Sambrook et al., (1989) Molecular Cloning—A Laboratory Manual, Cold Spring Harbor Laboratory Press).

In another assay format, cells or cell lines are first identified which express the gene products of the invention physiologically. Cell and/or cell lines so identified would be expected to comprise the necessary cellular machinery such that the fidelity of modulation of the transcriptional apparatus is maintained with regard to exogenous contact of agent with appropriate surface transduction mechanisms and/or the cytosolic cascades. Such cell lines may be, but are not required to be, derived from brain tissue. Further, such cells or cell lines may be transduced or transfected with an expression vehicle (e.g., a plasmid or viral vector) construct comprising an operable non-translated 5'-promoter containing end of the structural gene encoding the instant gene products fused to one or more antigenic fragments, which are peculiar to the instant gene products, wherein said fragments are under the transcriptional control of said promoter and are expressed as polypeptides whose molecular weight can be distinguished from the naturally occurring polypeptides or may further comprise an immunologically distinct tag. Such a process is well known in the art (see Sambrook et al., (1989) Molecular Cloning—A Laboratory Manual, Cold Spring Harbor Laboratory Press).

Cells or cell lines transduced or transfected as outlined above are then contacted with agents under appropriate conditions; for example, the agent comprises a pharmaceutically acceptable excipient and is contacted with cells comprised in an aqueous physiological buffer such as phosphate buffered saline (PBS) at physiological pH, Eagles balanced salt solution (BSS) at physiological pH, PBS or BSS comprising serum or conditioned media comprising PBS or BSS and serum incubated at 37° C. Said conditions may be modulated as deemed necessary by one of skill in the art. Subsequent to contacting the cells with the agent, said cells will be disrupted and the polypeptides of the lysate are fractionated such that a polypeptide fraction is pooled and contacted with an antibody to be further processed by immunological assay (e.g., ELISA, immunoprecipitation or Western blot). The pool of proteins isolated from the "agent-contacted" sample will be compared with a control sample where only the excipient is contacted with the cells and an increase or decrease in the immunologically generated signal from the "agent-contacted" sample compared to the control will be used to distinguish the effectiveness of the agent.

Another embodiment of the present invention provides methods for identifying agents that modulate the levels, concentration or at least one activity of a protein(s) encoded by the genes in Tables 4-6. Such methods or assays may utilize any means of monitoring or detecting the desired activity.

In one format, the relative amounts of a protein of the invention between a cell population that has been exposed to the agent to be tested compared to an unexposed control cell population may be assayed. In this format, probes such as specific antibodies are used to monitor the differential expression of the protein in the different cell populations. Cell lines or populations are exposed to the agent to be tested under appropriate conditions and time. Cellular lysates may be prepared from the exposed cell line or population and a control, unexposed cell line or population. The cellular lysates are then analyzed with the probe, such as a specific antibody.

Agents that are assayed in the above methods can be randomly selected or rationally selected or designed. As used herein, an agent is said to be randomly selected when the agent is chosen randomly without considering the specific sequences involved in the association of the a protein of the invention alone or with its associated substrates, binding partners, etc. An example of randomly selected agents is the use a chemical library or a peptide combinatorial library, or a growth broth of an organism.

As used herein, an agent is said to be rationally selected or designed when the agent is chosen on a nonrandom basis which takes into account the sequence of the target site and/or its conformation in connection with the agents action. Agents can be rationally selected or rationally designed by utilizing the peptide sequences that make up these sites.

For example, a rationally selected peptide agent can be a peptide whose amino acid sequence is identical to or a derivative of any functional consensus site.

The agents of the present invention can be, as examples, peptides, small molecules, vitamin derivatives, as well as carbohydrates. Dominant negative proteins, DNA encoding these proteins, antibodies to these proteins, peptide fragments of these proteins or mimics of these proteins may be introduced into cells to affect function. "Mimic" as used herein refers to the modification of a region or several regions of a peptide molecule to provide a structure chemically different from the parent peptide but topographically and functionally similar to the parent peptide (see Grant, (1995) in Molecular Biology and Biotechnology Meyers (editor) VCH Publishers). A skilled artisan can readily recognize that there is no limit as to the structural nature of the agents of the present invention.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

EXAMPLES

Methods

Subjects and Biological Samples

Postmortem brain tissue was obtained from 21 brain areas in two groups of Caucasian subjects diagnosed with neuropathologically confirmed PD (n=22) or aged individuals with no history or pathological diagnosis of neurologic or psychiatric disease (n=23). All subjects consented during life to donate their brain after death to the University of Miami/NPF Brain Endowment Bank (UM/BEB). All subjects completed either a disease (PD and other movement disorders) or aged control registry form (normal, aged donors) providing information about demographics, clinical diagnosis, medications, environmental and drug and alcohol exposures, personal and family history, and activities of daily living. Yearly updates on all brain donors were obtained until death. Medical and hospital records were collected on an annual basis and all pertinent information was entered into a database. The clinical and pathological diagnosis of PD was based on the UK PD Society Brain Bank diagnostic criteria (9) and the severity of PD at death was assessed using the Hoehn and Yahr (HY) scale (10). All clinical records were reviewed by a movement disorders specialist (S.P.) to ensure that subjects met diagnostic criteria.

An agonal-state questionnaire (25 items) provided information about the events 48 h prior to death (time, date, place and cause of death, treating physician, mean 48 h axillary temperature, presence and type of infection, co-morbidities, medication, presence of feeding tube, catheters, IV lines, PEG, oxygen, state of feeding and activity and DNR status). This information was completed by the treating physician or nurse immediately after death and was used for exclusion of patients with prolonged agonal states or death related events that are known to influence RNA quality (i.e. prolonged hypoxia or intubation). Although death certificates on all patients were available, they were not used as a source of information since they can introduce significant bias in PD (11). Since agonal state may affect the RNA expression profile of postmortem brain tissue, care was taken to match subject groups as closely as possible for age, gender, PMI, and brain pH.

Regional samples of postmortem brain were taken from frozen coronal blocks based on surface landmarks and cytoarchitectural landmarks. The regional analysis included 21 different brain regions (substantia nigra, ventral tegmental area, cingulate cortex (BA35), insular cortex, amygdala, nucleus basalis, caudate, putamen, nucleus accumbens, globus pallidus, mediodorsal thalamus, pulvinar, subthalamic nucleus, nucleus ambiguous, cerebellar hemisphere, anterior cerebellar vermis, dorsal raphe, locus ceruleus, hypothalamus, hippocampus and reticular formation).

Microarray Experiments

Total RNA isolation and biotin-labeled cRNA synthesis were performed by Gene Logic Inc. (Gaithersburg, Md.) using a TriZol method and RNEasy columns, according to Affymetrix (Santa Clara, Calif.) specifications from 50 mg of each regional sample. Extractions of RNA used in the present study had a minimum A260/A280 ratio of more than 1.9. The samples were further checked for evidence of degradation and integrity. Samples had a minimum 28S/18S ratio of more than 1.6 (2100 Bioanalyzer; Agilent Technologies, Palo Alto, Calif.). We used the Human Genome U133 Plus 2.0 Gene-Chip array with 54,000 probe sets representing more than 47,000 transcripts derived from approximately 38,500 well-substantiated human genes (Affymtrix). GeneChip analysis was performed with Microarray Analysis Suite version 5.0, Data Mining Tool 2.0, and Microarray database software (Affymetrix). The genes represented on the GeneChip were globally normalized and scaled to a signal intensity of 100.

The different measures of microarray RNA integrity are shown for the substantia nigra in Table 1. The same values were compared in all 21 regions to filter samples for quality control to meet criteria for inclusion in the final analysis. Microarray quality control parameters included the following: noise (RawQ), consistent number of genes detected as present across arrays, consistent scale factors, and consistent β-actin and glyceraldehyde-3-phosphate dehydrogenase 5'/3' signal ratios.

Data Analysis

We performed a gene expression survey for each of the 21 individual regions comparing end-stage PD patients and normal aged individuals. From a total of 945 samples obtained from the 21 brain regions from PD brain donors (n=22) and normal aged controls (n=23), a total of 499 (52.8%) passed the microarray brain quality control were used in the final expression data analysis. The total number of samples per region per subject is presented as a tilling chart and is shown in FIG. 1. We selected genes for analysis on the basis of "present calls" by Microarray Analysis Suite 5.0. In the present study, for a gene to be included, it had to be present (detectable) in at least 75% of the subjects to reduce the chances of false-positive findings. Expression data were analyzed using Genesis (GeneLogic, Gaithersburg, Md.) and AVADIS software (Strand Genomics, Redwood City, Calif.). Gene expression values were floored to 1 and then log2-transformed. One-way analysis of variance was performed for each gene to identify statistically significant gene expression changes. Two criteria were used to determine whether a gene was differentially expressed. The cutoffs for inclusion were a 1-way analysis of variance p value ≦0.01 and a fold-change (FC) of ±1.3.

Target Validation

Cases included in the microarray analysis were used for the quantitative real-time polymerase chain reaction (RT-PCR) for selected target validation. For validation of the top candidate gene, we blindly selected two regions (caudate and insula) for RT-PCR experiments. Three housekeeping genes (beta actin, GAPDH and cyclophilin) were used to generate a normalization factor for quantitative comparisons across groups (PD n=22 and aged controls n=23).

Total RNA was isolated using the TriZol reagent (Invitrogen, Carlsbad, Calif.) according to the manufacturer's instructions. The concentration of RNA was determined by spectrophotometry, using GeneQuant II (Amersham Biosciences, Uppsala, Sweden). Reverse transcription was performed with SuperScript™ First-Strand Synthesis System (Invitrogen). Real-time PCR reactions were run in 96-well PCR plates using an ABI Prism 7300 sequence detection system (Applied Biosystems, Foster City, Calif.). Each 50 µl reaction contained cDNA template generated from RNA, 900 nM of gene specific primers for MRPS6 (5'-ATGG-GATCTCTGCCC CAGTCA-3', [SEQ ID NO:29] and 5'-CAAGTGCTCACCATGCTTT-3' [SEQ ID NO:30]), 250 nM probe (5'-FAM TTTTTATGCACCCACCGCAGC-3' [SEQ ID NO:31]) and Taqman Universal PCR Master Mix (Applied Biosystems) containing Hot Goldstar DNA Polymerase, dNTPs, uracil-N-glycosylase, and passive reference. PCR cycle was run at 50° C. for 2 min, 95° C. for 10 min, 40 cycles of 95° C. for 15 sec, and 60° C. for 1 min. At the end of PCR cycling steps, data were collected by the Sequence Detector Software (SDS version 2.1, Applied Biosystems). All measurements were performed in triplicates and the gene expression levels calculated as an average of triplicates. To normalize the intersample variation associated with RNA preparation, 3 housekeeping genes (cyclophilin, β-actin and glyceraldehyde-3-phosphate dehydrogenase) were quantified for all samples to obtain the normalization factor using a Visual Basic Application (VBA) for MS Excel termed geNorm as described in (12).

Additional Target Validation

Real-time RT-PCR was performed for MRPS6, CHORDC1, PRKCAB, and SLC38A2 using brain tissue from the substantia nigra and amygdale of 15 Parkinson's Disease human post-mortem brains. The gene expression of these genes from the PD patients was compared to that of eight control subjects. This additional target validation was conducted in a different cohort of PD cases than those described above.

Total RNA was isolated using the TriZol reagent (Invitrogen, Carlsbad, Calif.) according to the manufacturer's instructions. The concentration of RNA was determined by spectrophotometry, using Nanodrop-1000 (Nanodrop Technologies, Wilmington, D.C.). Reverse transcription was performed with a High-Capacity cDNA Reverse Transcription kit using random primers from Applied Biosystems (Foster City, Calif.). Gene expression levels were measured in each sample by real-time PCR using the ABI 7900HT Thermocycler. Expression levels were normalized with respect to an internal reference 18S rRNA. All samples were run in triplicate. cDNA was amplified with the Taqman Universal PCR master mix reagent (Applied Biosystems, Foster City, Calif.) using the following cycling parameters: 2 minutes at 50° C., 10 minutes at 95° C., 40 cycles: 15 seconds at 95° C. and 1 minute at 60° C. The target cDNA from MRPS6, CHORDC1, PRKCAB, and SLC38A2 was amplified using ABI MGB probe and primer set assay IDs Hs00606808_m1, Hs00854389_g1, and Hs00255854_m1, respectively and normalized with respect to the 18S rRNA control (ABI MGB probe and primer set assay ID Hs99999901_s1). Data was analyzed using software RQ manager 1.2 from Applied Biosystems (Foster City, Calif.).

Gene Expression in Blood

Real-time RT-PCR was also performed to measure the expression of MRPS6 and SLC5A3 in blood samples from three Parkinson's Disease patients and three control subjects. The expression of MRPS6 and SLC5A3 was normalized with respect to four known housekeeping genes, 18S rRNA, B2M, ACTB, and HPRT1. However, only HPRT1 was not disregulated in PD blood, and therefore, it was used as the standard housekeeping gene. Gene expression for CHORDC1, PRKACB, and SLC38A2 in blood were also measured.

Results

Figure 2:
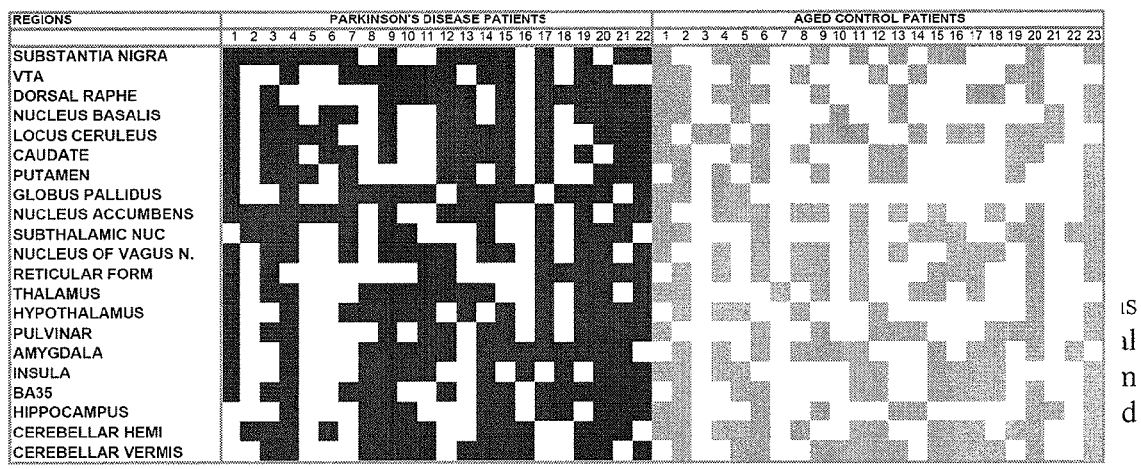
FIG. 2 is the regional brain sample tiling chart. Columns represent gene chips from individual subjects and rows represent gene chips used per regional comparison. Data from a total of 499 gene chips (283 from 22 PD patients and 216 from 23 aged control subjects) and from 21 regions passed RNA and microarray quality control and were used is our analysis.

The RNA quality parameters for all subjects are shown in Table 1 for two blindly selected regions (insula and caudate—also used for RT-PCR validation) and the substantia nigra. Analysis of the quality control parameters showed no significant differences in age, brain pH, post mortem interval or RNA QC values between aged control and PD groups. Table 2 lists the demographic information, age at death, cause of death, PMI and brain pH values for PD and control subjects. These results demonstrate the subjects were well matched on these variables, including the number of individuals with sudden versus prolonged terminal cause of death. The clinical characteristics of the PD subjects included in the gene expression survey are summarized in Table 3. All PD subjects had advanced disease with H&R stage of 4.5±0.7. Consistent with previous reports, RNA quality control parameters showed no effect of PMI even in a brain region that is one of the most severely affected with advanced disease (FIG. 2).

Figure 3:
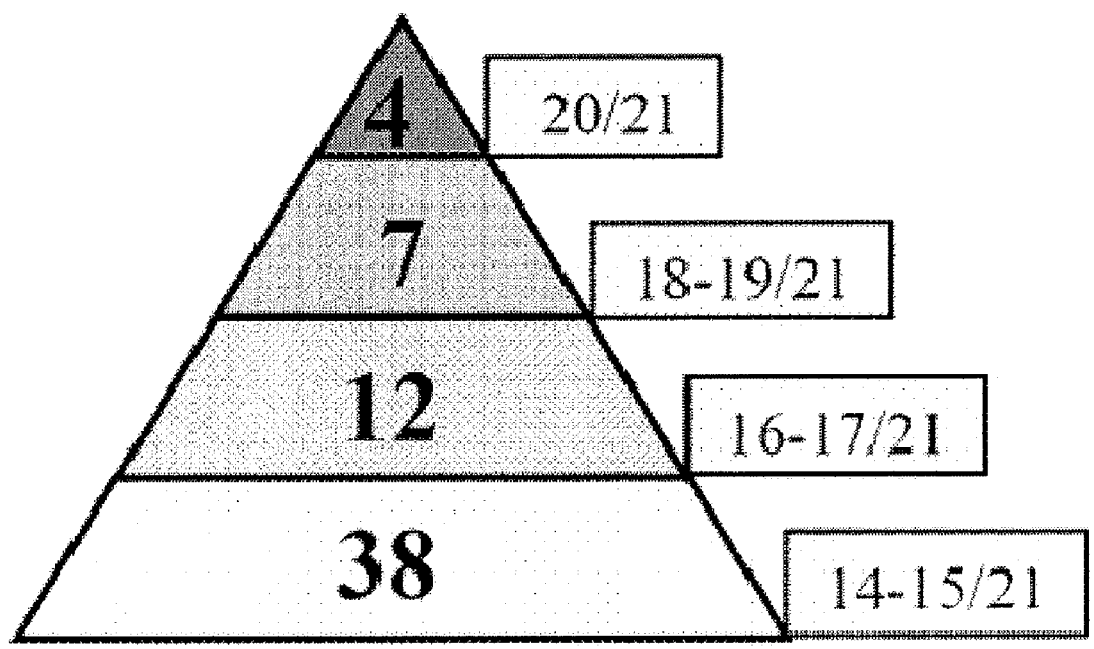
FIG. 3 is a frequency pyramid showing the number of candidate genes (number inside pyramid) significantly regulated according to the number of brain regions (shown in rectangular box). Four genes topped the pyramid. Details of these genes are presented in Table 4.

To reduce the number of comparisons and the chances of false positives, we conducted a multiregional survey to identify and cluster select genes that were significantly expressed across the different comparison regions. A frequency pyramid indicating the number of target brain regions in which these candidate genes were significantly expressed is shown in FIG. 3. A list of these top candidate genes associated with PD is presented (Table 4), together with biological function and chromosomal location (Table 5). In Table 6 lists these and other genes that are differentially expressed in PD, along with the GeneBank ID. The nucleotide sequences of these genes, which are in the public domain, are hereby incorporated by reference. Topping the list was MRPS6, a nuclear encoded mitochondrial ribosomal protein, that was significantly upregulated with a 2.1 mean fold change for 20 out of 21 regions ($p \leq 0.001$). The only brain region in which the MRPS6 was not differentially expressed was the hippocampus.

Gene Ontology analysis of the top candidate genes identified in the multiregional analysis suggests involvement of genes having to do with response to stress in end-stage disease, including STIP1 and CIRBP (Tables 4 and 5). Another gene of interest was the solute carrier family member 2 (SLC38A2), which functions to transport glutamine. This gene product was upregulated 1.7 fold in PD compared to control subjects. We observed in 18 of the 21 PD brain regions surveyed, a marked ~2 fold decrease for the cAMP dependent protein kinase, beta catalytic subunit (PRKACB). The gene has been implicated in a number of different cellular processes, including cell growth and death and long-term potentiation in the CNS.

Figure 4:
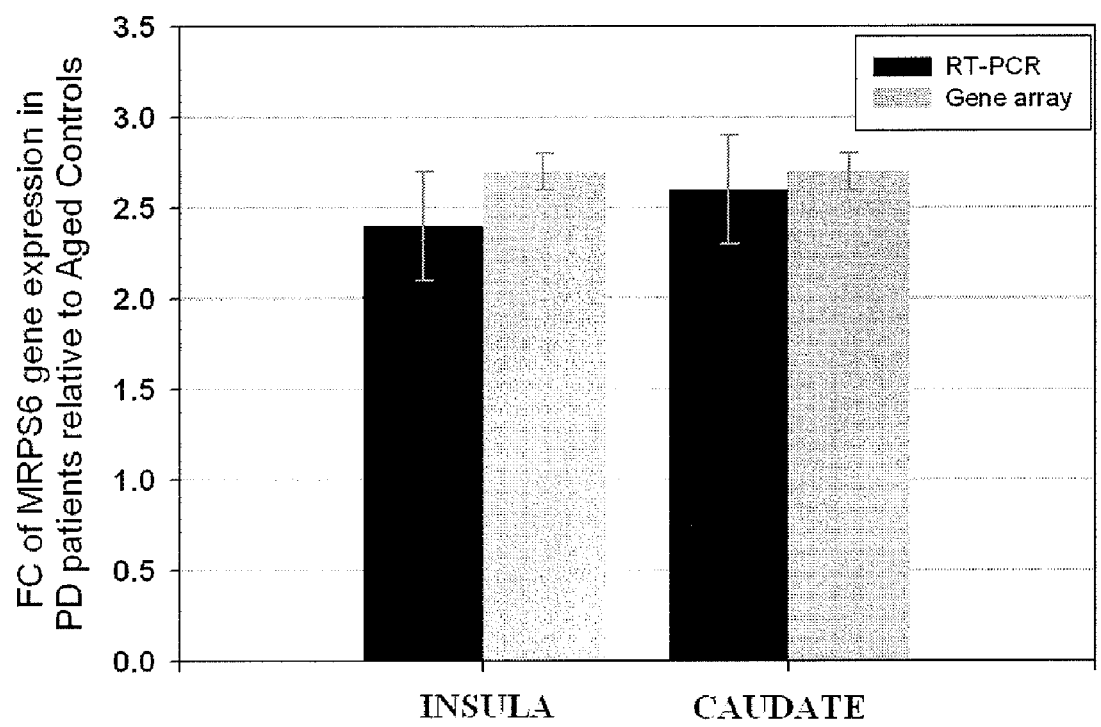
FIG. 4 shows the results of MRPS6 gene expression (fold change "FC") in PD patients versus normal aged controls: Gene array (caudate FC=2.7, SE=0.1 and insula FC=2.7, SE=0.1) and RT-PCR (caudate FC=2.6, SE=0.3 and insula FC=2.4, SE=0.3) methods produced similar levels of overexpression in 2 blindly selected regions (insula and caudate). Results of the comparisons of MRPS6 expression between groups were statistically significant (p<0.01) in both regions with both methods.

The expression levels of MRPS6 was confirmed by quantitative RT-PCR analyses in 2 selected regions (caudate nucleus and insula). The validation results are presented in FIG. 4. We used three control genes (GAPDH, beta actin and cyclophilin) to normalize expression data for MRPS6. The correlation between the microarray and RT-PCR data using the three controls genes for RT-PCR were consistent for this gene product (data not shown). Analysis of the MRPS6 gene in PD patients compared to normal aged controls was of the same order of magnitude as seen from the microarray experiments. The fold-change values determined from microarray (caudate FC=2.7±0.1 and insula FC=2.7±0.1) were in good agreement with expression levels determined by RT-PCR (caudate FC=2.6±0.3 and insula FC=2.4±0.3) methods. These results demonstrate that the differential expression of MRPS6 was confirmed by both methods on independent samples from the same individuals.

Figure 5:
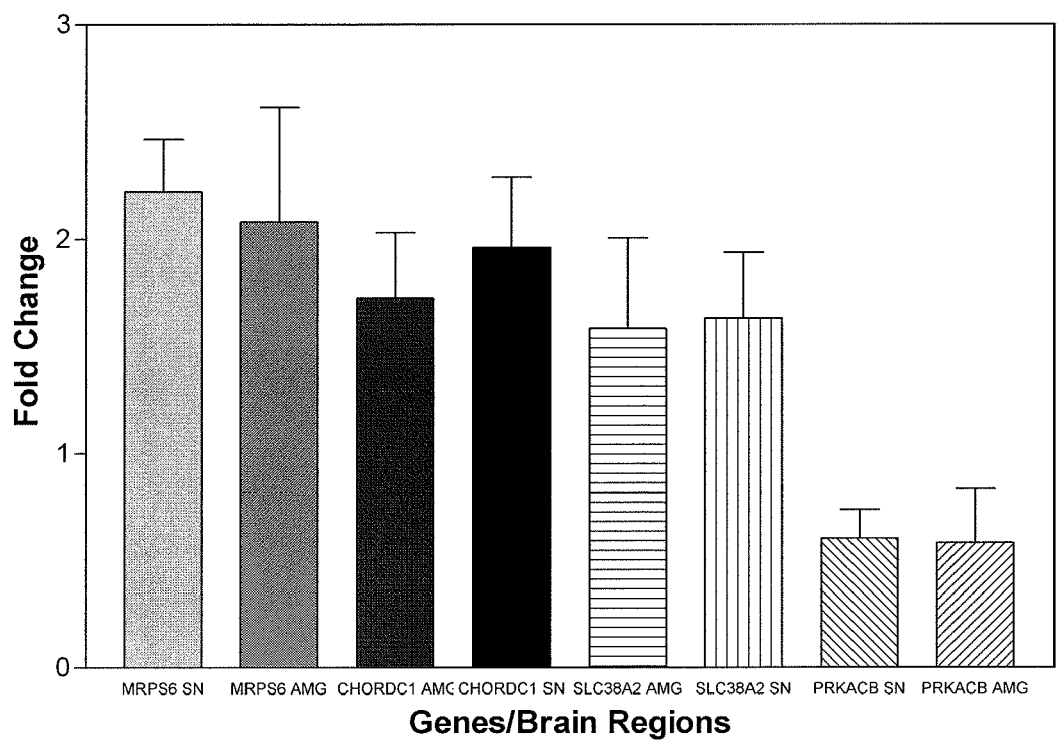
FIG. 5 shows the fold change in expression of MRPS6, CHORDC1, PRKACB, and SLC38A2 in the Amygdala and Substantia Niagra of post-mortem PD patients versus normal aged controls as determined by real-time RT-PCR.

Additional target validation was performed using real-time RT-PCR to measure the gene expression of MRPS6, CHORDC1, PRKACB, and SLC38A2 in the substantia nigra and amygdala from a different cohort of PD cases. Significantly higher levels of expression for MRPS6, CHORDC1, and SLC38A2 were observed in the substantia nigra and amygdala of the PD post-mortem brain (FIG. 5). In contrast, the levels of expression for PRKACB were significantly lower in the substantia nigra and amygdala of the PD post-mortem brain. These results are identical to those derived from gene expression studies from the other cohort run on the Affymetrix U133 Plus 2 gene chip.

Figure 6:
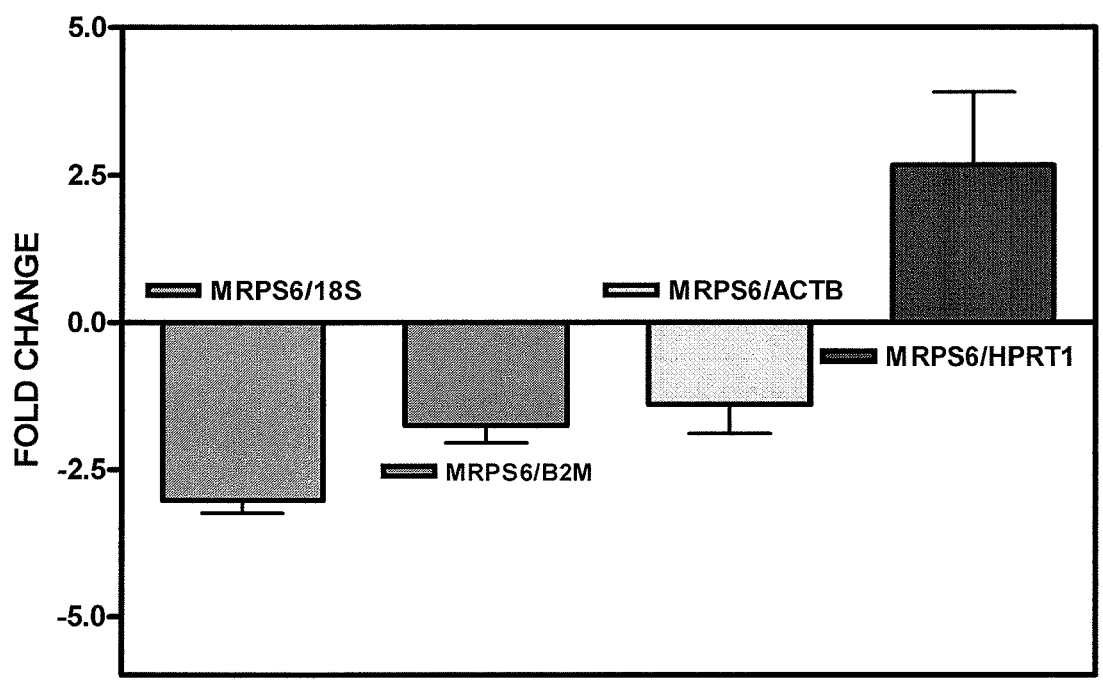
FIG. 6 shows the fold change in gene expression of MRPS6 in blood from three PD patients versus that from blood of three control patients, as measured by RT-PCR. The expression of MRPS6 was normalized with respect to four known housekeeping genes, 18S rRNA, B2M, ACTB, and HPRT1. However, only HPRT1 was not disregulated in PD blood, and therefore, it was used as the standard housekeeping gene.
Figure 7:
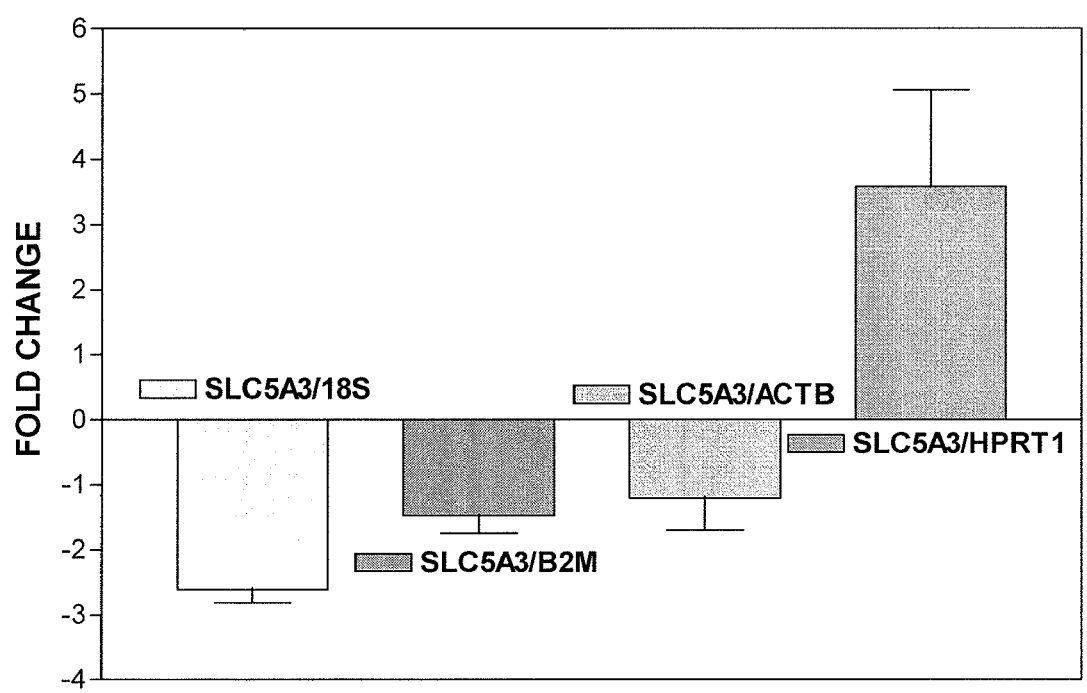
FIG. 7 shows the fold change in gene expression of SLC5A3 in blood from three PD patients versus that from blood of three control patients, as measured by RT-PCR. The expression of SLC5A3 was normalized with respect to four known housekeeping genes, 18S rRNA, B2M, ACTB, and HPRT1. As described in FIG. 6, only HPRT1 was not disregulated in PD blood. Thus, it was used as the standard housekeeping gene.

Gene expression was also measured in blood. As indicated in FIGS. 6 and 7, the expression of MRPS6 and SLC5A3 was significantly higher in blood samples from PD patients in comparison to control subjects. These results demonstrate that a correlation exists between the expression of genes in brain tissue and blood samples from patients with Parkinson's Disease, and indicate that blood testing can be used to detect genes associated with Parkinson's Disease.

Discussion

Gene expression profiling is done usually on a few select brain regions, providing a measurement of transcript numbers at a particular point in the sequence of a continuing process. The expression levels of specific gene transcripts in postmortem brain tissues may be either 'state' or 'trait' dependent, reflecting a complex interplay of disease relevant changes in cellular processes, structure and function. This report provides the first extensive multiregional gene expression profiling survey in PD, to identify common transcripts that are regulated reproducibly throughout a large number of the total number of brain regions surveyed.

Using this unbiased approach, we have identified MRPS6 as a top candidate gene associated with PD. MRPS6 was significantly upregulated in 20 out of 21 regions studied approximately three-fold that of normal aged controls. The original MRPS6 frag, 212944_at, is now called SLC5A3 (the solute carrier family 5 member 3 gene). SLC5A3 corresponds to Fragment IDs. 212944_at and 1553313_s_at. The expression levels of MRPS6, represented by Fragment IDs 213164_at and 224919_at, in PD were confirmed by quantitative RT-PCR. A total of 3 other high probability genes were differentially expressed in addition to the MRPS6, including the histone 1 (H1ST1H2BD), RNA binding motif protein 3 (RBM3), and solute carrier family 38, member 2 (SLC38A2), a sodium-coupled glutamine transporter (13) in 20 out of 21 regions surveyed. Other genes of interest that were regulated throughout most of the brain regions surveyed were the cysteine and histidine-rich containing zinc binding protein 1 (CHORDC1), the cold inducible RNA binding protein (CIRBP), a heat shock protein 90-interacting protein (14), cAMP dependent protein kinase, beta catalytic subunit PRKACB (PKBACB), and a stress-induced phosphoprotein (STIP1).

Mitochondrial dysfunction caused either by genetic defects (i.e. PINK1 and DJ1 mutations) and/or environmental factors (MPTP, rotenone or paraquat toxicity) causes parkinsonism in vivo in mice and primate models (1, 15). PD is a multisystem disorder that affects autonomic, limbic and somatomotor systems with advanced disease staging. Our finding of increased expression of MRPS6 in PD patients may be associated with a disorder of energy metabolism with development of PD-related pathology.

Nuclear MRP genes are associated with mitochondrial disease (20, 21). It is estimated that there are about 100 different human mitochondrial ribosomal proteins (16) all of which are encoded by nuclear genes (17). They are essential building blocks for the 55S mammalian mitochondrial ribosome, which translates mitochondrial mRNAs for the 13 essential components of the OXPHOS (17). The mammalian mitoribosome differs significantly from the ancestral 70S ribosome (18) in that it has lost it has lost nearly half the RNA present in bacterial mitoribosomes and gained "extra" proteins (MRPs) (19), which can have additional properties (multifunctional) and have been implicated, among others, in apoptosis and cellular degeneration (20).

Since mitochondrial ribosomes are responsible for translating the 13 mRNAs for essential proteins of the OXPHOS, mutations in these proteins have significant consequences. Several of the MRP genes map to chromosomal loci associated with neurological/neurodegenerative diseases (17). These range from mild, late-onset disorders, such as age-related sensorineural hearing impairment or ocular myopathy (PEO), to devastating and usually fatal infantile disorders, such as Leigh syndrome (also known as fatal necrotizing encephalopathy) (21). MRPs have been linked also to diseases affecting specific neuronal populations including non-syndromic hearing loss (22), spinocerebellar ataxia with blindness and deafness (6p23-p21) (17), Usher Syndrome, type 1E (21q21) (23), Leigh Syndrome (9q34, 11q13, 19p13.3, and 5q11) (24), Russell-Silver Syndrome (7p11.2, 17q23-q24) (25), the Stuve-Wiedemann Syndrome (1p34) (26) and the multiple mitochondrial dysfunctions syndrome (2p14-p13) (27).

Mitochondrial dysfunction plays a key role in many signaling pathways leading to cell death (28, 29). The precise mechanisms underlying the role of mitochondria in apoptosis (30) and the number of proteins involved remain unclear (31). Recently, MRPS29 shares sequence homology with death-associated protein 3 (DAP3) (32-35). DAP3 is a GTP binding protein that mediates interferon-, tumor necrosis factor- and FAS-induced cell death (20). When over-expressed, it causes apoptosis in a number of different types of mammalian cells (33, 34). Although its precise role in the induction of cell death is not known, it functions downstream of the death-inducing signaling complex, but upstream of the some members of the caspase family (33, 34). A second pro-apoptotic protein of unknown function is programmed cell death protein 9 (PDCD9 or p52) (designated MRP-S30) (20). Yoo et al. (36), demonstrated that the mitoribosomal protein MRPL41 enhances p53 stability and contributes to p53-induced apoptosis in response to growth-inhibitory conditions. The tumor suppressor p53 is a key regulator of both the cell cycle and cell proliferation (36). The p53 protein is a potent transcription factor, which activates target genes, and triggers growth arrest, DNA repair, or apoptosis in response to cellular genotoxic stresses (37, 38). MRPL41 protein enhances the translocation of p53 to the mitochondria, thereby inducing apoptosis. While the function of MRPS6 is at present unknown, the link to pro-apoptotic mechanisms demonstrated for other members of the mitoribosomal family makes this protein a potentially relevant gene target for PD pathophysiology.

The expression of the β catalytic subunit of cAMP-dependent protein kinase (PRKACB) gene was significantly downregulated in our multiregional comparisons between PD subjects and normal, aged controls. PRKACB regulates the function of the neurotrophin receptor p75 by phosphorylation (39). Several p75 neurotrophin receptor mediated activities have been proposed, including enhancement of axonal outgrowth (40, 41) and modulating dopaminergic synaptic transmission (42). A recent report suggests metaplasticity of the late-phase of long-term potentiation includes a crictical role for cAMP/protein kinase A signaling (REF). A disruption in this pathway in advanced PD, might suggest a loss of input specific synaptic facilitation and relative imbalance due to loss of protein kinase A activity. Another gene of interest identified in our study is the solute carrier family 38, member 2 (SLC38A2), a sodium-coupled glutamine transporter. SLC28A2 is thought to be involved in the glutamate-glutamine cycle (13). Glutamate released into the extracellular space is cleared by glutamate transporters (expressed in neuronal cells and glial cells), terminating neurotransmission. Glutamate is converted to glutamine by glutamine synthetase (43) and then re-released through glutamine transporters, like SLC38A2) (44) for uptake by glutaminergic neurons as an immediate precursor of glutamate (13). The upregulation of SLC38A2 may link this transporter with a dysregulation of glutaminergic pathways, consistent with the excitotoxic theory of neurodegeneration proposed for PD (45).

Additional findings of our multiregion, gene expression study are consistent with our current understanding of PD. Two of our top candidate genes (FUSIP1 and PRKACB) map near the chromosomal locus (1p36) which has shown significant linkage to PD and harbors three relevant loci: PARK6 (pink1) (46), PARK7 (dj1) (47) and PARK9 (unknown gene) (48). One more, SLC38A2 maps on the same region with PARK8 (LRRK2) (49). Recent evidence (PNAS 103(36) "13520-13525, 2006) suggests that a reduction in PINK1 function leads to a PD-associated neurodegeneration. Thus a reduction in two of our top genes, FUSIP1 and PRKACB, located on the same chromosomal location as PINK1 (1q36.1 and 0.11) might suggest a similar PD-associated neurodegeneration.

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein, will become apparent to those skilled in the art from the foregoing description and accompanying drawings using no more than routine experimentation. Such modifications and equivalents are intended to fall within the scope of the appended claims.

All publications, patents and patent applications mentioned in this specification are herein incorporated by reference into the specification to the same extent as if each individual publication, patent or patent application was specifically and individually indicated to be incorporated herein by reference.

Citation or discussion of a reference herein shall not be construed as an admission that such is prior art to the present invention.

REFERENCES

The disclosures of each and every patent, patent application, and publication cited herein including but not limited to the references listed immediately below are hereby incorporated herein by reference in their entirety.

1. Farrer M J. Genetics of Parkinson disease: paradigm shifts and future prospects. Nat Rev Genet 2006; 7:306-318.
2. Maraganore D M, de Andrade M, Lesnick T G, et al. High-resolution whole-genome association study of Parkinson disease. Am J Hum Genet 2005; 77:685-693.
3. Grunblatt E, Mandel S, Jacob-Hirsch J, et al. Gene expression profiling of parkinsonian substantia nigra pars compacta; alterations in ubiquitin-proteasome, heat shock protein, iron and oxidative stress regulated proteins, cell adhesion/cellular matrix and vesicle trafficking genes. J Neural Transm 2004; 111:1543-1573.

4. Hauser M A, Li Y J, Xu H, et al. Expression profiling of substantia nigra in Parkinson disease, progressive supranuclear palsy, and frontotemporal dementia with parkinsonism. Arch Neurol 2005; 62:917-921.

5. Mandel S, Grunblatt E, Riederer P, et al. Gene Expression Profiling of Sporadic Parkinson's Disease Substantia Nigra Pars Compacta Reveals Impairment of Ubiquitin-Proteasome Subunits, SKP1A, Aldehyde Dehydrogenase, and Chaperone HSC-70. Ann N Y Acad Sci 2005; 1053: 356-375.

6. Moran L B, Duke D C, Deprez M, Dexter D T, Pearce R K, Graeber M B. Whole genome expression profiling of the medial and lateral substantia nigra in Parkinson's Disease. Neurogenetics 2006; 7:1-11.

7. Zhang Y, James M, Middleton F A, Davis R L. Transcriptional analysis of multiple brain regions in Parkinson's Disease supports the involvement of specific protein processing, energy metabolism, and signaling pathways, and suggests novel disease mechanisms. Am J Med Genet B Neuropsychiatr Genet 2005; 137:5-16.

8. Ogden C A, Rich M E, Schork N J, et al. Candidate genes, pathways and mechanisms for bipolar (manic-depressive) and related disorders: an expanded convergent functional genomics approach. Mol Psychiatry 2004; 9:1007-1029.

9. Hughes A J, Daniel S E, Kilford L, Lees A J. Accuracy of clinical diagnosis of idiopathic Parkinson's Disease: a clinico-pathological study of 100 cases. J Neurol Neurosurg Psychiatry 1992; 55:181-184.

10. Hoehn M M, Yahr M D. Parkinsonism: onset, progression and mortality. Neurology 1967; 17:427-442.

11. Papapetropoulos S, Villar J M, Gonzalez J, Mash D C. Disparities in death certificates of Parkinson's Disease patients: A report from a population of brain donors. Mov Disord 2006.

12. Vandesompele J, De Preter K, Pattyn F, et al. Accurate normalization of real-time quantitative RT-PCR data by geometric averaging of multiple internal control genes. Genome Biol 2002; 3:RESEARCH0034.

13. Umapathy N S, Li W, Mysona B A, Smith S B, Ganapathy V. Expression and function of glutamine transporters SN1 (SNAT3) and SN2 (SNAT5) in retinal Muller cells. Invest Ophthalmol Vis Sci 2005; 46:3980-3987.

14. Wu J, Luo S, Jiang H, Li H. Mammalian CHORD-containing protein 1 is a novel heat shock protein 90-interacting protein. FEBS Lett 2005; 579:421-426.

15. Gandhi S, Wood N W. Molecular pathogenesis of Parkinson's Disease. Hum Mol Genet 2005; 14:2749-2755.

16. O'Brien T W. Properties of human mitochondrial ribosomes. IUBMB Life 2003; 55:505-513.

17. O'Brien T W, O'Brien B J, Norman R A. Nuclear MRP genes and mitochondrial disease. Gene 2005; 354:147-151.

18. Gray M W, Burger G, Lang B F. The origin and early evolution of mitochondria. Genome Biol 2001; 2:REVIEWS 1018.

19. Schieber G L, O'Brien T W. Extraction of proteins from the large subunit of bovine mitochondrial ribosomes under nondenaturing conditions. J Biol Chem 1982; 257:8781-8787.

20. Cavdar Koc E, Ranasinghe A, Burkhart W, et al. A new face on apoptosis: death-associated protein 3 and PDCD9 are mitochondrial ribosomal proteins. FEBS Lett 2001; 492:166-170.

21. Jacobs H T, Turnbull D M. Nuclear genes and mitochondrial translation: a new class of genetic disease. Trends Genet 2005; 21:312-314.

22. Sylvester J E, Fischel-Ghodsian N, Mougey E B, O'Brien T W. Mitochondrial ribosomal proteins: candidate genes for mitochondrial disease. Genet Med 2004; 6:73-80.

23. Chaib H, Kaplan J, Gerber S, et al. A newly identified locus for Usher syndrome type I, USH1E, maps to chromosome 21q21. Hum Mol Genet 1997; 6:27-31.

24. Dahl H H. Getting to the nucleus of mitochondrial disorders: identification of respiratory chain-enzyme genes causing Leigh syndrome. Am J Hum Genet 1998; 63:1594-1597.

25. Monk D, Bentley L, Hitchins M, et al. Chromosome 7p disruptions in Silver Russell syndrome: delineating an imprinted candidate gene region. Hum Genet 2002; 111: 376-387.

26. Chabrol B, Sigaudy S, Paquis V, et al. Stuve-Wiedemann syndrome and defects of the mitochondrial respiratory chain. Am J Med Genet 1997; 72:222-226.

27. Seyda A, Newbold R F, Hudson T J, et al. A novel syndrome affecting multiple mitochondrial functions, located by microcell-mediated transfer to chromosome 2p14-2p13. Am J Hum Genet 2001; 68:386-396.

28. Brenner C, Kroemer G. Apoptosis. Mitochondria—the death signal integrators. Science 2000; 289:1150-1151.

29. Gottlieb R A. Mitochondria: execution central. FEBS Lett 2000; 482:6-12.

30. Bernardi P, Scorrano L, Colonna R, Petronilli V, Di Lisa F. Mitochondria and cell death. Mechanistic aspects and methodological issues. Eur J Biochem 1999; 264:687-701.

31. Crompton M. The mitochondrial permeability transition pore and its role in cell death. Biochem J 1999; 341 (Pt 2):233-249.

32. Carim L, Sumoy L, Nadal M, Estivill X, Escarceller M. Cloning, expression, and mapping of PDCD9, the human homolog of Gallus gallus pro-apoptotic protein p52. Cytogenet Cell Genet 1999; 87:85-88.

33. Kissil J L, Cohen O, Raveh T, Kimchi A. Structure-function analysis of an evolutionary conserved protein, DAP3, which mediates TNF-alpha- and Fas-induced cell death. Embo J 1999; 18:353-362.

34. Kissil J L, Deiss L P, Bayewitch M, Raveh T, Khaspekov G, Kimchi A. Isolation of DAP3, a novel mediator of interferon-gamma-induced cell death. J Biol Chem 1995; 270: 27932-27936.

35. Sun L, Liu Y, Fremont M, et al. A novel 52 kDa protein induces apoptosis and concurrently activates c-Jun N-terminal kinase 1 (JNK1) in mouse C3H10T1/2 fibroblasts. Gene 1998; 208:157-166.

36. Yoo Y A, Kim M J, Park J K, et al. Mitochondrial ribosomal protein L41 suppresses cell growth in association with p53 and p27Kip1. Mol Cell Biol 2005; 25:6603-6616.

37. Giaccia A J, Kastan M B. The complexity of p53 modulation: emerging patterns from divergent signals. Genes Dev 1998; 12:2973-2983.

38. Jin A, Itahana K, O'Keefe K, Zhang Y. Inhibition of HDM2 and activation of p53 by ribosomal protein L23. Mol Cell Biol 2004; 24:7669-7680.

39. Higuchi H, Yamashita T, Yoshikawa H, Tohyama M. PKA phosphorylates the p75 receptor and regulates its localization to lipid rafts. Embo J 2003; 22:1790-1800.

40. Bentley C A, Lee K F. p75 is important for axon growth and schwann cell migration during development. J Neurosci 2000; 20:7706-7715.

41. Brann A B, Scott R, Neuberger Y, et al. Ceramide signaling downstream of the p75 neurotrophin receptor mediates the effects of nerve growth factor on outgrowth of cultured hippocampal neurons. J Neurosci 1999; 19:8199-8206.

42. Blochl A, Sirrenberg C. Neurotrophins stimulate the release of dopamine from rat mesencephalic neurons via Trk and p75Lntr receptors. J Biol Chem 1996; 271:21100-21107.
43. Riepe R E, Norenberg M D. Glutamine synthetase in the developing rat retina: an immunohistochemical study. Exp Eye Res 1978; 27:435-444.
44. Mackenzie B, Erickson J D. Sodium-coupled neutral amino acid (System N/A) transporters of the SLC38 gene family. Pflugers Arch 2004; 447:784-795.
45. Vernon A C, Palmer S, Datla K P, Zbarsky V, Croucher M J, Dexter D T. Neuroprotective effects of metabotropic glutamate receptor ligands in a 6-hydroxydopamine rodent model of Parkinson's Disease. Eur J Neurosci 2005; 22:1799-1806.
46. Valente E M, Abou-Sleiman P M, Caputo V, et al. Hereditary early-onset Parkinson's Disease caused by mutations in PINK1. Science 2004; 304:1158-1160.
47. Bonifati V, Rizzu P, van Baren M J, et al. Mutations in the DJ-1 gene associated with autosomal recessive early-onset parkinsonism. Science 2003; 299:256-259.
48. Williams D R, Hadeed A, al-Din A S, Wreikat A L, Lees A J. Kufor Rakeb disease: autosomal recessive, levodopa-responsive parkinsonism with pyramidal degeneration, supranuclear gaze palsy, and dementia. Mov Disord 2005; 20:1264-1271.
49. Zimprich A, Biskup S, Leitner P, et al. Mutations in LRRK2 cause autosomal-dominant parkinsonism with pleomorphic pathology. Neuron 2004; 44:601-607.

TABLE 1

Quality Control Parameters for Brain Sample Microarrays

| SN | Number | Age (yr) | β-Actin Ratio | GapDH Ratio | RNA QC | Present Calls |
|---|---|---|---|---|---|---|
| CTRL | 11 | 77.9 ± 13.09 | 0.33 ± 0.11 | 0.60 ± 0.14 | 0.46 ± 0.11 | 24296 ± 753.24 |
| PD | 16 | 75.1 ± 7.81 | 0.28 ± 0.09 | 0.58 ± 0.11 | 0.42 ± 0.09 | 24982 ± 837.18 |
| | | | Insula | | | |
| CTRL | 11 | 73.3 ± 4.02 | 0.35 ± 0.04 | 0.62 ± 0.04 | 0.48 ± 0.04 | 25633.9 ± 360.5 |
| PD | 12 | 72.2 ± 3.13 | 0.35 ± 0.03 | 0.66 ± 0.04 | 0.50 ± 0.03 | 24892.5 ± 582.5 |
| | | | Caudate | | | |
| CTRL | 14 | 60 ± 7.02 | 0.302 ± 0.04 | 0.625 ± −0.05 | 0.464 ± 0.04 | 24154.28 ± 546.5 |
| PD | 10 | 73 ± 3.07 | 0.31 ± 0.02 | 0.625 ± 0.047 | 0.45 ± 0.04 | 26259.44 ± 337.2 |

| | SN | % Present | RAWQ | Scale Factor | PMI |
|---|---|---|---|---|---|
| | CTRL | 44.4 ± 7.8 | 1.53 ± 0.08 | 2.00 ± 0.24 | 8.2 ± 2.1 |
| | PD | 45.5 ± 1.50 | 1.60 ± 0.23 | 1.85 ± 0.26 | 7.4 ± 1.6 |
| | | Insula | | | |
| | CTRL | 46.8 ± 6.8 | 1.74 ± 0.05 | 1.45 ± 0.07 | 9.3 ± 2.0 |
| | PD | 45.6 ± 1.2 | 1.53 ± 0.14 | 2.03 ± 0.29 | 7.5 ± 1.8 |
| | | Caudate | | | |
| | CTRL | 51.14 ± 7.2 | 1.63 ± 0.06 | 1.78 ± 0.18 | 10.2 ± 2.00 |
| | PD | 48.10 ± 6.6 | 1.61 ± 0.06 | 1.61 ± 0.13 | 6.9 ± 1.8 |

*Samples were obtained from the 2 blindly selected sample regions and the substantia nigra. RNA quality control parameters (including β-actin and GAPDH signal ratios) were consistent across chips. Values were derived from results of Microarray Analysis Suite version 5.0 analysis (available at: http://www.affymetrix.com).

TABLE 2

Demographic details, cause of death and RNA quality-determining parameters

| Code | Gender | Age at death | Cause of Death | PMI | Ph |
|---|---|---|---|---|---|
| C1 | M | 74 | Lung Cancer | 4 | 6.52 |
| C2 | F | 90 | Congestive Heart Failure | 5 | 6.08 |
| C3 | F | 90 | Respiratory Failure | 5 | 6.12 |
| C4 | F | 83 | Chronic renal failure | 13 | 6.52 |
| C5 | F | 85 | Metastatic cancer of lung | 3 | 6.04 |
| C6 | M | 46 | Myocardial infarction | 7 | 6.5 |
| C7 | F | 85 | Obstructive Pulmonary Disease | 15 | 6.53 |
| C8 | F | 82 | Malignant Melanoma | 5 | 6.92 |
| C9 | F | 84 | Cardiorespiratory Arrest | 4 | 6.01 |
| C10 | F | 90 | Heart and Respiratory Failure | 3 | 6 |
| C11 | M | 88 | Multiple organ failure | 3 | 6.03 |
| C12 | F | 84 | Cerebrovascular Accident | 9 | 5.96 |
| C13 | M | 85 | Myelodisplastic syndrome | 11 | 6.06 |
| C14 | M | 80 | Myelodisplastic syndrome | 12 | 6.08 |
| C15 | F | 85 | Respiratory failure | 4 | 6.3 |
| C16 | F | 83 | Cardiopulmonary arrest | 4 | 6.16 |
| C17 | F | 88 | Ischemic Heart Disease | 11 | 5.93 |
| C18 | M | 65 | IHD | 9 | 6.64 |
| C19 | M | 70 | Cardiac arrest | 9 | 6.18 |

TABLE 2-continued

Demographic details, cause of death and RNA quality-determining parameters

| Code | Gender | Age at death | Cause of Death | PMI | Ph |
|---|---|---|---|---|---|
| C20 | M | 65 | Ischemic Heart Disease | 6 | 6.49 |
| C21 | M | 65 | Heart Disease | 10 | 6.45 |
| C22 | M | 65 | Cardiac arrest | 12 | 6.78 |
| C23 | M | 68 | Cardiac arrest | 16 | 6 |
| Total 23 | 11M/13F | 78.2 ± 11.4 | Sudden death 10/Prolonged 13 | 7.8 ± 4.1 | 6.3 ± 0.3 |
| PD1 | F | 65 | Cardiopulmonary failure | 4 | 6.28 |
| PD2 | M | 75 | Infectious disease/IHD | 15 | 6.36 |
| PD3 | M | 77 | PD | 4 | 6.38 |
| PD4 | M | 71 | IHD | 6 | 6.00 |
| PD5 | M | 74 | PD/IHD | 4 | 6.41 |
| PD6 | M | 63 | Cardiopulmonary failure/PD | 5 | 6.42 |
| PD7 | M | 88 | Aspiration/PD | 20 | 6.48 |
| PD8 | M | 66 | PD | 5 | 6.42 |
| PD9 | F | 86 | Cardiopulmonary failure | 5 | 6.59 |
| PD10 | M | 78 | PD | 5 | 6.16 |
| PD11 | M | 71 | Intestinal Bleeding | 12 | 6.05 |
| PD12 | F | 60 | Stroke | 4 | 6.29 |
| PD13 | F | 66 | Respiratory failure | 10 | 6.51 |
| PD14 | M | 83 | PD | 2 | 5.96 |
| PD15 | M | 74 | PD | 8 | 6.42 |
| PD16 | M | 72 | Pneumonia | 6 | 5.88 |
| PD17 | M | 69 | PD/Cancer | 3 | 6.00 |
| PD18 | M | 82 | Cardiopulmonary failure | 4 | 5.79 |
| PD19 | M | 73 | Coronary Artery Disease | 11 | 5.92 |
| PD20 | M | 76 | Pneumonia/PD | 5 | 5.97 |
| PD21 | M | 81 | Coronary Artery Disease | 5 | 6.02 |
| PD22 | F | 78 | Coronary Artery Disease/PD | 6 | 6.39 |
| Total 22 | 17M/5F | 74 ± 7.4 | Sudden death 11/Prolonged 12 | 6.8 ± 4.8 | 6.2 ± 0.2 |

TABLE 3

Clinical characteristics of Parkinson's Disease subjects

| Code | Gender | Age at Onset | Disease Duration | H&Y | Onset Symptom | Dementia | Depression | Dyskinesia | Autonomic Dysfunction |
|---|---|---|---|---|---|---|---|---|---|
| PD1 | F | 50 | 15 | 4 | Tremor | No | No | Yes | No |
| PD2 | M | 67 | 8 | 5 | Gait | No | No | No | No |
| PD3 | M | 64 | 13 | 5 | Gait | No | No | Yes | No |
| PD4 | M | 51 | 20 | 5 | Slowness | No | No | Yes | No |
| PD5 | M | 53 | 21 | 5 | Tremor | No | No | Yes | Syncope |
| PD6 | M | 53 | 10 | 5 | Tremor | No | Yes | No | No |
| PD7 | M | 77 | 11 | 4 | Tremor | No | No | No | No |
| PD8 | M | 55 | 11 | 5 | Tremor | No | No | Yes | No |
| PD9 | F | 77 | 9 | 5 | Tremor | No | Yes | No | No |
| PD10 | M | 56 | 22 | 5 | Gait | Yes | Yes | Yes | No |
| PD11 | M | 44 | 27 | 5 | Tremor | No | No | Yes | No |
| PD12 | F | 40 | 20 | 3 | Stiffness | No | No | Yes | Incontinence |
| PD13 | F | 56 | 10 | 5 | Tremor | Yes | Yes | No | No |
| PD14 | M | 80 | 3 | 4 | Tremor | No | Yes | No | Hypotension |
| PD15 | M | 64 | 10 | 4 | Stiffness | Yes | Yes | Yes | Constipation |
| PD16 | M | 46 | 26 | 4 | Stiffness | Yes | Yes | Yes | Hypotension |
| PD17 | M | 59 | 10 | 5 | Tremor | No | No | Yes | No |
| PD18 | M | 74 | 8 | 3 | Depression | No | Yes | No | No |
| PD19 | M | 70 | 3 | 3 | Gait | Yes | Yes | No | Incontinence |
| PD20 | M | 72 | 4 | 5 | Gait | Yes | No | No | Incontinence |
| PD21 | M | 68 | 13 | 5 | Tremor | Yes | No | Yes | Incontinence |
| PD22 | F | 68 | 10 | 5 | Gait | Yes | No | Yes | No |
| | 17M/5F | 61.1 ± 11.5 | 12.9±6.9 | 4.5 ± 0.7 | | | | | |

Abbreviations:
F = female,
M = male,
H&Y = Hoehn and Yahr clinical stage of Parkinson's Disease (1 = mild unilateral disease-5 = severe end-stage disease)

TABLE 4

Genes significantly regulated in ≧18 out of 21 regions.

| Gene Symbol | Affymetrix gene fragment ID[1] | Gene Name | No of Regions | Regions not present | Mean FC | Mean P | SEQ IDs |
|---|---|---|---|---|---|---|---|
| MRPS6[2] (SLC5A3) | 212944_at | Mitochondrial ribosomal protein S6 | 20 | HIPP | 2.1 | .001 | 1-5 |
| HIST1H2BD | 235456_at | Histone 1, H2bd | 20 | Pt | 2.0 | .012 | 6-7 |
| RBM3 | 208319_s_at | RNA binding motif (RNP1, RRM) protein 3 | 20 | LC | −1.4 | .006 | 8 |
| SLC38A2[3] | 222982_x_at | Solute carrier family 38, member 2 | 20 | HIPP | 1.6 | .006 | 9-10 |
| MRPS6[2] | 213164_at | Mitochondrial ribosomal protein S6 | 19 | HIPP, Hyp | 2.3 | .003 | 1-5 |
| CHORDC1 | 218566_s_at | Cysteine/histidine-rich domain (CHORD)-containing, zinc binding protein 1 | 19 | HIPP, Pulv | 1.9 | .007 | 11 |
| CIRBP | 200810_s_at | Cold inducible RNA binding protein | 19 | HIPP, Pulv | −2.2 | .007 | 12-14 |
| SLC38A2[3] | 220924_s_at | Solute carrier family 38, member 2 | 19 | Hyp, Pulv | 1.7 | .014 | 9-10 |
| FLJ33814 | | Hypothetical protein FLJ33814 | 18 | AMG, Cere- | 1.5 | .006 | 15 |
| FUSIP1 | 225348_at | FUS interacting protein (serine/arginine-rich) 1 | 18 | HIPP, LC, VTA | 1.6 | .012 | 16-19 |
| PRKACB[4] | 225644_at | Protein kinase, cAMP-dependent, catalytic, beta | 18 | HIPP, NB, Th | −1.9 | .007 | 20-21 |
| STIP1 | 213330_s_at | Stress-induced-phosphoprotein 1 (Hsp70/Hsp90-organizing protein) | 18 | AMG, Pulv, Th | 1.8 | .015 | 22 |
| SUV420H1 | 222759_at | Suppressor of variegation 4-20 homolog 1 | 18 | NB, Pulv, Th | −1.6 | .012 | 23-28 |

[1]Annotated by Affymetrix.
[2]Two out of 3 fragments representing the MRPS6 gene were included in the top candidate genes list. Original Frag. 212944_at in now called SLC5A3 (the solute carrier family 5 member 3 gene)
[3]Two out of 3 fragments representing the MRPS6 gene were included in the top candidate genes list
Abbreviations:
HIPP = hippocampus
Pt = putamen
LC = locus ceruleus,
Hyp = hypothalamus,
Pulv = Pulvinar,
AMG = amygdala,
Cere = cerebellar hemisphere,
VTA = ventral tegmental area,
NB = nucleus basalis,
Th = thalamus
[4]Additional Affymetrix frags. include 235780_at, 202742_s_at, and 202741_at

TABLE 5

Summary of biological plausibility of top candidate genes
GENE ONTOLOGY[1]

| Gene Symbol | Biological function | Process | Component | Location |
|---|---|---|---|---|
| MRPS6 | structural constituent of ribosome | protein biosynthesis | Mitochondrial small ribosomal subunit | 21q21.3-q22.1 |
| HIST1H2BD | DNA binding | chromosome organization and biogenesis, nucleosome assembly | Nucleus, chromosome, nucleosome | 6p21.3 |
| RBM3 | RNA processing | RNA, nucleotide, nucleic acid binding | N/A | Xp11.2 |
| SLC38A2 | a sodium-coupled neutral amino acid transporter (16)[2] | glutamate-glutamine cycle/glutamine transporter (13) | N/A | 12q |
| CHORDC1 | heat shock protein 90-interacting protein (17)[2] | N/A | N/A | 11q14.3 |
| CIRBP | RNA, nucleotide and nucleic acid binding | Response to cold | Nucleus | 19p13.3 |
| FLJ33814 | N/A | N/A | N/A | 22q12.1 |
| FUSIP1 | RNA splicing factor activity, transesterification mechanism, RS domain binding, unfolded protein binding | assembly of spliceosomal tri-snRNP, cytoplasmic transport, mRNA export from nucleus, mRNA splice site selection, nuclear mRNA splicing, via spliceosome, regulation of transcription | Cytoplasm, nucleoplasm, nucleus | 1p36.11 |
| PRKACB | ATP binding, cAMP-dependent protein kinase activity, magnesium ion binding, nucleotide binding, protein serine/threonine kinase activity, transferase activity | G-protein signaling, coupled to cAMP nucleotide second messenger, protein amino acid phosphorylation, signal transduction | cAMP-dependent protein kinase complex, nucleus | 1p36.1 |

TABLE 5-continued

Summary of biological plausibility of top candidate genes
GENE ONTOLOGY[1]

| Gene Symbol | Biological function | Process | Component | Location |
| --- | --- | --- | --- | --- |
| STIP1 | binding | response to stress | Golgi apparatus, nucleus | 11q13 |
| SUV420H1* | Histone lysine N-methyltransferase activity (H4-K20 specific | histone methylation | condensed nuclear chromosome, pericentric region | 11q13.2 |

[1]Annotated from Entrez Gene (ncbi.nlm.nih.gov)
[2]Proposed biological function (see reference)
*Drosophila analogue
N/A = Not assigned

TABLE 6

| CHIP (Plus 2) | Affy Frag ID | Gene Symbol | Gene Name | Genebank ID | | |
|---|---|---|---|---|---|---|
| 232923(51) | 202259_s_at | (CG012, CG030, LOC88523, PFAAP5) | Hypothetical gene CG012 | U50530 | U50531 | |
| 244644(51) | 214130_s_at | (FLJ21272, PDE4DIP) | (FLJ39739 protein, Phosphodiesterase 4D interacting protein (myomegalin), Similar to KIAA0454 protein) | AK024925 | NM_001002810 | |
| 244643(51) | 214129_at | (FLJ21272, PDE4DIP) | (FLJ39739 protein, Phosphodiesterase 4D interacting protein (myomegalin), Similar to KIAA0454 protein) | AK024925 | NM_001002810 | |
| 257791(51) | 227321_at | (GATS, MGC2463, STAG3) | (Opposite strand transcription unit to STAG3, Stromal antigen 3) | BC100779 | BC090867 | AK092358 |
| 240532(51) | 209911_x_at | (HIST1H2BD, HIST1H2BL, HIST1H2BN) | (Histone 1, H2bd, Histone 1, H2bl, Histone 1, H2bn) | BC096122 | BC002842 | |
| 231464(51) | 200800_s_at | (HSPA1A, HSPA1B) | (Heat shock 70 kDa protein 1A, Heat shock 70 kDa protein 1B, Protein tyrosine phosphatase, non-receptor type substrate 1-like 3) | BC009322 | BC018740 | BC002453 |
| 231463(51) | 200799_at | (HSPA1A, HSPA1B) | (Heat shock 70 kDa protein 1A, Heat shock 70 kDa protein 1B, Protein tyrosine phosphatase, non-receptor type substrate 1-like 3) | BC009322 | BC018740 | BC002453 |
| 367020(51) | 1553327_at | ARMCX4 | Armadillo repeat containing, X-linked 4 | BC032236 | | |
| 235270(51) | 204608_at | ASL | Argininosuccinate lyase | BC033146 | BC008195 | |
| 237248(51) | 206587_at | CCT6B | Chaperonin containing TCP1, subunit 6B (zeta 2) | NM_006584 | | |
| 233914(51) | 203252_at | CDK2AP2 | CDK2-associated protein 2 | BC002850 | BC016704 | |
| 249066(51) | 218566_s_at | CHORDC1 | Cysteine and histidine-rich domain (CHORD)-containing, zinc binding protein 1 | BC017789 | | |
| 255663(51) | 225191_at | CIRBP | Cold inducible RNA binding protein | BC000403 | BC000901 | NM_001280 |
| 231474(51) | 200810_s_at | CIRBP | Cold inducible RNA binding protein | BC000403 | BC000901 | NM_001280 |
| 231475(51) | 200811_at | CIRBP | Cold inducible RNA binding protein | BC000403 | BC000901 | NM_001280 |
| 258526(51) | 228057_at | DDIT4L | DNA-damage-inducible transcript 4-like | BC013592 | NM_145244 | |
| 235662(51) | 205000_at | DDX3Y | DEAD (Asp-Glu-Ala-Asp) box polypeptide 3, Y-linked | BC034942 | | |
| 108356(51) | 37590_g_at | DKFZp547K1113 | Hypothetical protein DKFZp547K1113 | AL831826 | | |
| 257678(51) | 227208_at | DLNB14 | Similar to DLNB14 | AB094093 | | |
| 239644(51) | 209015_s_at | DNAJB6 | DnaJ (Hsp40) homolog, subfamily B, member 6 | BC002446 | BC000177 | |
| 368539(51) | 1554360_at | FCHSD2 | FCH and double SH3 domains 2 | BC010394 | | |
| 231559(51) | 200895_s_at | FKBP4 | FK506 binding protein 4, 59 kDa | BC007924 | BC001786 | |
| 231558(51) | 200894_s_at | FKBP4 | FK506 binding protein 4, 59 kDa | BC007924 | BC001786 | |
| 245555(51) | 215046_at | FLJ23861 | Hypothetical protein FLJ23861 | BC032837 | | |
| 256116(51) | 225644_at | FLJ33814 | Hypothetical protein FLJ33814 | AK091133 | | |
| 255820(51) | 225348_at | FUSIP1 | FUS interacting protein (serine/arginine-rich) 1 | BC005039 | BC001107 | BC010074 |
| 232300(51) | 201636_at | FXR1 | Fragile X mental retardation, autosomal homolog 1 | BC028983 | BC071575 | |
| 258008(51) | 227539_at | GNA13 | Guanine nucleotide binding protein (G protein), alpha 13 | AF493902 | | |
| 369812(51) | 1556126_s_at | GPATC2 | G patch domain containing 2 | BC063474 | BC042193 | |
| 269267(51) | 238803_at | HECTD2 | HECT domain containing 2 | BC040187 | | |
| 233478(51) | 202814_s_at | HEXIM1 | Hexamethylene bis-acetamide inducible 1 | BC006460 | | |

TABLE 6-continued

| CHIP (Plus 2) | Affy Frag ID | Gene Symbol | Gene Name | Genebank ID | | | |
|---|---|---|---|---|---|---|---|
| 265920(51) | 235456_at | HIST1H2BD | Histone 1, H2bd | BC096122 | BC002842 | | |
| 261264(51) | 230795_at | HIST2H4 | Histone 2, H4 | NM_003548 | | | |
| 233245(51) | 202581_at | HSPA1B | Heat shock 70 kDa protein 1B | DQ388429 | | | |
| 255299(51) | 224826_at | KIAA1434 | Hypothetical protein KIAA1434 | BC027588 | | | |
| 233706(51) | 203042_at | LAMP2 | Lysosomal-associated membrane protein 2 | BC002965 | | | |
| 243887(51) | 213371_at | LDB3 | LIM domain binding 3 | BC010929 | | | |
| 258575(51) | 228106_at | LOC441010 | LOC441010 | not found | | | |
| 371445(51) | 1558795_at | LOC441157 | LOC441157 | BC009738 | | | |
| 371445(51) | 1558796_a_at | LOC441157 | LOC441157 | | | | |
| 250042(51) | 219543_at | MAWBP | MAWD binding protein | | | | |
| 255346(51) | 224873_s_at | MRPS25 | Mitochondrial ribosomal protein S25 | | | | |
| 243462(51) | 212944_at | SLC5A3 | Solute carrier family 5 | BC000547 | BC010076 | NM_032476 BC042752 | |
| 243681(51) | 213164_at | MRPS6 | Mitochondrial ribosomal protein S6 | BC000547 | BC010076 | NM_032476 BC042752 | |
| 255392(51) | 224919_at | MRPS6 | Mitochondrial ribosomal protein S6 | BC000547 | BC010076 | NM_032476 BC042752 | |
| 256420(51) | 225949_at | NRBP2 | Nuclear receptor binding protein 2 | NM_178564 | BC113873 | | |
| 238199(51) | 207543_s_at | P4HA1 | Procollagen-proline, 2-oxoglutarate 4-dioxygenase (proline 4-hydroxylase), alpha polypeptide I | BC034998 | | | |
| 243238(51) | 212718_at | PAPOLA | Poly(A) polymerase alpha | NM_032632 | BC036014 | | |
| 258564(51) | 228095_at | PHF14 | PHD finger protein 14 | NM_001007157 | NM_014660 | | |
| 267688(51) | 226317_at | PPP4R2 | Protein phosphatase 4, regulatory subunit 2 | NM_174907 | AJ271448 | BC110889 | |
| 266244(51) | 235780_at | PRKACB | Protein kinase, cAMP-dependent, catalytic, beta | BC035058 | BC016285 | | |
| 232791(51) | 202127_at | PRPF4B | PRP4 pre-mRNA processing factor 4 homolog B (yeast) | BC059713 | | | |
| 245742(51) | 215233_at | PTDSR | Phosphatidylserine receptor | BC066654 | | | |
| 259973(51) | 229504_at | RAB23 | RAB23, member RAS oncogene family | | NM_015167 | | |
| 244299(51) | 213784_at | RABL4 | RAB, member of RAS oncogene family-like 4 | | | | |
| 238958(51) | 208319_s_at | RBM3 | RNA binding motif (RNP1, RRM) protein 3 | BC006825 | | | |
| 258448(51) | 227979_at | RBM30 | RNA binding motif protein 30 | | | | |
| 260661(51) | 230192_at | RFP2 | Ret finger protein 2 | AF241850 | | | |
| 242659(51) | 212138_at | SCC-112 | SCC-112 protein | NM_015200 | BC041361 | BC009650 | AF294791 |
| 250188(51) | 219689_at | SEMA3G | Sema domain, immunoglobulin domain (Ig), short basic domain, secreted, (semaphorin) 3G | NM_015571 | BC08583 | | |
| 245301(51) | 214790_at | SENP6 | SUMO1/sentrin specific protease 6 | | | | |
| 107710(51) | 35626_at | SGSH | N-sulfoglucosamine sulfohydrolase (sulfamidase) | NM_018976 | BC029379 | | |
| 253476(51) | 222982_x_at | SLC38A2 | Solute carrier family 38, member 2 | NM_018976 | BC029379 | | |
| 248541(51) | 218041_x_at | SLC38A2 | Solute carrier family 38, member 2 | NM_018976 | BC029379 | | |
| 251423(51) | 220924_s_at | SLC38A2 | Solute carrier family 38, member 2 | NM_006819 | | | |
| 243846(51) | 213330_s_at | STIP1 | Stress-induced-phosphoprotein 1 (Hsp70/Hsp90-organizing protein) | | | | |
| 253253(51) | 222759_at | SUV420H1 | Suppressor of variegation 4-20 homolog 1 (Drosophila) | BC104483 | BC065287 | BC087834 | BC002522 BC012933 |
| 254079(51) | 223588_at | THAP2 | Hypothetical protein DKFZp564l0422 | NM_031435 | BC099714 | | |
| 270039(51) | 239575_at | TMEM10 | Transmembrane protein 10 | BC033737 | BC008358 | | |
| 257726(51) | 277256_at | USP31 | Ubiquitin specific protease 31 | | | | |
| 371080(51) | 1558117_s_at | USP31 | Ubiquitin specific protease 31 | | | | |

TABLE 6-continued

| CHIP (Plus 2) | Affy Frag ID | Gene Symbol | Gene Name | Genebank ID |
|---|---|---|---|---|
| 239405(51) | 208775_at | XPO1 | Exportin 1 (CRM1 homolog, yeast) | |
| 253707(51) | 223214_s_at | ZHX1 | Zinc fingers and homeoboxes 1 | |
| 256991(51) | 226520_at | | | |
| 272727(51) | 242263_at | | CDNA FLJ37844 fis, clone BRSSN2012622 | |
| 272185(51) | 241721_at | | Transcribed locus, weakly similar to NP_703324.1 glutamic acid-rich protein (garp) [*Plasmodium falciparum* 3D7] | |
| 266020(51) | 235556_at | | | |
| 270774(51) | 240310_at | | Transcribed locus | |
| 259124(51) | 228655_at | | Unknown mRNA sequence | |
| 267017(51) | 236553_at | | Transcribed locus | |
| 252809(51) | 222315_at | | | |
| 244160(51) | 213645_at | | | |
| 260284(51) | 229815_at | | CDNA clone IMAGE: 4814828 | |

What is claimed is:

1. A method of diagnosing Parkinson's Disease in a patient, comprising: detecting the level of expression of one or more genes selected from the group consisting of: the mitochondrial ribosome protein S6 (MRPS6) gene, the solute carrier family 5 gene (SLC5A3), the solute carrier family 38, member 2 gene (SLC38A2), the cAMP dependent protein kinase, the beta catalytic subunit gene (PRKACB), the cysteine and histidine-rich containing zinc binding protein 1 gene (CHORDC1), and the FUS interacting protein (serine/arginine-rich) 1 gene (FUSIP1), in a biological sample from said patient, wherein differential expression of said one or more genes in the sample as compared to control levels of expression of said one or more genes is indicative of Parkinson's Disease.

2. The method of claim 1, wherein said biological sample is blood.

3. The method of claim 1, wherein the sample is a brain tissue sample.

4. The method of claim 1, wherein the patient is exhibiting symptoms of Parkinson's Disease or is being treated for Parkinson's Disease.

5. The method of claim 1, wherein the level of expression of one or more genes is determined by a nucleic acid polymerization or hybridization technology.

6. The method of claim 1, wherein at least one of said genes comprises MRPS6, SLC5A3, SLC38A2, PRKACB, CHORDC1, and FUSIP1.

7. The method of claim 1, wherein said one or more genes include at least two of MRPS6, CHORDC1, SLC38A2, SLC5A3, PRKACB and FUSIP1.

8. The method of claim 1, wherein said one or more genes are differentially expressed in one or more brain regions of the Parkinson's Disease patient, said brain regions being selected from the group consisting of substantia nigra, ventral tegmental area, cingulate cortex (BA35), insular cortex, amygdala, nucleus basalis, caudate, putamen, nucleus accumbens, globus pallidus, mediodorsal thalamus, pulvinar, subthalamic nucleus, nucleus ambiguous, cerebellar hemisphere, anterior cerebellar vermis, dorsal raphe, locus ceruleus, hypothalamus, hippocampus and reticular formation.

9. The method of claim 1, wherein the level of expression of said one or more genes is normalized to the expression level of a housekeeping gene as a control.

10. The method of claim 1, further comprising, treating said patient for Parkinson's Disease.

11. A method for evaluating Parkinson's Disease in a patient, comprising:

(a) determining a first level of expression of one or more genes selected from the group consisting of: MRPS6, SLC5A3, SLC38A2, PRKACB, CHORDC1, and FUSIP1, in a biological sample from a Parkinson's Disease patient;

(b) administering to said patient a treatment for Parkinson's Disease; and (c) determining a second level of expression of said one or more genes in a biological sample obtained from the patient during the course of said treatment, wherein differential expression of said one or more genes in the first sample as compared to the second sample is indicative of effective treatment for Parkinson's Disease.

12. The method of claim 11, wherein the biological samples are blood samples.

13. The method of claim 11, wherein at least one of said genes comprises MRPS6, SLC5A3, SLC38A2, PRKACB, CHORDC1, and FUSIP1.

14. The method of claim 11, wherein the one or more genes are differentially expressed in one or more brain regions of the Parkinson's Disease patient, said one or more brain regions being selected from the group consisting of substantia nigra, ventral tegmental area, cingulate cortex (BA35), insular cortex, amygdala, nucleus basalis, caudate, putamen, nucleus accumbens, globus pallidus, mediodorsal thalamus, pulvinar, subthalamic nucleus, nucleus ambiguous, cerebellar hemisphere, anterior cerebellar vermis, dorsal raphe, locus ceruleus, hypothalamus, hippocampus and reticular formation.

15. The method of claim 11, wherein the level of expression of said one or more genes is normalized to the expression level of a housekeeping gene as a control.

16. A method of diagnosing Parkinson's Disease in a patient, comprising:

detecting the level of one or more gene products in a biological sample from said patient, said one or more gene products being the translation products of one or more genes selected from the group consisting of: MRPS6, SLC5A3, SLC38A2, PRKACB, CHORDC1, and FUSIP1, wherein a difference in the levels of said one or more gene products in the sample as compared to control levels is indicative of Parkinson's Disease.

17. The method of claim 16, wherein said biological sample is blood.

18. The method of claim 16, wherein the patient is exhibiting symptoms of Parkinson's Disease or is being treated for Parkinson's Disease.

19. The method of claim 16, wherein the level of the one or more gene products is determined by an immunological assay.

20. The method of claim 16, wherein at least one said gene product comprises MRPS6, SLC5A3, SLC38A2, PRKACB, CHORDC1, and FUSIP1.

21. The method of claim 16, wherein said one or more gene products include at least two of MRPS6, SLC5A3, SLC38A2, PRKACB, CHORDC1, and FUSIP1.

22. The method of claim 16, wherein the gene product is differentially expressed in one or more brain regions of the Parkinson's Disease patient, the one or more brain regions being selected from the group consisting of substantia nigra, ventral tegmental area, cingulate cortex (BA35), insular cortex, amygdala, nucleus basalis, caudate, putamen, nucleus accumbens, globus pallidus, mediodorsal thalamus, pulvinar, subthalamic nucleus, nucleus ambiguous, cerebellar hemisphere, anterior cerebellar vermis, dorsal raphe, locus ceruleus, hypothalamus, hippocampus and reticular formation.

23. A method for evaluating Parkinson's Disease in a patient, comprising:
   (a) determining a first level of one or more gene products in a biological sample from a Parkinson's Disease patient, said one or more gene products being translation products of genes selected from the group consisting of: MRPS6, SLC5A3, SLC38A2, PRKACB, CHORDC1, and FUSIP1;
   (b) administering to said patient a treatment for Parkinson's Disease; and
   (c) determining a second level of said one or more gene products in a biological sample obtained from the patient during the course of said treatment, wherein a difference in the levels of said one or more gene products in the first sample as compared to the second sample is indicative of effective treatment for Parkinson's Disease.

24. The method of claim 23, wherein the biological samples are blood samples.

25. The method of claim 23, wherein at least one said gene product comprises MRPS6, SLC5A3, SLC38A2, PRKACB, CHORDC1, and FUSIP1.

26. The method of claim 23, wherein said one or more gene products include at least two of MRPS6, SLC5A3, SLC38A2, PRKACB, CHORDC1, and FUSIP1.

27. The method of claim 23, wherein the gene product is differentially expressed in one or more brain regions of the Parkinson's Disease patient, the one or more brain regions being selected from the group consisting of substantia nigra, ventral tegmental area, cingulate cortex (BA35), insular cortex, amygdala, nucleus basalis, caudate, putamen, nucleus accumbens, globus pallidus, mediodorsal thalamus, pulvinar, subthalamic nucleus, nucleus ambiguous, cerebellar hemisphere, anterior cerebellar vermis, dorsal raphe, locus ceruleus, hypothalamus, hippocampus and reticular formation.

* * * * *